(12) United States Patent
de Crombrugghe et al.

(10) Patent No.: US 7,160,722 B2
(45) Date of Patent: Jan. 9, 2007

(54) MASTER BONE FORMATION TRANSCRIPTION FACTOR: COMPOSITIONS AND METHODS OF USE

(75) Inventors: Benoit de Crombrugghe, Houston, TX (US); Kazuhisa Nakashima, Houston, TX (US); Xin Zhou, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 528 days.

(21) Appl. No.: 09/734,329

(22) Filed: Nov. 30, 2000

(65) Prior Publication Data

US 2002/0156031 A1 Oct. 24, 2002

(51) Int. Cl.
| | |
|---|---|
| *C12N 5/10* | (2006.01) |
| *C12N 5/06* | (2006.01) |
| *C12N 5/08* | (2006.01) |
| *C12N 15/00* | (2006.01) |
| *C12N 1/21* | (2006.01) |
| *C07H 21/04* | (2006.01) |

(52) U.S. Cl. ................. 435/354; 536/23.5; 435/320.1; 435/325; 435/252.3; 435/252.33; 435/364; 435/366

(58) Field of Classification Search ............... 536/23.1, 536/23.5, 24.3; 435/325, 243, 419, 252.3, 435/252.33

See application file for complete search history.

(56) References Cited

OTHER PUBLICATIONS

Marra et al, The WashU-HHMI Mouse EST Project, sequence database, publically available Aug. 23, 1996.*
Bi et al., "Sox9 is required for cartilage formation," *Nat Genet*, 22(1), 85-89, 1999.
Franceschi, "The developmental control of osteoblast-specific gene expression: role of specific transcription factors and the extracellular matrix environment", *Crit. Rev. Biol. Med.*, 10:40-57, 1999.
Gashler et al., "A novel repression module, an extensive activation domain, and a bipartite nuclear localization signal defined in the immediate-early transcription factor egr-1," *Mol Cell Biol*, 13(8), 4556-4571, 1993.
Jackson and Demmer, "Peroxisome proliferator-activated receptor activators modulate the osteoblastic maturation of MC3T3-E1 preosteoblasts," *FEBS Lett*, 471:119-124, 2000.
Katagiri et al., "Bone morphogenetic protein-2 converts the differentiation pathyway of C2C12 myoblasts into the osteoblast lineage," *J. Cell Biol*, 127(6 Pt 1), 1755-1766, 1994.
Lefebvre et al., "Sox9 is a potent activator of the chondrocyte-specific enhancer of the proα1(II) collagen gene," *Mol Cell Biol*, 17(4), 2336-2346, 1997.
Rowe et al., "Maps from two interspecific backcross dna panels available as a community genetic mapping resource," *Mamm Genome*, 5(5), 253-274, 1994.
Schreiber et al., "Rapid detection of octamer binding proteins with 'mini-extract', prepared from a small number of cells," *Nucleic Acids Res*, 17(15), 6419-6425, 1989.
Subramaniam et al., "Identification of a novel tgf-β-regulated gene encoding a putative zinc finger protein in human osteoblasts," *Nucleic Acids Res*, 23(23), 4907-4912, 1995.
Grills et al., "High throughput mouse sequencing," *Database EMBL Online!*, Accession No. ACO55703, XP002220834 (whole document), 2002.
Nakashima et al., "Novel zinc finger-containing transcription factor osterix Is required for osteoblast differentiation and bone formation," *Cell*, 108:17-29, 2002.
Schock et al., "Common and diverged functions of the drosophila gene pair D-spl and buttonhead," *Mechanisms of Develp.*, 89:125-132, 1999.

* cited by examiner

*Primary Examiner*—Celine Qian
*Assistant Examiner*—Jennifer Dunston
(74) *Attorney, Agent, or Firm*—Fulbright & Jaworski

(57) ABSTRACT

A novel gene expressed selectively by osteoblast lines is provided. Expression of the gene is highly restricted to cells of osteoblast lineage, including precursor cells. Also provided is a method for promoting bone formation by providing agents that bind to the novel gene within osteoblast cells to stimulate bone formation.

21 Claims, 18 Drawing Sheets

```
  1 ATTCTCCCATTCTCCCTCCCTCTCCCTTTCTCTCCACTGGCTCTCCTCTCGAGTTCTCTCCTGAGGACCCGGCTCCCCAGCTCCCAGCTGGGACCGGTCCCCAGCTCCCCAGCTGGGACGATGGCGTCCTCTCTGCTGGAG     120
                                                                                                                                M  A  S  S  L  L  E        7
121 GAAGAAGCTCACTATGGCTCCCCTCTGGCCATGCTGACTGCTGCTTGCAGCAAATTTGGCGGCTCTAGCCCTCTGCGGGACTCAACACCCTGGGGAAAGGAGGCAAAGAAGCCA                                    240
  8  E  E  E  A  H  Y  G  S  S  P  L  A  M  L  T  A  A  C  S  K  F  G  G  S  S  P  L  R  D  S  T  T  L  G  K  G  G  T  K  K  P                           47
241 TACGCTGACCTTTCAGCCCCCAAAACATGGGGAGACGCCTACCCAGCTCCTTCTCAAGCACCAATGACTCTCTCTCCAGGCAGTCCTCCAGCTCCTTCTGGCTATGCAAAT                                      360
 48  Y  A  D  L  S  A  P  K  T  M  G  D  A  Y  P  A  P  F  S  S  T  N  G  L  L  S  P  A  G  S  P  P  A  P  S  G  Y  A  N                                 87
361 GACTACCCACCCTTCCCTCACTCATTTCCTGGGCCTGCCAAGAGCCTGTGCACAGCTCGTGCTAGTGTCTACACTTCCTGAT                                                                    480
 88  D  Y  P  P  F  P  H  S  F  P  G  P  T  G  A  Q  D  P  G  L  L  V  P  K  G  H  S  S  S  D  C  L  P  S  V  Y  T  S  L  D                             127
481 ATGACTCATCCCTATGGCTCGTGTACAAGGCCAGGCATCTCACCAGGTCCAGGCAACACACTCCTTGGTGGGACATGCACCCTCTGGCTAGGTGGT                                                      600
128  M  T  H  P  Y  G  S  W  Y  K  A  G  I  H  A  G  I  S  P  G  P  N  T  P  T  P  W  N  D  M  H  P  G  G  N  W  L  G  G                                167
601 GGTCAGGGCGAGGGTGATGGCTGCAAGGGACACTGTCCAAGGACCCCTGCCAGCTCGAACCCATCTGACTTTGCTCCCCTTAACCCAGCTCCTTAC                                                      720
168  G  Q  G  Q  G  D  G  L  Q  G  T  L  S  T  G  P  A  Q  P  P  L  N  P  Q  L  P  T  Y  P  S  D  F  A  P  L  N  P  A  P  Y                              207
721 CCAGGCGCCCACCTCTTGCAACCAGGGCCAGCGGTTGGATATGCGGGGCAGTGCCCCAAGATGTCTTACCCCAAGACCGTTGGCAATAGTGGGCAACTGGAGGGAAGTGGTGCAGCCAAACCCCTCGG                    840
208  P  A  P  H  L  L  Q  P  G  P  Q  H  V  L  P  Q  D  V  Y  K  P  K  A  V  G  N  S  G  Q  L  E  G  S  G  A  A  K  P  P  R                              247
841 GGTGCTGGACACAGGGGCAGCGGTGGAGGGTACGCAGGAGCAGGGTACGCAGGAGCAGGAGCGTTCTCAGGAGCGGCTCGGGGCTGCGAGAGCAGCTGGCTGGCTGAGAAG                                      960
248  G  A  G  T  G  G  G  S  G  G  Y  A  G  S  G  A  G  R  S  T  C  D  C  P  N  C  Q  E  L  E  R  L  G  A  A  A  A  G  L  R  K                           287
961 AAGCCCATTCACAGCTGCCACATCCCTGGTTGCGGGCAAGGTTACGGCAAGGCTTGCGCATCTGAAAGCCACTGGCGCCACACTGGCGAGAGAAAGAAGTTCACTTGCCTTCTTGTTCTGCCAACTGGCTTTC            1080
288  K  P  I  H  S  C  H  I  P  G  C  G  K  V  Y  G  K  A  S  H  L  K  A  H  L  R  W  H  T  G  E  R  P  F  V  C  N  W  L  F                              327
1080 TGCGGCAAGAGGTTCACTCGCTCAGACGAGCTGGAGCGCCACGTCCGGACCCACACCCACACCCGGGAAGTGGCCTAAGGACGTGGCCGGGAGAGAGGAGCCAATCAGCCGCCCGATCTTCCACT                    1200
328  C  G  K  R  F  T  R  S  D  E  L  E  R  H  V  R  T  H  T  R  E  K  K  F  T  C  L  L  C  S  K  R  F  T  R  S  D  H  L  S                              367
1201 AAACATCAGCGCACCCACGGGGAGCCAGGCCCGGGGCCGCCTCCTGGGCCCTCCGGGCCAAGTGGCCCTAAGGAGCTCGGAGAGCGGAGCGTCGGGGAGGAGGAAGCAATGCAATCCCAGATCTTCCACT              1320
368  K  H  Q  R  T  H  G  E  P  P  G  P  G  P  P  P  S  G  P  K  E  L  G  E  G  R  S  V  G  E  E  A  N  Q  P  P  R  S  S  T                              407
1321 TCGCCTGCACCCCCAGAAAAGCCAAGCATGGGGGCTCCCCAGAGCAGAGCAACCTGCTAGAGATCTGAGCCGGTAGAGAAGTCTCCAGGTCCTCTTGCCAGGGTCTCTTGGC                                   1440
408  S  P  A  P  P  E  K  A  H  G  G  S  P  E  Q  S  N  L  L  E  I  *
```

FIG. 2A-1

```
1441 GTGCTGACCCATTGGTTGCCCTGCTCTCTCTCCTATTGCATGCTATATCTCTGTTCCCCTAGGCTATCTCCTTGTCTCTCTCTTTGTCAAGA 1560
1561 GTCTTAGCCAAACTCCCTCAGGCCTTTGCCAGTGCCTAGTTCCTATGCCTCCTATTGCCTGCCCCTGTTCTTCTCTGCCCATCTTCACAGCTTCATCTGCCTCACATCATTTCT 1680
1681 CATTAACTCGTTGCCATCTAATCTATTCTGCTATTGCCGTTTCCAGCACTTCCAGGCTGTCGCCTGATTCGTCTTCCTGAGCTTGTGTTTCT 1800
1801 TTTTTAAACAAAACACGATGATGATGATAATTTATTGCCCCTGTTGTTCATTAGGAACCAGAGTTGGTGTTAGTAACCTGGCCGGGAGCAGAGTG 1920
1921 CCAAGAAGGGGGAAGTCCAATGGGAGATCTGATCCAAAGATGGGGTGACCCCAGGGTCAGGAGGTACAGTTAACCCCTGAGTACTTAACCCCTCAGGTAAAGAATGCATCTCTGTA 2040
2041 AGTAATAATAATGATAGTGGAGACCTTGCTCGTAGATTTCTATCCTCGAGGGTGTTGAGTTCTTTTCGGTCTTCTTTTCAGTGTTTCGGGTGTTGAGTTTCTGTGGGTGTCTC 2160
2161 TAGACAAATGATAGTGGAGACCTTGCTCGTAGATTTCTATCCTCGAGGGTGTCTCCGAGGTCTCCGAGGTCTCCGAGAGCCCAGCCCAGCCCAGCCCAGTGTTGAGTTTCTGTGGGTGTCTC 2280
2281 TGTTAGGCAGTCACTAAGATCCCCAGCCCAGCCAGCTGACCTGTATCCCCTTGTCGTCATGTTACAGAGAGGCTTTCTCTGGGATCAAATTCAAATAAATCAAGGTGGCGCTTGAGTGCAGGCCTA 2400
2401 CCCTGATCCTCATACCCTGTGACCTAGCTCCTGAAAAGTAGGTGGGCAAACTCCCTAAACTAAACATCCAGAGCCCCAATCGTCCCTTGCCAGGCCTAAGGCCTTGTGCCTTTGAA 2520
2521 GGATTTTGGTTTGGAGGTGCCCTCCTGAAACAGAAGAATTTATAACAGGACAGAAGAAGTCCCTAAACTAAACATCCAGAGCCTAAAGCGTAAAGGGTAAAGCCGTTCAGTGACTTTGTGCCTTTGAA 2640
2641 GAAGCCACGAGAAAGAATTTTATAACAGGACAGAAGAAGTCCCTAAACTAAACATCCAGAGCCTAAAGGCCTAAAGGGTAAAGCCGTTGTGACGGATCGTCCCT 2760
2761 ATGCCTTTCCTGAGATTTTCCTGAGATCTTCCTGTTCCTGTCGTCCTCTTCCTCCTTCCTCTAGGCCTCAAGATAAAGGGTAAAGCCGCTTGTGCCTTTGAA 2880
2881 TTGTGGAATCTTCTTTTTTTTTAATTAATAAATAAAGTTCGATTTCAAAAAAAAAAAAAAAAAAAAAA 2960
```

| Name | Sequence | % Identity |
|---|---|---|
| Osterix | IHSCHIPGCGKVYGKASHLKAHLRWHTGERPFVCNWLFCGKRFTRSDELERHVRTHTREKKFTCLLCSKRFTRSDHLSKHQRTHG | |
| SP3 | Q------T--R-----S----I--M-------Q--R--G----V-PE-----M----A--IK--Q | 77.8% |
| SP4 | Q-V---E---T--R-----------I--M-------Q--R--G-R-E-PE---M----VK--Q | 77.8% |
| SP1 | Q-I---Q---T--R--------------M-------Q--K--G----A-PE-P---M----IK--Q | 77.8% |
| SP2 | K-V---D--TFR-T-L-R--V-L-----M---SY--------Q--A----GD-R-E-AQ-Q---M----T--YK--L | 69.4% |
| FKLF-2 | K-K--YA--E----S----T-------A-S-QE-N-K-A-----A--Y----G----S-PI-E---M----T-A-R-A | 69.4% |
| BTEB-1 | R-K-PYS-----S-----Y-V-----P-T-PD-L-K-S-----T--Y----G-Q-R-P--E---M----T-A-R-T | 68.2% |
| TIEG1 | S-I-SH-----T-F-S------Y-T-----K-S-S-KG-ER--A----T--Y----G-Q-R-P--E---M----T-A-R-L | 64.7% |
| TIEG2 | NYV-SF---R-T-F-S------V-T-----K--N-S-DG-D-K-A-----S--R----G----A-PM-DR--M----T-A-R-M | 63.5% |
| AP-2rep | --R-DFE--N---T-S-----R-T------K-YK-T-EG-TWK-G----T--Y-K--GV-P-K-AD-DR--S----AL-R-R-M | 57.6% |
| IKLF | --F-DYN--T---T-S-----T-------K-YK-T-EG-DW--A----T--Y-K--GA-P-Q-MV-QRS-S----AL-MKR-Q | 57.6% |
| EKLF | A-T-GHE---S-S-S-----T-------K-YA-S-DG-DW--A----T--Y-K--GHRP-C-G--PRA-S----AL-MKR-L | 56.5% |
| LKLF | T-T-SYTN--T-T-S-----T-------K-YH---EG--WK-A----T--Y-K--GHRP-Q-H--DRA-S----AL-MKR-M | 56.5% |
| ZF9 | V-R--FN--R---T-S----Q-T-----K-YR-S-EG-EW--A----T--F-K--GA-P-K-SH-DRC-S----AL-MKR-L | 56.5% |
| GKLF | T-T-DYA---T-T-S-----T-------K-YH-D-DG--WK-A----T--Y-K--GHRP-Q-QK-DRA-S----AL-MKR-F | 55.3% |
| BKLF | --R-DYD--N---T-S-----R-T------K-YK-T-EG-TWK-A----T--F-K--GI-P-Q-PD-DRS-S----AL-RKR-M | 55.3% |

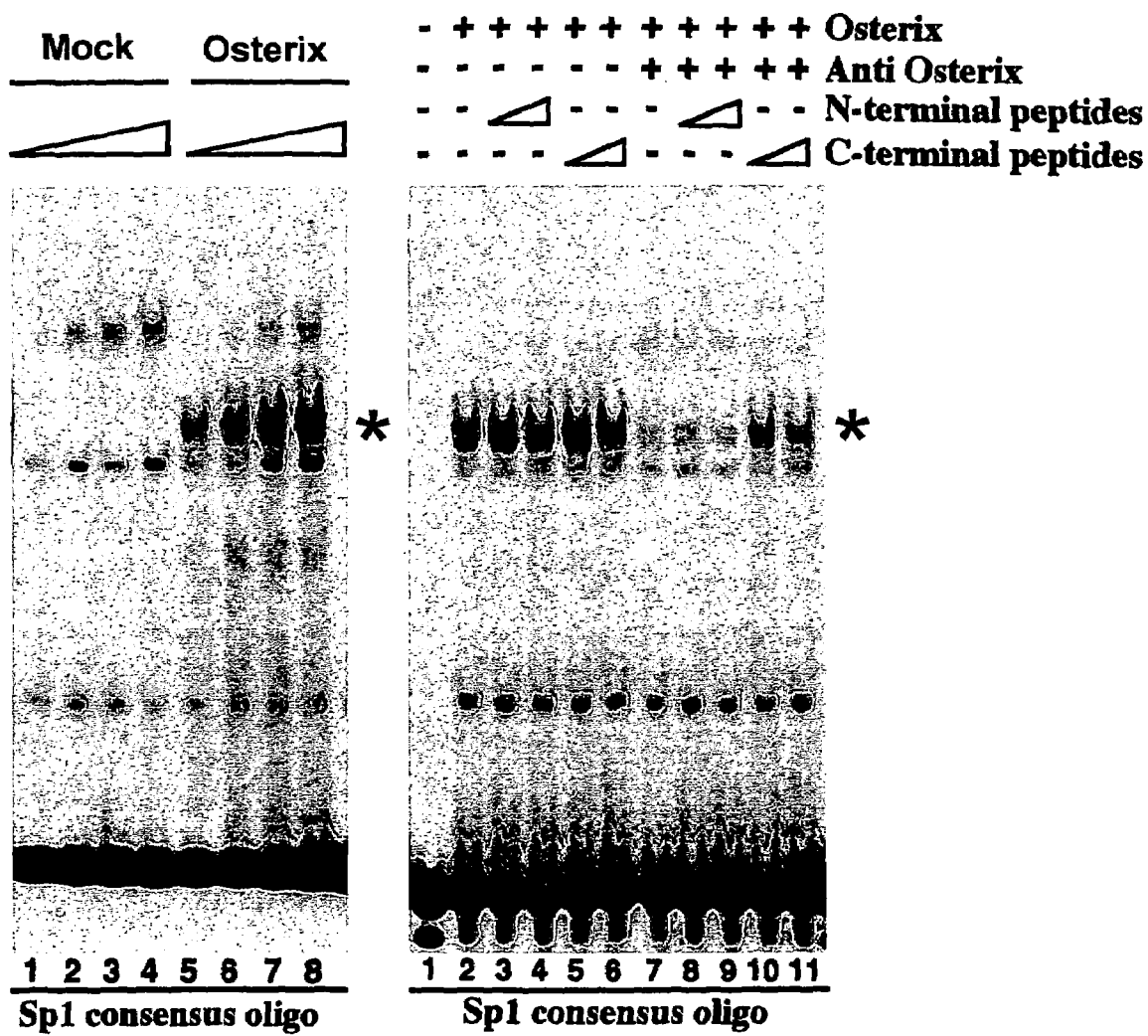

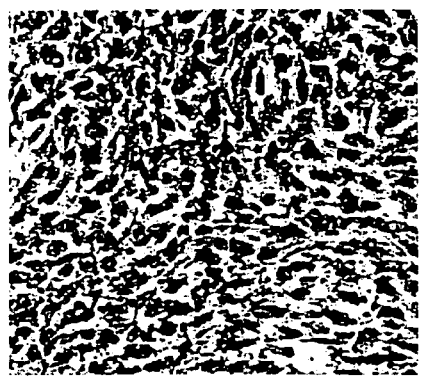
FIG. 9A
FIG. 9C

| | | | |
|---|---|---|---|
| Mouse | 1 | MASSLLEEEAHYGSSPLAMLTAACSKFGGSSPLRDSTTLGKGGTKKPYA- | 50 |
| human | 1 | MASSLLEEEVHYGSSPLAMLTAACSKFGGSSPLRDSTTLGKAGTKKPYSV | 50 |
| Mouse | 51 | --DLSAPKTMGDAYPAPFSSTNGLLSPAGSPPAPASGYANDYPPFPHSFP | 100 |
| human | 51 | GSDLSASKTMGDAYPAPFTSTNGLLSPAGSPPAPTSGYANDYPPFSHSFP | 100 |
| Mouse | 101 | GPTGAQDPGLLVPKGHSSSDCLPSVYTSLDMTHPYGSWYKAGIHAGISPG | 150 |
| human | 101 | GPTGTQDPGLLVPKGHSSSDCLPSVYTSLDMTHPYGSWYKAGIHAGISPG | 150 |
| Mouse | 151 | PGNTPTPWWDMHPGGNWLGGGQGQGDGLQGTLSTGPAQPPLNPQLPTYPS | 200 |
| human | 151 | PGNTPTPWWDMHPGGNWLGGGQGQGDGLQGTLPTGPAQPPLNPQLPTYPS | 200 |
| Mouse | 201 | DFAPLNPAPYPAPHLLQPGPQHVLPQDVYKPKAVGNSGQLEGSGAAKPPR | 250 |
| human | 201 | DFAPLNPAPYPAPHLLQPGPQHVLPQDVYKPKAVGNSGQLEGSGGAKPPR | 250 |
| Mouse | 251 | GAGTGGSGGYAGSGAGRSTCDCPNCQELERLGAAAAGLRKKPIHSCHIPG | 300 |
| human | 251 | GASTGGSGGYGGSGAGRSSCDCPNCQELERLGAAAAGLRKKPIHSCHIPG | 300 |
| Mouse | 301 | CGKVYGKASHLKAHLRWHTGERPFVCNWLFCGKRFTRSDELERHVRTHTR | 350 |
| human | 301 | CGKVYGKASHLKAHLRWHTGERPFVCNWLFCGKRFTRSDELERHVRTHTR | 350 |
| Mouse | 351 | EKKFTCLLCSKRFTRSDHLSKHQRTHGEPGPGPPPSGPKELGEGRSVGEE | 400 |
| human | 351 | EKKFTCLLCSKRFTRSDHLSKHQRTHGEPGPGPPPSGPKELGEGRSTGEE | 400 |
| Mouse | 401 | EANQPPRSSTSPAPPEKAHGGSPEQSNLLEI | 428 |
| human | 401 | EASQTPRPSASPATPEKAPGGSPEQSNLLEI | 431 |

FIG.10

SEQUENCE LISTING

<160> NUMBER OF SEQ ID NOS: 6

<210> SEQ ID NO 1
<211> LENGTH: 2960
<212> TYPE: DNA
<213> ORGANISM: Mus musculus
<220> FEATURE:
<221> NAME/KEY: CDS
<222> LOCATION: (100)..(1383)

<400> SEQUENCE: 1

```
attctcccat tctccctccc tctcccttct ccctctccca ctggctcctc ggttctctcc          60
atctgcctga ctccttggga cccggtcccc agctcgagg atg gcg tcc tct ctg           114
                                            Met Ala Ser Ser Leu
                                              1               5 ctt gag gaa gaa gct cac tat ggc tcc agt ccc ctg gcc atg ctg act          162
Leu Glu Glu Glu Ala His Tyr Gly Ser Ser Pro Leu Ala Met Leu Thr
             10                  15                  20 gca gcc tgc agc aaa ttt ggc ggc tct agc cct ctg cgg gac tca aca          210
Ala Ala Cys Ser Lys Phe Gly Gly Ser Ser Pro Leu Arg Asp Ser Thr
         25                  30                  35 acc ctg ggg aaa gga ggc aca aag aag cca tac gct gac ctt tca gcc          258
Thr Leu Gly Lys Gly Gly Thr Lys Lys Pro Tyr Ala Asp Leu Ser Ala
     40                  45                  50 ccc aaa acc atg ggg gac gcc tac cca gct ccc ttc tca agc acc aat          306
Pro Lys Thr Met Gly Asp Ala Tyr Pro Ala Pro Phe Ser Ser Thr Asn
 55                  60                  65 gga ctc ctc tct cct gca ggt agt cct ccg gcc cca gcc tct ggc tat          354
Gly Leu Leu Ser Pro Ala Gly Ser Pro Pro Ala Pro Ala Ser Gly Tyr
                 70                  75                  80                  85 gca aat gac tac cca ccc ttc cct cac tca ttt cct ggg ccc acc ggt          402
Ala Asn Asp Tyr Pro Pro Phe Pro His Ser Phe Pro Gly Pro Thr Gly
                 90                  95                 100 gcc caa gac cct ggg ctc cta gtg cct aag ggg cac agc tcg tct gac          450
Ala Gln Asp Pro Gly Leu Leu Val Pro Lys Gly His Ser Ser Ser Asp
            105                 110                 115 tgc ctg cct agt gtc tac act tcc ctg gat atg act cat ccc tat ggc          498
Cys Leu Pro Ser Val Tyr Thr Ser Leu Asp Met Thr His Pro Tyr Gly
        120                 125                 130 tcg tgg tac aag gca ggc atc cac gca ggc atc tca cca ggt cca ggc          546
Ser Trp Tyr Lys Ala Gly Ile His Ala Gly Ile Ser Pro Gly Pro Gly
    135                 140                 145 aac aca cct act cct tgg tgg gac atg cac cct ggg ggc aac tgg cta          594
Asn Thr Pro Thr Pro Trp Trp Asp Met His Pro Gly Gly Asn Trp Leu
150                 155                 160                 165 ggt ggt ggt cag ggc cag ggt gat ggg ctg caa ggg aca ctg tcc aca          642
Gly Gly Gly Gln Gly Gln Gly Asp Gly Leu Gln Gly Thr Leu Ser Thr
                170                 175                 180 ggc cct gcc cag cct cca ctg aac ccc cag ctg cct act tac cca tct          690
Gly Pro Ala Gln Pro Pro Leu Asn Pro Gln Leu Pro Thr Tyr Pro Ser
            185                 190                 195 gac ttt gct ccc ctt aac cca gct ccc tac cca gcg ccc cac ctc ttg          738
Asp Phe Ala Pro Leu Asn Pro Ala Pro Tyr Pro Ala Pro His Leu Leu
        200                 205                 210 caa cca ggg ccc cag cat gtc cta ccc caa gat gtc tat aag ccc aag          786
Gln Pro Gly Pro Gln His Val Leu Pro Gln Asp Val Tyr Lys Pro Lys
    215                 220                 225 gcg gtt ggc aat agt ggg caa ctg gag ggg agt ggt gca gcc aaa ccc          834
Ala Val Gly Asn Ser Gly Gln Leu Glu Gly Ser Gly Ala Ala Lys Pro
```

-continued

```
                  230                 235                 240                 245
cct cgg ggt gct ggc aca ggg ggc agc ggt gga tat gcg ggc agt ggg         882
Pro Arg Gly Ala Gly Thr Gly Gly Ser Gly Gly Tyr Ala Gly Ser Gly
                      250                 255                 260 gca ggg cgt tct acc tgc gac tgc ccc aac tgt cag gag cta gag cgg         930
Ala Gly Arg Ser Thr Cys Asp Cys Pro Asn Cys Gln Glu Leu Glu Arg
            265                 270                 275 ctc ggg gca gca gcg gct ggg ctg agg aag aag ccc att cac agc tgc         978
Leu Gly Ala Ala Ala Gly Leu Arg Lys Lys Pro Ile His Ser Cys
        280                 285                 290 cac atc cct ggg tgc ggc aag gtg tac ggc aag gct tcg cat ctg aaa        1026
His Ile Pro Gly Cys Gly Lys Val Tyr Gly Lys Ala Ser His Leu Lys
    295                 300                 305 gcc cac ttg cgc tgg cac act ggc gag agg cct ttc gtc tgc aac tgg        1074
Ala His Leu Arg Trp His Thr Gly Glu Arg Pro Phe Val Cys Asn Trp
310                 315                 320                 325 ctt ttc tgc ggc aag agg ttc act cgc tct gac gag ctg gag cgc cac        1122
Leu Phe Cys Gly Lys Arg Phe Thr Arg Ser Asp Glu Leu Glu Arg His
                      330                 335                 340 gtg cgc act cac acc cgg gag aag aag ttc act tgc ctg ctc tgt tcc        1170
Val Arg Thr His Thr Arg Glu Lys Lys Phe Thr Cys Leu Leu Cys Ser
            345                 350                 355 aag cgc ttt acc aga agc gac cac ttg agc aaa cat cag cgc acc cac        1218
Lys Arg Phe Thr Arg Ser Asp His Leu Ser Lys His Gln Arg Thr His
        360                 365                 370 ggg gag cca ggc ccg gga ccg ccc cca agt ggc cct aag gag ctg ggg        1266
Gly Glu Pro Gly Pro Gly Pro Pro Pro Ser Gly Pro Lys Glu Leu Gly
    375                 380                 385 gag ggt cgc agc gtc ggg gaa gaa gaa gcc aat cag ccg ccc cga tct        1314
Glu Gly Arg Ser Val Gly Glu Glu Glu Ala Asn Gln Pro Pro Arg Ser
390                 395                 400                 405 tcc act tcg cct gca ccc cca gaa aaa gcc cac gga ggc agc cca gag        1362
Ser Thr Ser Pro Ala Pro Pro Glu Lys Ala His Gly Gly Ser Pro Glu
                      410                 415                 420 cag agc aac ctg cta gag atc tgagccgggt agaggaaggt ctccagctcc           1413
Gln Ser Asn Leu Leu Glu Ile
            425 agggtcctct tgccaggctc tcttggcgtg ctggacccat tggttgcccc tcgctctctc      1473 ctattgcatg ctatactctg ggggctctct ctgttcccct aggctatctc cttgcatgtc      1533 tcctcagttc ttctctcttt gtcaagagtc ttagccaaac tcctctcagg cctttgccag      1593 tgcctagttc ctatgctccg acctcctcaa cttttctt tctgcccctg ttcttcacag       1653 cttccatctg gcctcacatc attttctcat taactcgttg ccatctaatc tttctgcttc      1713 ccaatcctat ttgccgtttt cccgaagctt ccaggctgtc gcctcgattc ccccccacct      1773 ttcgtcttcc tgagctttgt gttttctttt tttaaacaaa cacgatgatg atgatgatga      1833 tgatgataat ttattgcccc ctggtgttct tcattaggaa ccagagttaa ggagattggt      1893 gttagtaacc tggccgggag cagagtgcca agaaggggga agtccaatgg ggatctgatc      1953 ccaaagatgg ggtgacccca gggtcaggga ggctgccccc agccttgagt acttaacccc      2013 tatgcgccag gagtaaagaa tagtaatagt aataataata ataattctat ttatctaagt      2073 tatgatgacg ggtcaggtac agtgagctgg agagggaaag ggattctccc cgcccccaag      2133 gaaattctag tcaaatgcat ctctgtatag acaaatgata gtggagacct tgctcgtaga      2193 tttctatcct cgaggtctcc gagagtttct ttttcagttg agttttgggt tgttcggcct      2253 cttttagagt ttctgtgggt gtctctctgt taggcagtca ctaagatccc cagccccagc      2313
```

-continued

```
cagaaagctg tgaaacttca agtcctatgg cggggaggac tggaatgtac cccagtcctc    2373
tcgacccgac tgcagatcag gttcctcccc tgatcctctt ctcatacccT gtgacctcac    2433
caggttatcc ccttgtcgtc atggttacag agagcttgca gctgccatct taaacgtgct    2493
ctttggggga gagcccacct aacaggagga ttttggtttg gaggtgcccc tcctgaaaaa    2553
gtaggtgggc aaaggctttc tctgggatca aattcaaata aatcaagtat ttattgaatg    2613
cttaatatgt gcaaggcctg gtgcctagaa gccacgagaa agaatttata acaggacaga    2673
agtccctaaa ctaaacatcc acaggccccc aatctaggag gtttcactcc attccagtga    2733
cttttaaagc cgctttgtgc ctttgaaatg cctttcctga gattttttgga tcttcctgtt    2793 ctgtcccctg ctccttctag gcctcaagat aaagggtaaa gccatggagt ctgggaagag    2853
cataacgtcg ttgacgggat cgtccctttg tggaatcttt ctttttttttt taatttaata    2913 aataaaagtt cgatttcaaa aaaaaaaaaa aaaaaaaaa aaaaaaa                    2960
```

<210> SEQ ID NO 2
<211> LENGTH: 428
<212> TYPE: PRT
<213> ORGANISM: Mus musculus

<400> SEQUENCE: 2

```
Met Ala Ser Ser Leu Leu Glu Glu Glu Ala His Tyr Gly Ser Ser Pro
  1               5                  10                  15

Leu Ala Met Leu Thr Ala Ala Cys Ser Lys Phe Gly Gly Ser Ser Pro
             20                  25                  30

Leu Arg Asp Ser Thr Thr Leu Gly Lys Gly Gly Thr Lys Lys Pro Tyr
         35                  40                  45

Ala Asp Leu Ser Ala Pro Lys Thr Met Gly Asp Ala Tyr Pro Ala Pro
     50                  55                  60

Phe Ser Ser Thr Asn Gly Leu Leu Ser Pro Ala Gly Ser Pro Pro Ala
 65                  70                  75                  80

Pro Ala Ser Gly Tyr Ala Asn Asp Tyr Pro Pro Phe Pro His Ser Phe
                 85                  90                  95

Pro Gly Pro Thr Gly Ala Gln Asp Pro Gly Leu Leu Val Pro Lys Gly
            100                 105                 110

His Ser Ser Ser Asp Cys Leu Pro Ser Val Tyr Thr Ser Leu Asp Met
        115                 120                 125

Thr His Pro Tyr Gly Ser Trp Tyr Lys Ala Gly Ile His Ala Gly Ile
    130                 135                 140

Ser Pro Gly Pro Gly Asn Thr Pro Thr Pro Trp Trp Asp Met His Pro
145                 150                 155                 160

Gly Gly Asn Trp Leu Gly Gly Gly Gln Gly Gln Gly Asp Gly Leu Gln
                165                 170                 175

Gly Thr Leu Ser Thr Gly Pro Ala Gln Pro Pro Leu Asn Pro Gln Leu
            180                 185                 190

Pro Thr Tyr Pro Ser Asp Phe Ala Pro Leu Asn Pro Ala Pro Tyr Pro
        195                 200                 205

Ala Pro His Leu Leu Gln Pro Gly Pro Gln His Val Leu Pro Gln Asp
    210                 215                 220

Val Tyr Lys Pro Lys Ala Val Gly Asn Ser Gly Gln Leu Glu Gly Ser
225                 230                 235                 240

Gly Ala Ala Lys Pro Pro Arg Gly Ala Gly Thr Gly Gly Ser Gly Gly
                245                 250                 255
```

```
Tyr Ala Gly Ser Gly Ala Gly Arg Ser Thr Cys Asp Cys Pro Asn Cys
            260                 265                 270

Gln Glu Leu Glu Arg Leu Gly Ala Ala Ala Gly Leu Arg Lys Lys
            275                 280                 285

Pro Ile His Ser Cys His Ile Pro Gly Cys Gly Lys Val Tyr Gly Lys
            290                 295                 300

Ala Ser His Leu Lys Ala His Leu Arg Trp His Thr Gly Glu Arg Pro
305                 310                 315                 320

Phe Val Cys Asn Trp Leu Phe Cys Gly Lys Arg Phe Thr Arg Ser Asp
                325                 330                 335

Glu Leu Glu Arg His Val Arg Thr His Thr Arg Glu Lys Lys Phe Thr
            340                 345                 350

Cys Leu Leu Cys Ser Lys Arg Phe Thr Arg Ser Asp His Leu Ser Lys
            355                 360                 365

His Gln Arg Thr His Gly Glu Pro Gly Pro Gly Pro Pro Pro Ser Gly
            370                 375                 380

Pro Lys Glu Leu Gly Glu Gly Arg Ser Val Gly Glu Glu Ala Asn
385                 390                 395                 400

Gln Pro Pro Arg Ser Ser Thr Ser Pro Ala Pro Pro Glu Lys Ala His
                405                 410                 415

Gly Gly Ser Pro Glu Gln Ser Asn Leu Leu Glu Ile
            420                 425

<210> SEQ ID NO 3
<211> LENGTH: 14
<212> TYPE: PRT
<213> ORGANISM: Mus musculus

<400> SEQUENCE: 3

Ala His Gly Gly Ser Pro Glu Gln Ser Asn Leu Leu Glu Ile
1               5                   10

<210> SEQ ID NO 4
<211> LENGTH: 85
<212> TYPE: PRT
<213> ORGANISM: Mus musculus

<400> SEQUENCE: 4

Ile His Ser Cys His Ile Pro Gly Cys Gly Lys Val Tyr Gly Lys Ala
1               5                   10                  15

Ser His Leu Lys Ala His Leu Arg Trp His Thr Gly Glu Arg Pro Phe
            20                  25                  30

Val Cys Asn Trp Leu Phe Cys Gly Lys Arg Phe Thr Arg Ser Asp Glu
        35                  40                  45

Leu Glu Arg His Val Arg Thr His Thr Arg Glu Lys Lys Phe Thr Cys
    50                  55                  60

Leu Leu Cys Ser Lys Arg Phe Thr Arg Ser Asp His Leu Ser Lys His
65                  70                  75                  80

Gln Arg Thr His Gly
            85

<210> SEQ ID NO 5
<211> LENGTH: 244
<212> TYPE: PRT
<213> ORGANISM: Mus musculus

<400> SEQUENCE: 5

Phe Gly Gly Ser Ser Pro Leu Arg Asp Ser Thr Thr Leu Gly Lys Gly
```

```
                1               5              10              15
Gly Thr Lys Lys Pro Tyr Ala Asp Leu Ser Ala Pro Lys Thr Met Gly
                    20                  25                  30

Asp Ala Tyr Pro Ala Pro Phe Ser Ser Thr Asn Gly Leu Leu Ser Pro
                35                  40                  45

Ala Gly Ser Pro Pro Ala Pro Ala Ser Gly Tyr Ala Asn Asp Tyr Pro
            50                  55                  60

Pro Phe Pro His Ser Phe Pro Gly Pro Thr Gly Ala Gln Asp Pro Gly
65                  70                  75                  80

Leu Leu Val Pro Lys Gly His Ser Ser Asp Cys Leu Pro Ser Val
                    85                  90                  95

Tyr Thr Ser Leu Asp Met Thr His Pro Tyr Gly Ser Trp Tyr Lys Ala
                    100                 105                 110

Gly Ile His Ala Gly Ile Ser Pro Gly Pro Gly Asn Thr Pro Thr Pro
                115                 120                 125

Trp Trp Asp Met His Pro Gly Gly Asn Trp Leu Gly Gly Gly Gln Gly
            130                 135                 140

Gln Gly Asp Gly Leu Gln Gly Thr Leu Ser Thr Gly Pro Ala Gln Pro
145                 150                 155                 160

Pro Leu Asn Pro Gln Leu Pro Thr Tyr Pro Ser Asp Phe Ala Pro Leu
                165                 170                 175

Asn Pro Ala Pro Tyr Pro Ala Pro His Leu Leu Gln Pro Gly Pro Gln
            180                 185                 190

His Val Leu Pro Gln Asp Val Tyr Lys Pro Lys Ala Val Gly Asn Ser
        195                 200                 205

Gly Gln Leu Glu Gly Ser Gly Ala Ala Lys Pro Pro Arg Gly Ala Gly
        210                 215                 220

Thr Gly Gly Ser Gly Gly Tyr Ala Gly Ser Gly Ala Gly Arg Ser Thr
225                 230                 235                 240

Cys Asp Cys Pro

<210> SEQ ID NO 6
<211> LENGTH: 166
<212> TYPE: PRT
<213> ORGANISM: Mus musculus

<400> SEQUENCE: 6

Phe Gly Gly Ser Ser Pro Leu Arg Asp Ser Thr Thr Leu Gly Lys Gly
1               5                   10                  15

Gly Thr Lys Lys Pro Tyr Ala Asp Leu Ser Ala Pro Lys Thr Met Gly
                    20                  25                  30

Asp Ala Tyr Pro Ala Pro Phe Ser Ser Thr Asn Gly Leu Leu Ser Pro
                35                  40                  45

Ala Gly Ser Pro Pro Ala Pro Ala Ser Gly Tyr Ala Asn Asp Tyr Pro
            50                  55                  60

Pro Phe Pro His Ser Phe Pro Gly Pro Thr Gly Ala Gln Asp Pro Gly
65                  70                  75                  80

Leu Leu Val Pro Lys Gly His Ser Ser Asp Cys Leu Pro Ser Val
                    85                  90                  95

Tyr Thr Ser Leu Asp Met Thr His Pro Tyr Gly Ser Trp Tyr Lys Ala
                    100                 105                 110

Gly Ile His Ala Gly Ile Ser Pro Gly Pro Gly Asn Thr Pro Thr Pro
                115                 120                 125

Trp Trp Asp Met His Pro Gly Gly Asn Trp Leu Gly Gly Gly Gln Gly
```

-continued

```
            130                 135                 140
Gln Gly Asp Gly Leu Gln Gly Thr Leu Ser Thr Gly Pro Ala Gln Pro
145                 150                 155                 160

Pro Leu Asn Pro Gln Leu
                165
```

MASTER BONE FORMATION TRANSCRIPTION FACTOR: COMPOSITIONS AND METHODS OF USE

The government owns rights in the present invention pursuant to grant number HL41264-12 from the National Institutes of Health.

BACKGROUND OF THE INVENTION

1. Field of the Invention

The present invention relates generally to osteoblast cells and their role in bone formation. More specifically, the invention relates to the identification and isolation of genes encoding osteoblast cell proteins required for bone formation.

2. Description of Related Art

Bone formation is a carefully controlled developmental process involving morphogen-mediated patterning signals that define areas of initial mesenchyme condensation followed by induction of cell-specific differentiation programs to produce chondrocytes and osteoblasts. Positional information is conveyed via gradients of molecules, such as Sonic Hedgehog, that are released from cells within a particular morphogenic field together with region-specific patterns of hox gene expression. These, in turn, regulate the localized production of bone morphogenetic proteins and related molecules which initiate chondrocyte- and osteoblast- specific differentiation programs. Differentiation requires the initial commitment of mesenchymal stem cells to a given lineage, followed by induction of tissue-specific patterns of gene expression. Considerable information about the control of osteoblast-specific gene expression has come from analysis of the promoter regions of genes encoding proteins like osteocalcin that are selectively expresses in bone. Both general and tissue-specific transcription factors control this promoter. Osf2/Cbfa1, the first osteoblast specific transcription factor to be identified, is expressed early in the osteoblast lineage and interacts with specific DNA sequences in the osteocalcin promoter essential for its selective expression in osteoblasts. (Franceschi 1999). Cbfa1 is needed for osteoclast differentiation.

The reduced bone mineral density (BMD) observed in osteoporosis results, in part, from reduced activity of bone-forming osteoblasts (Jackson 2000). The identification of transcription factors that participate in the cell differentiation process has been beneficial in developing treatment protocols for osteoporosis. It is likely that other transcription factors participate in the differentiation process as well. It would be beneficial to identify a master transcription for the development of agents to enhance bone formation in treatment of bone diseases such as osteoporosis.

SUMMARY OF THE INVENTION

The present invention seeks to overcome these and other drawbacks inherent in the prior art by providing genes found to be expressed by osteoblasts. As such, the present invention concerns the identification of a gene, termed Osterix, which is expressed by osteoblasts and encodes molecules required for bone formation. Thus, the invention is generally drawn to DNA segments encoding Osterix proteins or polypeptides. Accordingly, the present invention provides Osterix gene and methods of making and using such genes. The invention also concerns other proteins that bind to and therefore modulate the activity of Osterix. Methods to identify these proteins are also set forth.

The DNA segments of the invention may be further characterized as comprising an isolated osteoblast gene whose product is required for bone formation.

Preferred DNA segments of the invention encode an Osterix protein or polypeptide comprising a contiguous amino acid sequence from SEQ ID NO:2. The DNA segments of the invention may alternatively be defined as comprising a contiguous nucleic acid sequence from SEQ ID NO:1.

The Osterix proteins or polypeptides of the invention are typically characterized as comprising a zinc finger domain and a transactivation domain comprising a proline rich domain. The Osterix proteins of the invention may be further characterized as being expressed by osteoblasts. The Osterix proteins of the invention may be described as a polypeptide of about 46 kDa.

The zinc finger domain of Osterix may be characterized as including an amino acid sequence from between position 290 and position 374 from SEQ ID NO:2. It may further be defined by SEQ ID NO:4.

The transactivation domain of Osterix may be characterized as including an amino acid sequence from between position 27 and position 270 from SEQ ID NO:2. It may further be defined by SEQ ID NO:5.

The proline rich domain of Osterix may be characterized as including an amino acid sequence from between position 27 and position 192 from SEQ ID NO:2. It may further be defined by SEQ ID NO:6.

In certain embodiments, the present invention provides Osterix genes that encode a Osterix protein of about 428 amino acids in length. Preferably, the Osterix genes encode an Osterix protein that has the amino acid sequence of SEQ ID NO:2.

In other preferred embodiments, the present invention provides Osterix genes that encode an Osterix protein or polypeptide comprising a contiguous amino acid sequence from SEQ ID NO:2.

The Osterix gene of the invention are preferably cDNAs, although genomic copies are by no means excluded. The Osterix gene may be obtained from the C2C12 mouse cell line, normally a progenitor of skeletal muscle cells (ATCC # CRL1772), although other Osterix gene sources are not excluded.

Biological functional equivalents and structural equivalents of the Osterix gene as described hereinbelow are also included within the present invention.

Certain preferred Osterix genes will comprise the nucleic acid sequences of SEQ ID NO:1. However, this is by no means limiting and is just one exemplary embodiment of the present invention. Detailed directions as how to make and use many other such Osterix genes are included herein.

Genes of the invention may also be operatively linked to other protein-encoding nucleic acid sequences. This will generally result in the production of a fusion protein following expression of such a nucleic acid construct. Both N-terminal and C-terminal fusion proteins are contemplated.

Virtually any protein- or polypeptide-encoding DNA sequence, or combinations thereof, may be fused to an Osterix sequence in order to encode a fusion protein. This includes DNA sequences that encode targeting polypeptides, therapeutic proteins, proteins for recombinant expression, proteins to which one or more targeting polypeptides is attached, protein subunits and the like. One of skill in the art will recognize that one may use any sequence to obtain a fusion Osterix protein depending on the function desired.

Another embodiment of the invention may generally be described as a nucleic acid segment characterized as a nucleic acid segment comprising a sequence region that consists of at least 14 contiguous nucleotides that have the same sequence as, or are complementary to, 14 contiguous nucleotides of SEQ ID NO:1. Alternatively, the nucleic acid segment of the invention may be characterized as a nucleic acid segment of from 14 to about 10,000 nucleotides in length that hybridizes to the nucleic acid segment of SEQ ID NO:1, or the complement thereof, under standard hybridization conditions.

Preferred nucleic acid segments comprise a sequence region of at least 14 contiguous nucleotides from SEQ ID NO:1 or the complement thereof. Other preferred nucleic acid segments comprise segments that hybridize to the nucleic acid segment of SEQ ID NO:1 or the complement thereof In more preferred embodiments, the segment is about 25 nucleotides in length. Alternatively, the segment may be up to about 3 kilobase pairs in length.

The invention further includes DNA segments comprising the 5' untranslated regions (5' UTR) and 3' UTR of Osterix cDNA and 5'-flanking regions and 3'-flanking regions of Osterix. These 5' UTR and 3' UTR genomic DNA sequences and 5'-flanking and 3'-flanking sequences are important in terms of regulating osteoblast-specific transcription of the Osterix gene. It has been found that the 5' flanking sequence may be particularly useful in targeting the transcription of foreign genes in osteoblasts. For example, the inventors contemplate experiments wherein an isolated promoter fragment of the Osterix gene will be used to drive transcription of a reporter gene such as the luciferase gene in transgenic mice. Expression of Osterix gene in osteoblast cells but not in other cell types will be used as indicators that the isolated promoter fragment is a osteoblast specific promoter. Thus, in one aspect of the invention, a DNA segment comprising the 5'-flanking regions of Osterix operatively linked to a heterologous gene or a DNA segment that encodes a selected protein are contemplated. Tissue specific osteoblast promoters may be used to obtain targeted expression of a gene in osteoblasts.

Another aspect of the invention generally involves a purified or a substantially purified Osterix protein or polypeptide. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition. In certain embodiments, the protein or polypeptide of the invention may be operatively linked to a second polypeptide sequence. It is also contemplated that purified or substantially purified polypeptides of between about 5 to 428 amino acids in length comprising a contiguous sequence from SEQ ID NO:2 are encompassed by the invention. Thus, for example the invention contemplates polypeptides or proteins of from about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 415, 420, to 428 contiguous amino acids of SEQ ID NO:2. Polypeptides with intermediate lengths are also contemplated as useful. In addition, polypeptides encoding specific functional regions of the Osterix protein are also contemplated. Thus, polypeptides containing about 84 contiguous amino acids of SEQ ID NO:2 encoding the zinc finger-domain, from amino acid number 290 to amino acid number 374 of SEQ ID NO:2; polypeptides containing about 243 contiguous amino acids of SEQ ID NO:2 encoding the transactivation-domain, from amino acid number 27 to amino acid number 270 of SEQ ID NO:2; and polypeptides containing about 165 contiguous amino acids of SEQ ID NO:2 encoding the proline richdomain, from amino acid number 27 to amino acid number 192 of SEQ ID NO:2 are also contemplated. Some such preferred sequence may also be defined by SEQ ID NO:4, SEQ ID NO:5, or SEQ ID NO:6.

Recombinant vectors and plasmids form another important aspect of the present invention. In such vectors, the Osterix gene is positioned under the transcriptional control of a promoter, generally a promoter operative in a mammalian or human cell. "Positioned under the transcriptional control of" means that the Osterix sequence is positioned downstream from and under the transcriptional control of the promoter such that the promoter is capable of directing expression of the encoded Osterix protein in a mammalian or human host cell upon introduction of the vector into such a cell.

The recombinant vectors of the invention will thus generally comprise an Osterix gene operatively positioned downstream from a promoter, wherein the promoter is capable of directing expression of the Osterix gene in a mammalian or human cell. Preferably the promoter will direct expression of Osterix in an amount sufficient to allow Osterix detection. Such promoters are thus "operative" in mammalian and human cells.

Expression vectors and plasmids in accordance with the present invention may comprise one or more constitutive promoters, such as viral promoters or promoters from mammalian genes that are generally active in promoting transcription. Examples of constitutive viral promoters include the HSV, TK, RSV, LTR promoter sequence from retroviral vectors, SV40 and CMV promoters, of which the CMV promoter is a currently preferred example. Examples of constitutive mammalian promoters include various housekeeping gene promoters, as exemplified by the β actin promoter. Other promoters may be dectin-1, dectin-2, human CD11c, F4/80, SM22, RSV, SV40, Ad MLP, betaactin, MHC class I or MHC class II promoter, Inducible promoters and/or regulatory elements are also contemplated for use with the expression vectors of the invention. Examples of suitable inducible promoters include promoters from genes such as cytochrome P450 genes, heat shock protein genes, metallothionein genes, hormone-inducible genes, such as the estrogen gene promoter, and such like. Promoters that are activated in response to exposure to ionizing radiation, such as fos, jun and egr-1, are also contemplated.

Tissue-specific promoters and/or regulatory elements will be useful in certain embodiments. Examples of such promoters that may be used with the expression vectors of the invention include promoters from the liver fatty acid binding (FAB) protein gene, specific for colon epithelial cells; the keratin genes, specific for keratinocytes; the insulin gene, specific for pancreatic cells; the transphyretin, α1-antitrypsin, plasminogen activator inhibitor type 1 (PAI-1), apolipoprotein AI and LDL receptor genes, specific for liver cells; the myelin basic protein (MBP) gene, specific for oligodendrocytes; the glial fibrillary acidic protein (GFAP) gene, specific for glial cells; OPSIN, specific for targeting to the eye; and the neural-specific enolase (NSE) promoter that is specific for nerve cells.

The construction and use of expression vectors and plasmids is well known to those of skill in the art. Virtually any mammalian cell expression vector may thus be used connection with the genes disclosed herein.

Preferred vectors and plasmids will be constructed with at least one multiple cloning site. In certain embodiments, the expression vector will comprise a multiple cloning site that is operatively positioned between a promoter and an Osterix gene sequence. Such vectors may be used, in addition to their uses in other embodiments, to create N-terminal fusion proteins by cloning a second protein-encoding DNA segment into the multiple cloning site so that it is contiguous and in-frame with the Osterix sequence.

In other embodiments, expression vectors may comprise a multiple cloning site that is operatively positioned downstream from the expressible Osterix gene sequence. These vectors are useful, in addition to their uses, in creating C-terminal fusion proteins by cloning a second protein-encoding DNA segment into the multiple cloning site so that it is contiguous and in-frame with the Osterix sequence.

Vectors and plasmids in which a second protein- or RNA-encoding nucleic acid segment is also present are, of course, also encompassed by the invention, irrespective of the nature of the nucleic acid segment itself.

A second reporter gene may be included within an expression vector of the present invention. The second reporter gene may be comprised within a second transcriptional unit. Suitable second reporter genes include those that confer resistance to agents such as neomycin, hygromycin, puromycin, zeocin, mycophenolic acid, histidinol and methotrexate. Alternatively, the reporter gene may be a gene that can be easily detected such as luciferase or green fluorescent protein.

Expression vectors may also contain other nucleic acid sequences, such as IRES elements, polyadenylation signals, splice donor/splice acceptor signals, and the like.

Particular examples of suitable expression vectors are those adapted for expression using a recombinant adenoviral, recombinant adeno-associated viral (AAV) or recombinant retroviral system. Vaccinia virus, herpes simplex virus, cytomegalovirus, and defective hepatitis B viruses, amongst others, may also be used.

In certain embodiments, the expression vector or plasmid may comprise an Osterix reporter gene that has the nucleic acid sequence of SEQ ID NO:1.

Recombinant host cells form another aspect of the present invention. Such host cells will generally comprise at least one copy of an isolated Osterix gene. Preferred cells for expression purposes will be prokaryotic host cells or eukaryotic host cells. Accordingly, cells such as bacterial, yeast, fungal, insect, nematode and plant cells are also possible. Most preferably, the host cell will be a bacterial host cell. An example of a preferred bacterial host cell is *E. coli*. Alternatively, an example of a preferred eukaryotic host cell is an osteoblast cell or a mesenchymal precursor cell. However, it will be understood that other cell types are not excluded from those of the invention.

In certain embodiments, the recombinant host cells will preferably incorporate an Osterix gene in a manner effective to allow the cell to express, or to be stimulated to express, Osterix, most preferably, in an amount sufficient to allow Osterix detection. The recombinant host cell will thus preferably include an Osterix gene that was introduced into the cell by means of a recombinant vector.

In certain embodiments, the recombinant host cell will express the Osterix gene to produce the encoded Osterix protein, preferably, in an amount sufficient to allow Osterix detection. The expressed Osterix protein or polypeptide preferably includes a contiguous amino acid sequence from SEQ ID NO:2.

The recombinant Osterix proteins or polypeptides of the invention may, in certain embodiments, be prepared by expressing an Osterix protein or polypeptide in a recombinant host cell and purifying the expressed Osterix protein or polypeptide away from total recombinant host cell components.

Examples of suitable recombinant host cells include VERO cells, HeLa cells, cells of Chinese hamster ovary (CHO) cell lines, COS cells, such as COS-7, and W138, BHK, HepG2, 3T3, RIN, MDCK, A549, PC 12, K562 and 293 cells.

Cells of primary cell lines that have been established after removing cells from a mammal and culturing the cells for a limited period of time are also included within the cells of the present invention. These cells may be engineered by the hand of man and returned to the same host animal from which they were originally recovered. Such cells that contain an Osterix gene fall within the scope of the invention, irrespective of their location.

Naturally, recombinant cells also include those cells that are located within the body of an animal or human subject, as may have been targeted by gene therapy. These cells include all those that comprise at least one copy of an Osterix gene or vector, irrespective of the manner in which gene was acquired, e.g., by transfection, infection and the like.

In certain particular embodiments, recombinant host cells that comprise an Osterix gene that comprises the nucleic acid sequence of SEQ ID NO:1 are contemplated.

Many methods of using Osterix genes are obtained from the present invention. More specific methods obtained from the invention are methods for identifying an inhibitory agent, or a stimulatory agent, or a modulatory agent, comprising admixing an cell expressing or capable of expressing Osterix with a candidate substance and identifying if the candidate substance inhibits, stimulates, or modulates the expression of Osterix. The cells expressing Osterix may comprise engineered cells that express recombinant Osterix, or osteoblasts. In yet another embodiment, the transfected cells that contain the Osterix cDNA can be co-transfected with a reporter gene that is under the transcriptional control of Osterix. Thus, if the candidate substance for example induces or stimulated Osterix expression, the reporter gene whose expression is controlled by Osterix will be expressed and measured. The reporter gene may be luciferase, green fluorescent protein or any other gene whose expression is readily detected.

Thus, provided is a method for identifying an effector of Osterix transcription, said method comprising admixing, (i) a vector expressing Osterix as well as a reporter gene that measures Osterix expression, and (ii) a candidate substance, and identifying the candidate substance that alters the transcription of the reporter gene by said Osterix. The vector expressing Osterix may be comprised in engineered cells that express recombinant Osterix.

The effector is a substance that stimulates or modulates cell differentiation of a precursor cell into an osteoblasts by Osterix.

The invention also provides methods for identifying a stimulatory agent, comprising the steps of: a) admixing a composition comprising a population of precursor cells capable of expressing Osterix; b) incubating the admixture with a candidate substance; c) testing said admixture for precursor cell differentiation; and d) identifying the candidate substance that stimulates the differentiation of precursor cells into osteoblasts. In some embodiments, the precursor cell may be a mesenchymal precursor cell.

The invention also provides methods for identifying an inhibitory agent, or a stimulatory agent, comprising the steps of: (a) admixing a first composition comprising a population of recombinant cells expressing Osterix with a second composition comprising a population of osteoblasts; (b) incubating the admixture with a candidate substance; (c) testing said admixture for osteoblast activation; and (d) identifying a candidate substance that inhibits, or stimulates, the activation of osteoblasts.

The invention further provides agents that modulate the activity of Osterix by binding to Osterix in osteoblasts. These agents can inhibit, or stimulate, or modulate Osterix-mediated activation of bone formation. Thus, these agents can be used effectively in therapy for Osteoporosis, bone fracture repair acceleration, bone tissue reconstruction and other bone disorders. In preferred embodiments, these agent of the invention will be formulated in a pharmaceutical acceptable medium. In some embodiments these agents may be naturally occurring proteins in osteoblasts.

Therefore, these agents (proteins) may be identified by the yeast two hybrid method. The agents may also be identified by using Osterix specific antibodies to precipitate Osterix from osteoblast cells thereby co-precipitating some of the agents that bind and modulate Osterix. The agents co-precipitated may be the identified by protein sequencing or other methods known to the skilled artisan.

The Osterix gene, proteins, agents that interact with the protein to activate or stimulate the differentiation of bone cells may be used for the treatment of several bone disorders, such as osteoporosis, glucocorticoid induced osteoporosis, Paget's disease, abnormally increased bone turnover, periodontal disease, tooth loss, bone fractures, rheumatoid arthritis, periprosthetic osteolysis, osteogenesis imperfecta, metastatic bone disease, hypercalcemia of malignancy and the like.

Following longstanding patent law convention, the word "a" and "an", when used in conjunction with the word comprising, mean "one or more" in this specification, including the claims.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A shows the hind limb of mouse embryo at 13.5 d.p.c. FIG. 1B shows a sagital section of mouse embryo at 14.5 d.p.c. illustrating signals in osteoblasts in frontal bone (fb), mandible (mbl), maxilla (mxl), and vertebra (vtbr). FIG. 1C shows the hind limb of mouse embryo at 15.5 d.p.c. FIG. 1D shows the upper and lower jaws of mouse embryo at 16.5 d.p.c. illustrating signals in osteoblasts in mandible and maxilla. Mesenchyme of tooth bud (tb) also showed positive signal (oc=oral cavity; mc=Meckel's cartilage). FIG. 1E shows the hind limb of mouse embryo at 17.5 d.p.c. FIG. 1F shows the hind limb of 13-day old mouse showing signals in primary and secondary ossification centers (soc) as well as prehypertrophic zone of growth plate (t=tibia; f=fibra; poc=primary ossification center; gp=growth plate; bm=bone marrow).

FIG. 2A and FIG. 2B. FIG. 2A shows nucleotide sequence of cDNA for mouse Osterix (SEQ ID NO: 1) and deduced amino acid sequence of mouse Osterix (SEQ ID NO: 2). This sequence begins in FIG. 2A-1 and continues into FIG. 2A-2. FIG. 2B shows comparison of the amino acid sequence in the zinc-finger domain (SEQ ID NO: 4) with sequences of related zinc-finger proteins (SEQ ID NOS: 8, 9, 10, 11, 12, 13, 14, 15, 16, 17, 18, 19, 20, 21 and SEQ ID NO: 22). Amino acids in these related sequences that are different are indicated by black boxes. Cysteine and histidine residues of the zinc-finger motif are indicated by asterisks. Numbers to the right of the sequences indicate percent identity.

FIG. 4A and FIG. 4B. DNA binding activity of Osterix. FIG. 4A shows a mammalian expression vector containing Osterix cDNA and a control empty expression vector transfected into COS-7 cells. Increasing amount of cell extracts were incubated with radiolabeled double-stranded Sp1 oligonucleotides, and the protein-DNA complexes were analyzed by EMSA. FIG. 4B shows cell extract from COS-7 cells transfected with the expression plasmids were incubated with radiolabeled double-stranded Sp1 oligonucleotides in the absence or presence of anti-Osterix antibodies and in the presence or absence of epitope peptides as indicated. The protein-DNA complexes were analyzed by EMSA. Asterisks show the Osterix-DNA complexes.

FIG. 5A: coronal sections of upper part of the skull; FIG. 5B: coronal sections of the head showing upper and lower jaw; FIG. 5C: longitudinal sections of the humerus; FIG. 5D: transverse sections of vertebrae in lumbar region. AB/HT: Alcian Blue and hematoxylin treocin stain; Col/al: probe for mouse proα1(I) collagen RNA; BSP: probe for mouse bone sialoprotein RNA; Cbfa1: probe for mouse Cbfa1 RNA.

FIG. 6A. Oligonucleotide sequences of the different wild type and mutant probes. FIG. 6B. EMSA of lysates of COS-7 cells transfected with a Osterix expression vector with the indicated $^{32}$P-labeled probes.

FIG. 7A. structures of Osterix cDNA and protein (SEQ ID NO:1). FIG. 7B. Osterix (SEQ ID NO:1) or subfragments of Osterix (SEQ ID NO:1) were fused inframe with the BAL4 DNA-binding domain. For example, pSGC22(27–428) includes nucleotides from between position 27 and position 428 of Osterix (SEQ ID NO: 1). The corresponding DNAs were placed under the control of the SV40 promoter/enhancer (pSG424) and transfected transiently into COS-7 cells together with a luciferease reporter plasmid containing five copies of the Gal4 binding site. FIG. 7C. expression of Gal4 fusion polypeptides in transfected cells. Asterisks show the Osterix fusion polypeptides.

FIG. 9A, FIG. 9B, and FIG. 9C. Expression of Osterix RNA. FIG. 9A. Change of phenotype of C2C12 cells treated with BMP-2. Confluent C2C12 Cells were incubated for 24 h with DMEM containing 5% FBS without or with BMP-2 (300 ng/ml) or TGFb-1 (25 ng/ml). FIG. 9B. Time course of expression of Osterix, OSF2/Cbfa1 and osteocalcin mRNAs in C2C12 cells. Confluent C2C12 cells were incubated with DMEM containing 5% FBS in the presence or absence (control) of BMP-2 (300 ng/ml) or TGF-b1 (25 ng/ml) for the indicated time. Total RNA (10 ug) was analyzed by Northern blot using a Osterix cCNA probe. Filters were rehybridized with rat osteocalcin and mouse Cbfa1 cDNA probes successively. Amounts of mRNAs were verified by rehybridizing the filters with a GAPDH probe. FIG. 9C. Expression of Osterix RNA in various cell lines and newborn mouse tissues.

FIG. 10. Comparison of amino acid sequences of human Osterix (SEQ ID NO: 23) and mouse Osterix (SEQ ID NO: 2).

DESCRIPTION OF ILLUSTRATIVE EMBODIMENTS

A. Introduction

Bone formation is a complex process that involves the differentiation of mesenchymal cell precursors into osteoblasts. The interaction of osteoblast precursors with cells of the osteoblast lineage is a pre-requisite for osteoblast formation. The osteoblast-specific transcription factor Cbfa1 has been known for some time to be essential for osteoblast differentiation. It was speculated that other transcription factors that would control the differentiation pathway also existed.

The present inventors have shown that osteoblasts specifically express at least one previously unknown transcription factor at the time they first become osteoblasts. The gene is expressed in nascent bones at the time of osteoblast differentiation and also expressed later in secondary ossification centers, indicating that its expression is maintained in more mature osteoblasts. The inventors have inactivated the gene and generated mouse that are homozygous mutants for the gene. These mouse completely lack bones. Thus, Osterix is a master transcription factor that controls osteoblast differentiation.

The inventors have characterized this molecule as comprising, 428 amino acids, as defined in SEQ ID NO:2. Further, the identified molecule consists of a zinc finger domain and a transactivation domain comprising a proline rich domain. Due to the specification of the gene's expression in osteoblasts and in osteoblast precursor cells, the inventors have labeled the identified 428 amino acid molecule "Osterix".

The zinc finger domain of Osterix may be further characterized as comprising three zinc fingers, defined by amino acids 290–374 of SEQ ID NO:2, that exhibit significantly homology with a similar motif in the previously described transcription factors Sp-1, Sp-2, Sp-3 and Sp-4 (see FIG. 2B). However, outside of the domain containing the three zinc fingers, the Osterix protein exhibited no homology with these four transcription factors or with any other transcription factors. In contrast, Sp-1, Sp-2, Sp-3 and Sp-4 show considerable homologies both within and outside their zinc finger domains.

Figure 3:
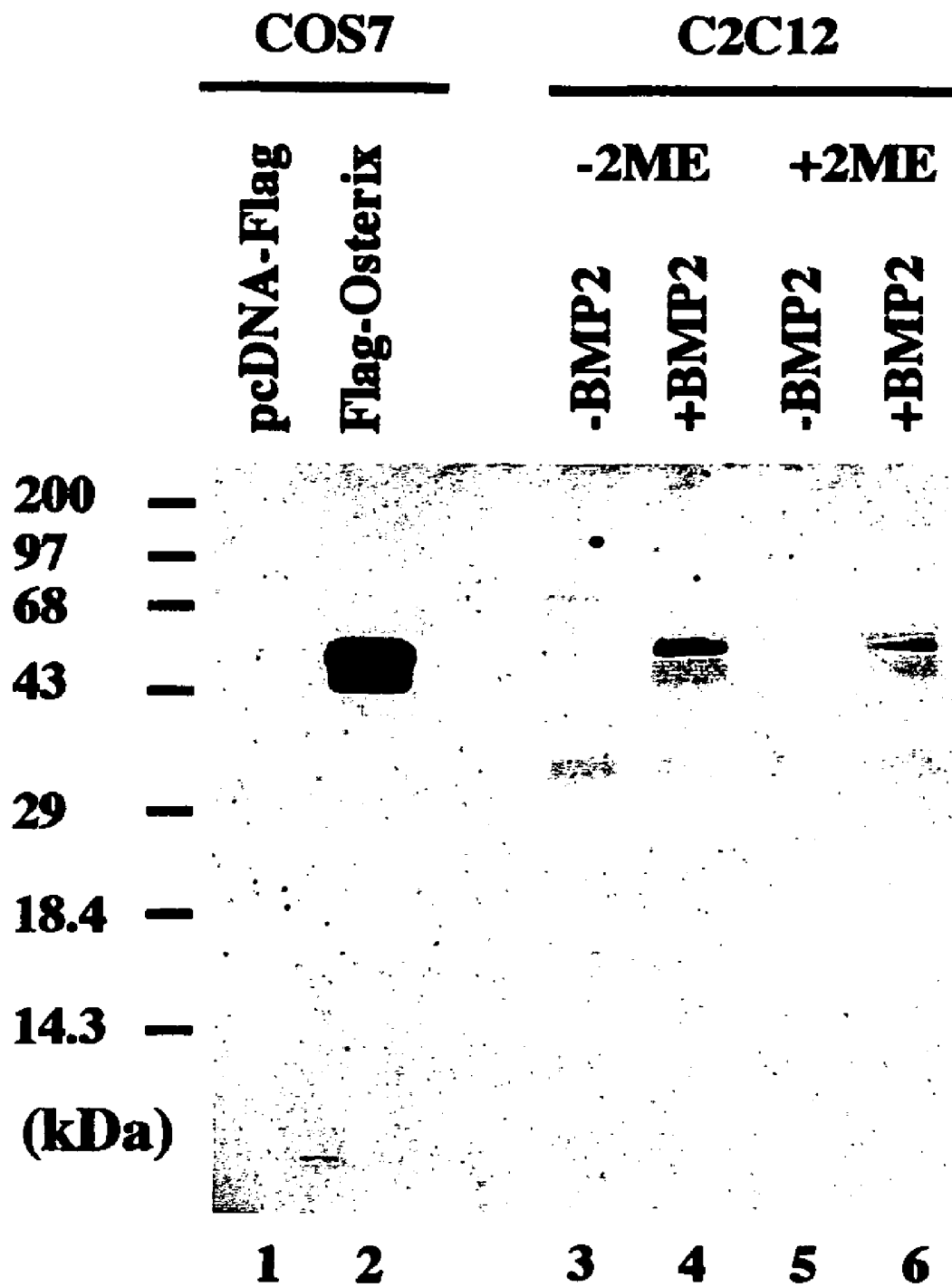
FIG. 3. Identification of endogenous Osterix protein. COS7 cells were transfected with an expression plasmid encoding Flag tagged full-length Osterix. Confluent C2C12 cells were incubated with DMEM containing 5% FBS in the absence or presence of BMP-2 for 24 hours. Antibody against Osterix C-terminal part recognized the endogenous Osterix protein as well as the recombinant Osterix in Western blot.
Figure 5A:
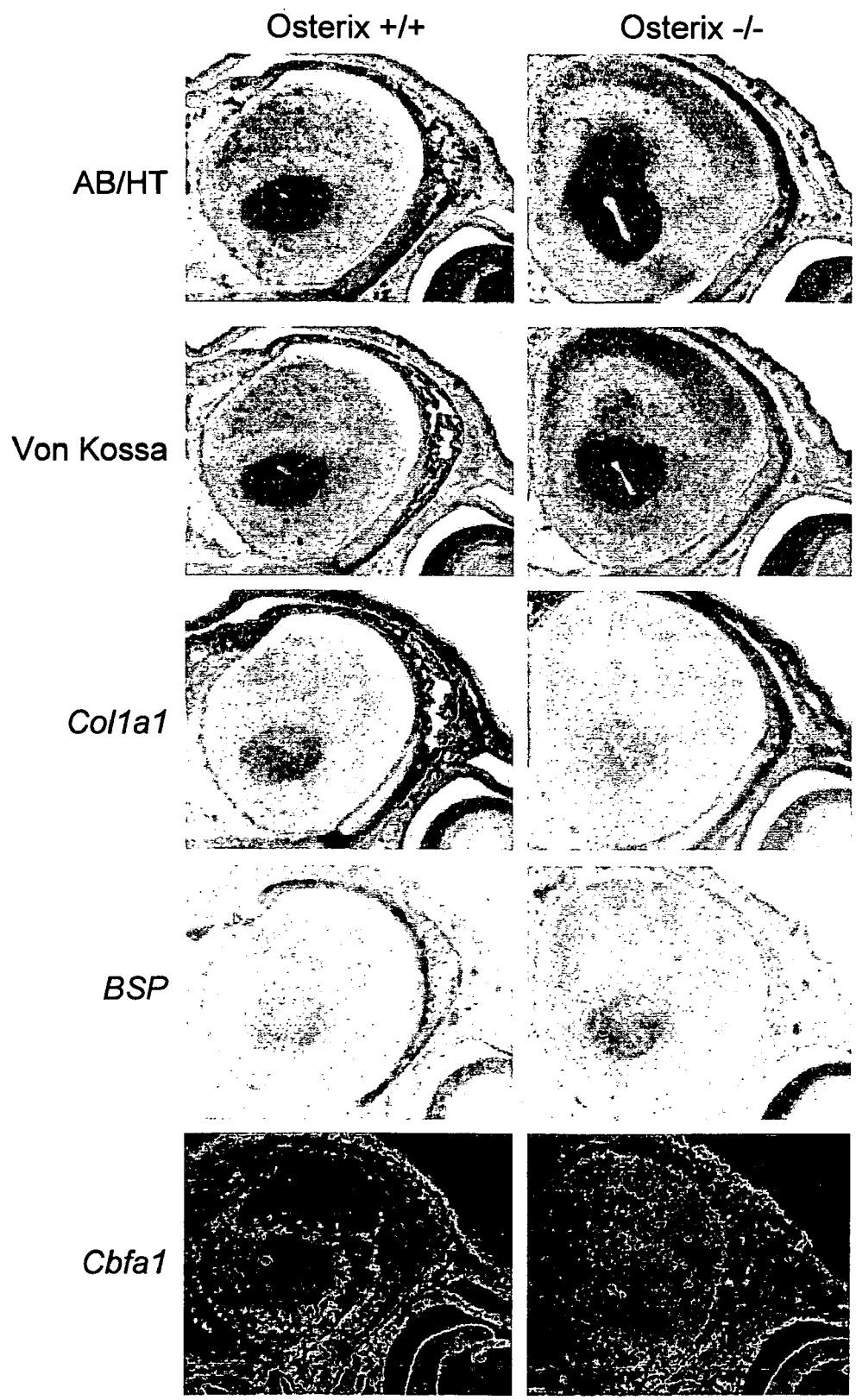
FIG. 5A, FIG. 5B, FIG. 5C and FIG. 5D. Histology and in situ hybridizations of wild type and Osterix$^{-/-}$ mutant mouse embryos at 16.5 days of embryonic development (E16.5).
Figure 5B:
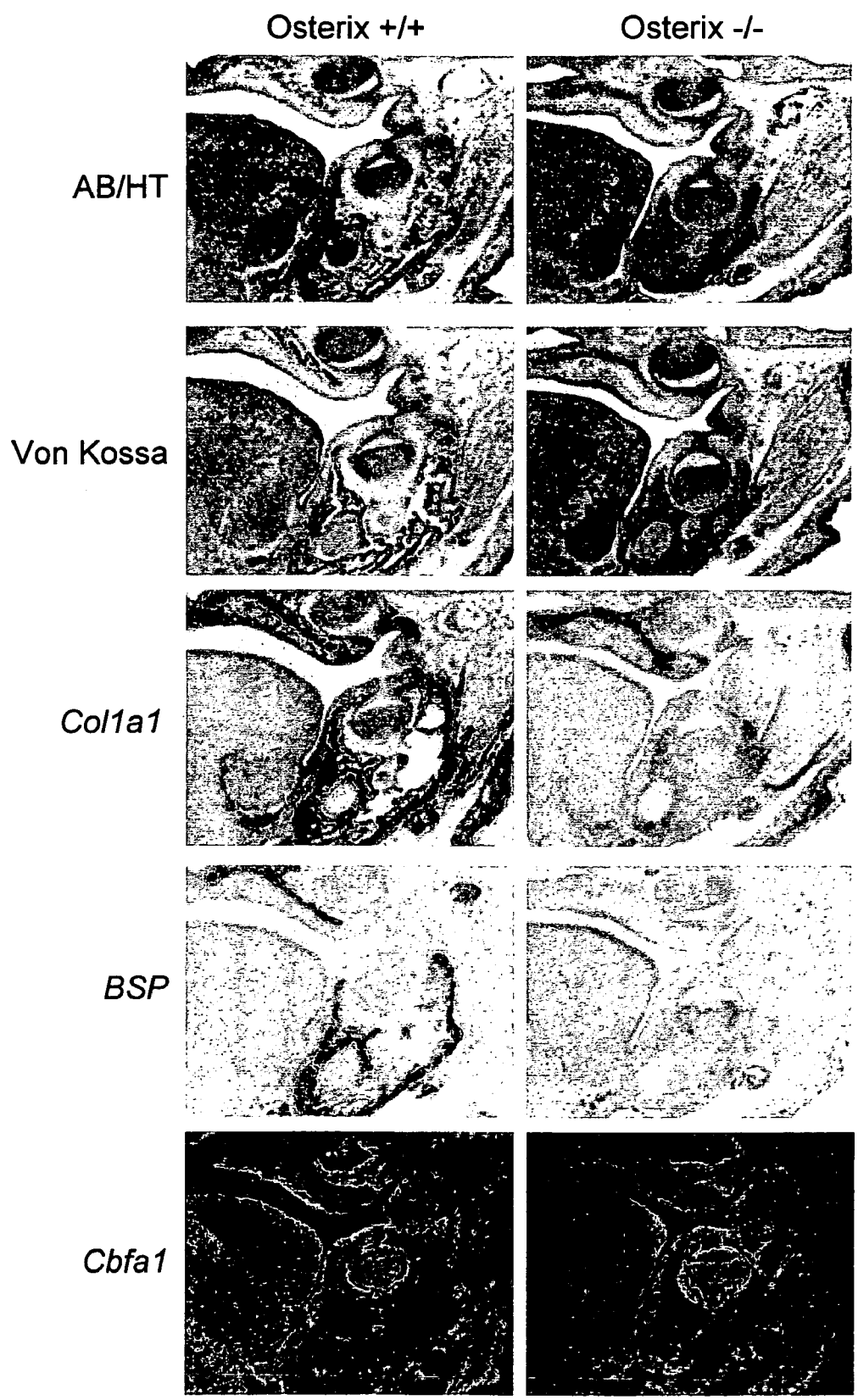
Figure 5C:
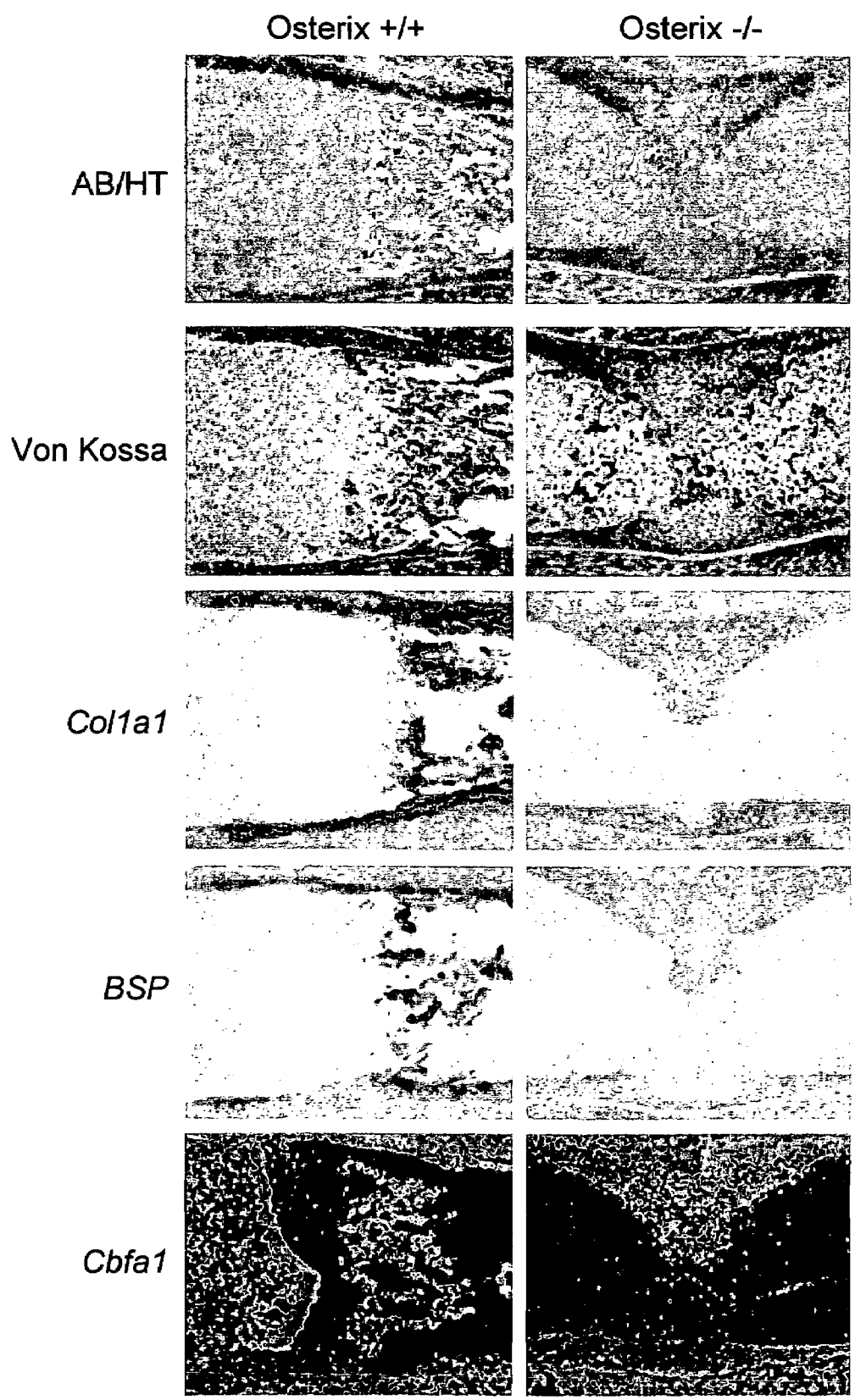
Figure 5D:
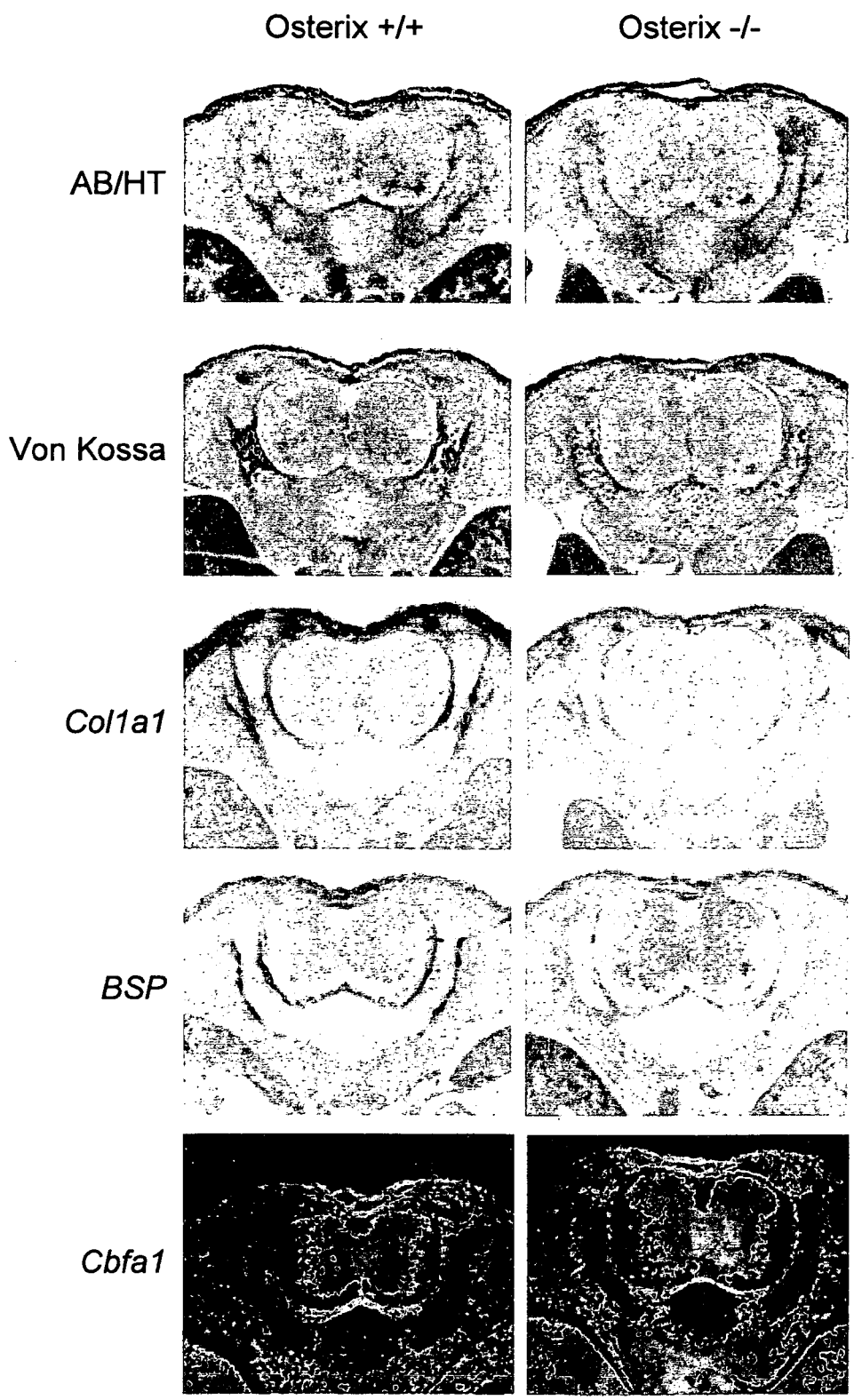

The inventors have generated anti-Osterix antibodies using a peptide located at the carboxy terminal of mouse Osterix. The antibodies recognized a polypeptide with a mobility of approximately 49 kDa present in BMP2-treated C2C12 cells. This polypeptide had the same mobility as the recombinant protein detected after transfection of COS7 cells with a vector expressing the mouse Osterix cDNA (FIG. 3).

As used hereinbelow, the term Osterix should be interpreted to include not only the full length molecule but also isoforms, glycosylated forms as well as non-glycosylated forms of the molecule, and other members of the Osterix family. Different isoforms may be purified from extracts of osteoblast preparation (e.g., BMP2-treated C2C12 line) by immunoprecipitation using polyclonal anti-Osterix antibodies or monoclonal antibodies (MAb) against different domains of Osterix. Different isoforms may also be produced in recombinant forms. For this aim, cDNA encoding each isoform will be expressed in bacteria, yeast cells, insect cells, or mammalian cells and the expressed proteins purified using antibodies against Osterix.

The inventors contemplate that the Osterix proteins and/or polypeptides described herein not only function to control bone formation but that they can also mediate effective recognition and uptake of specific antigens (e.g., carbohydrate moieties or peptide moieties of antigens) to activate the protein and stimulate bone formation. Further, the proteins and/or polypeptides described herein may serve as receptors of soluble molecules (e.g., cytokines, growth factors, chemical mediators); as homing/adhesion/rolling receptors mediating the migration of osteoblasts; as signaling receptors, thereby regulating the function of osteoblasts; and/or as ligands of signaling receptors on osteoblasts, thereby regulating their function. Additionally, the proteins and/or polypeptides of the invention may transduce activation signals into non-osteoblast populations, e.g., chondrocytes, mesenchymal cells such as in teeth, etc., or other cell types, which also recognize Osterix.

B. DNA and RNA Segments for Osterix

1. DNA Segments

Important aspects of the present invention concern isolated DNA segments and recombinant vectors encoding Osterix, and the creation and use of recombinant host cells through the application of DNA technology that express Osterix.

More specifically, the present invention concerns mammalian DNA segments, isolated away from other mammalian genomic DNA segments or total chromosomes. Preferred sources for the Osterix DNA segments of the invention are human gene sequences. In cloning a Osterix sequence of the invention, one may advantageously choose an established osteoblast line. But other sources will be equally appropriate, such as cDNA or genomic libraries including at least some osteoblasts. In particular, the DNA segments of the invention have been found to be isolatable from a BMP2-treated mouse cell line that is normally a progenitor of skeletal muscle cells, termed C2C12 (ATCC # CRL 1772). The DNA segments of the invention are capable of conferring Osterix-like activity or properties, such as defined herein below, to a recombinant host cell when incorporated into the recombinant host cell.

As used herein, the term "DNA segment" refers to a DNA molecule that has been isolated substantially free of total genomic DNA and chromosomes of a particular species. Therefore, a DNA segment encoding Osterix refers to a DNA segment that contains Osterix coding sequences yet is isolated away from, or purified free from, total genomic DNA of tissues known to contain relatively large numbers of osteoblasts, or of the BMP2-treated C2C12 line. Included within the term "DNA segment", are DNA segments and smaller fragments of such segments, and also recombinant vectors, including, for example, plasmids, cosmids, phage, viruses, and the like.

Similarly, a DNA segment comprising an isolated or purified Osterix gene refers to a DNA segment including Osterix coding sequences and, in certain aspects, regulatory sequences, isolated substantially away from other naturally occurring genes or protein encoding sequences. In this respect, the term "gene" is used for simplicity to refer to a DNA segment that encodes a polypeptide or a functional protein. As will be understood by those in the art, this functional term includes both genomic sequences, cDNA sequences and smaller engineered gene segments that express, or may be adapted to express, proteins, polypeptides or peptides. "Isolated substantially away from other coding sequences" means that the gene of interest, in this case Osterix, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode an Osterix protein or polypeptide that includes within its amino acid sequence an amino acid sequence in accordance with SEQ ID NO:2, corresponding to human or mammalian Osterix.

In certain embodiments, the invention concerns isolated DNA segments and recombinant vectors that encode a protein or polypeptide that includes within its amino acid sequence an amino acid sequence essentially as set forth in SEQ ID NO:2. Naturally, where the DNA segment or vector encodes a full length Osterix protein, or is intended for use in expressing the Osterix protein, the most preferred sequences are those that are essentially as set forth in SEQ ID NO: 2 and that encodes a protein that retains osteoblast/osteoblast transcription activity, e.g., as may be determined by any suitable assay, as disclosed herein.

The term "a sequence essentially as set forth in SEQ ID NO:2" means that the sequence substantially corresponds to a portion of SEQ ID NO:2 and has relatively few amino acids that are not identical to, or a biologically functional equivalent of, the amino acids of SEQ ID NO: 2. The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of SEQ ID NO:2 will be sequences that are "essentially as set forth in SEQ ID NO:2."

In certain other embodiments, the invention concerns isolated DNA segments and recombinant vectors that include within their sequence a nucleic acid sequence essentially as set forth in SEQ ID NO:1. The term "essentially as set forth in SEQ ID NO:1" is used in the same sense as described above and means that the nucleic acid sequence substantially corresponds to a portion of SEQ ID NO:1 and has relatively few codons that are not identical, or functionally equivalent, to the codons of SEQ ID NO:1. Again, DNA segments that encode proteins exhibiting osteoblast transcription activity will be most preferred. The term "functionally equivalent codon" is used herein to refer to codons that encode the same amino acid, such as the six codons for arginine or serine, and also refers to codons that encode biologically equivalent amino acids. Table 1 sets forth the amino acids and codons which encode each amino acid.

TABLE 1

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

It is within the scope of the invention in certain aspects that high level protein production may be achieved by reducing criteria for osteoblast differentiation. In certain embodiments it is within the invention to produce proteins lacking activity. Such proteins might be useful in very high volume to raise antibodies to the protein. In other aspects, activity is desired and the detailed examples explain preferred methods for obtaining proteins and/or polypeptides retaining osteoblast differentiation activity.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of osteoblast differentiation activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have between about 65% and about 80%; or more preferably, between about 80% and about 90%; or even more preferably, between about 90% and about 99% of nucleotides that are identical to the nucleotides of SEQ ID NO:1 will be sequences that are "essentially as set forth in SEQ ID NO:1". Sequences that are essentially the same as those set forth in SEQ ID NO:1 may also be functionally defined as sequences that are capable of hybridizing to a nucleic acid segment containing the complement of SEQ ID NO:1 under relatively stringent conditions. Suitable relatively stringent hybridization conditions will be well known to those of skill in the art and are clearly set forth herein, for example conditions such as relatively low salt and/or high temperature conditions, such as provided by 0.02M–0.15M NaCl at temperatures of 50° C. to 70° C., for applications requiring high selectivity. Such relatively stringent conditions tolerate little, if any, mismatch between the probe and the template or target strand, and would be particularly suitable for isolating Osterix genes.

For example, the expression of Osterix mRNA in mouse tissues (e.g., osteoblasts and secondary ossification centers) and cell lines (e.g., C2C12 line) was readily detectable with full-length cDNA probes (i.e., SEQ ID NO:1) in northern blotting under a high stringent condition, 0.12 M NaCl at 65° C. Likewise, Osterix mRNA were both detectable by RT-PCR™. These results indicate that mouse Osterix mRNA are detectable with nucleotide sequences, either as cDNA probes or primers, that are identical to or contain the nucleotides of SEQ ID NO:1. When Osterix antibodies were added to transcription studies, DNA binding was specifically inhibited (FIG. 4A and FIG. 4B). It was also shown that recombinant Osterix binds to a consensus SP1 oligonucleotide. The proline-rich segment between amino acid residues 27 to 192 had a potent transcriptional activation activity. Thus, Osterix has exhibited the principle characteristics of a transcription factor. Osterix has further been shown to be a nuclear protein.

Figure 8A:
FIG. 8A and FIG. 8B. Chromosomal localization of the mouse Osterix gene (SEQ ID No:1) and mapping data for the Osterix gene (SEQ ID NO:1).
Figure 8B:
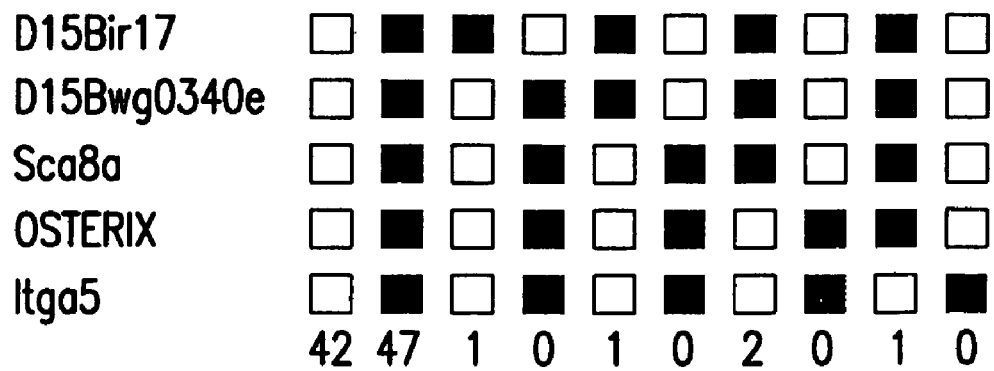

A panel of genomic DNAs obtained from backcross mice were used to map the gene for Osterix on the mouse genome. The backcross animals were generated from a cross between (C57BL/6J×M Spretus) mice and C57BL/6J mice provided by the Jackson Laboratory. The gene was shown to map to chromosome 15 in mice in a region that is syntenic with chromosome 12q13 in humans (FIG. 8A and FIG. 8B).

Naturally, the present invention also encompasses DNA segments that are complementary, or essentially complementary, to the sequence set forth in SEQ ID NO:1. Nucleic acid sequences that are "complementary" are those that are capable of base-pairing according to the standard Watson-Crick complementary rules. That is, that the larger purines will always base pair with the smaller pyrimidines to form only combinations of Guanine paired with Cytosine (G:C) and Adenine paired with either Thymine (A:T), in the case of DNA, or Adenine paired with Uracil (A:U) in the case of RNA.

As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 under relatively stringent conditions such as those described herein. As such, these complementary sequences are substantially complementary over their entire length and have very few base mismatches. For example, nucleic acid sequences of six bases in length may be termed complementary when they hybridize at five out of six positions with only a single mismatch. Naturally, nucleic acid sequences which are "completely complementary" will be nucleic acid sequences which are entirely complementary throughout their entire length and have no base mismatches. Equivalents will show transcriptional activity. This is one feature which will distinguish it from non-Osterix nucleic acid sequences.

Antisense constructs are oligo- or polynucleotides comprising complementary nucleotides to the coding segment of a DNA molecule, such as a gene or cDNA, including both the exons, introns and exon:intron boundaries of a gene. Antisense molecules are designed to inhibit the transcription, translation or both, of a given gene or construct, such that the levels of the resultant protein product are reduced or diminished. Antisense RNA constructs, or DNA encoding such antisense RNAs, may be employed to inhibit gene transcription or translation or both within a host cell, either in vitro or in vivo, such as within a host animal, including a human subject.

2. Hybridization Probes

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. In addition to their use in directing the expression of the Osterix protein, the nucleic acid sequences disclosed herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous sequence of SEQ ID NO:1, will find particular utility. Longer contiguous identical or complementary sequences, e.g., those of about 14, 15, 16, 17, 20, 30, 40, 50, 100, 200, 500, 1000, 1100, 1200, 1248, 1300, 1400, 1500, 1600, 1700, 1800, 1900, 2000, 2100, 2200, 2300, 2400, 2500, 2600, 2700, 2800, 2900 to 2950 nucleotides (including all intermediate lengths), and even up to full length sequences of about 2.9 kb will also be of use in certain embodiments.

It will be readily understood that "intermediate lengths", in this context, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002 and the like.

The ability of such nucleic acid probes to specifically hybridize to Osterix encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10, 20, 30, 50, or even of 100–200 nucleotides or so, identical or complementary to SEQ ID NO:1, are particularly contemplated as hybridization probes for use in, e.g., Southern and northern blotting. This would allow Osterix structural or regulatory genes to be analyzed, both in tissues and cells. The inventors have generated a human DNA for Osterix. The deduced amino acid sequence of this human cDNA is 95 percent identical to the mouse sequence (FIG. 10). The inventors have also identified the sequence of genomic DNA for human Osterix. The total size of fragment, as well as the size of the complementary stretch(es), will ultimately depend on the intended use or application of the particular nucleic acid segment. Smaller fragments will generally find use in hybridization embodiments, wherein the length of the contiguous complementary region may be varied, such as between about 10 and about 100 nucleotides, but larger contiguous complementary stretches of up to about 2.9 kb may be used, according to the length complementary sequences one wishes to detect.

The use of a hybridization probe of about 10–14 nucleotides in length allows the formation of a duplex molecule that is both stable and selective. Molecules having contiguous complementary sequences over stretches greater than 10 bases in length are generally preferred, though, in order to increase stability and selectivity of the hybrid, and thereby improve the quality and degree of specific hybrid molecules obtained, one will generally prefer to design nucleic acid molecules having gene-complementary stretches of 15 to 20 contiguous nucleotides, or even longer where desired.

Hybridization probes may be selected from any portion of any of the sequences disclosed herein. All that is required is to review the sequence set forth in SEQ ID NO:1 and to select any continuous portion of the sequence, from about 10 nucleotides in length up to and including the full length sequence, that one wishes to utilize as a probe or primer. The choice of probe and primer sequences may be governed by various factors, such as, by way of example only, one may wish to employ primers from towards the termini of the total sequence, or from the ends of the functional domain-encoding sequences, in order to amplify further DNA; one may employ probes corresponding to the entire DNA, or to the zinc finger region, or to the proline-rich sequence to clone Osterix-type genes from other species or to clone further Osterix-like or homologous genes from any species including human; and one may employ wild-type and mutant probes or primers with sequences centered around the zinc finger or proline-rich sequence to screen DNA samples for Osterix. Moreover, one may employ probes or primers with sequences centered around the different Osterix isoforms.

The process of selecting and preparing a nucleic acid segment that includes a contiguous sequence from within SEQ ID NO:1 may alternatively be described as preparing a nucleic acid fragment. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 and U.S. Pat. No. 4,682,195 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of Osterix genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by 0.02M–0.15M NaCl at temperatures of 50° C. to 70° C. Such selective conditions tolerate little, if any, mismatch between the probe and the template or target strand, and would be particularly suitable for isolating Osterix genes.

Of course, for some applications, for example, where one desires to prepare mutants employing a mutant primer strand hybridized to an underlying template or where one seeks to isolate Osterix encoding sequences from related species, functional equivalents, or the like, less stringent hybridization conditions will typically be needed in order to allow formation of the heteroduplex. In these circumstances, one may desire to employ conditions such as 0.15M–1.0M salt, at temperatures ranging from 20° C. to 55° C. Cross-hybridizing species can thereby be readily identified as positively hybridizing signals with respect to control hybridizations. In fact, the inventors have been able to detect a human equivalent for mouse Osterix by Southern hybridization of human cDNA with a sequence of mouse Osterix (SEQ ID NO:6) under a low stringency condition (1M NaCl, 30–45% formamide, 10% dextran sulfate, at 37° C). In any case, it is generally appreciated that conditions can be rendered more stringent by decreasing NaCl concentrations or by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

It will also be understood that this invention is not limited to the particular nucleic acid and amino acid sequences of SEQ ID NO:1 and SEQ ID NO: 2. Recombinant vectors and isolated DNA segments may therefore variously include the Osterix coding regions themselves, coding regions bearing selected alterations or modifications in the basic coding region, or they may encode larger polypeptides that nevertheless include Osterix coding regions or may encode biologically functional equivalent proteins or polypeptides that have variant amino acids sequences.

The DNA segments of the present invention encompass biologically functional equivalent Osterix proteins and polypeptides. Such sequences may arise as a consequence of codon redundancy and functional equivalency that are known to occur naturally within nucleic acid sequences and the proteins thus encoded. Alternatively, functionally equivalent proteins or polypeptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test Osterix mutants in order to examine transcriptional activity at the molecular level.

If desired, one may also prepare fusion proteins and polypeptides, e.g., where the Osterix coding regions are aligned within the same expression unit with other proteins or polypeptides having desired functions, such as for purification or immunodetection purposes (e.g., proteins that may be purified by affinity chromatography or identified by enzyme label coding regions, respectively).

3. Recombinant Vectors and Protein Expression

Recombinant vectors form important further aspects of the present invention. Particularly useful vectors are contemplated to be those vectors in which the coding portion of the DNA segment, whether encoding a full length protein or smaller polypeptide, is positioned under the control of a promoter. The promoter may be in the form of the promoter that is naturally associated with an Osterix gene, e.g., in osteoblasts as may be obtained by isolating the 5' non-coding sequences located upstream of the coding segment or exon, for example, using recombinant cloning and/or PCR™ technology, in connection with the compositions disclosed herein (PCR™ technology is disclosed in U.S. Pat. No. 4,683,202 and U.S. Pat. No. 4,682,195, each incorporated herein by reference).

a. Promoters and Enhancers

The promoters and enhancers that control the transcription of protein encoding genes in mammalian cells are composed of multiple genetic elements. The cellular machinery is able to gather and integrate the regulatory information conveyed by each element, allowing different genes to evolve distinct, often complex patterns of transcriptional regulation.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator proteins. At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either cooperatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation.

Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities. They have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way.

Provided in Tables 2 and 3 are lists of viral promoters, cellular promoters/enhancers and inducible promoters/enhancers that could be used in combination with the present invention. Additionally any promoter/enhancer combination (as per the Eukaryotic Promoter Data Base EPDB) could also be used to drive expression of Osterix or antisense constructs.

TABLE 2

REPRESENTATIVE PROMOTERS

| PROMOTERS | REFERENCES |
|---|---|
| Immunoglobulin Heavy Chain | Hanerli et al., 1983; Gilles et al., 1983; Grosschedl and Baltimore, 1985; Atchinson and Perry, 1986, 1987; Imler et al., 1987; Weinberger et al., 1988; Kiledjian et al., 1988; Porton et al., 1990 |

TABLE 2-continued

REPRESENTATIVE PROMOTERS

| PROMOTERS | REFERENCES |
|---|---|
| Immunoglobulin Light Chain | Queen and Baltimore, 1983; Picard and Schaffner, 1984 |
| T-Cell Receptor | Luria et al., 1987, Winoto and Baltimore, 1989; Redondo et al., 1990 |
| HLA DQ a and DQ β | Sullivan and Peterlin, 1987 |
| β-Interferon | Goodbourn et al., 1986; Fujita et al., 1987; Goodbourn and Maniatis, 1985 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al., 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987, Tronche et al., 1989, 1990 |
| a-Fetoprotein | Godbout et al., 1988; Campere and Tilghman, 1989 |
| t-Globin | Bodine and Ley, 1987; Perez-Stable and Constantini, 1990 |
| β-Globin | Trudel and Constantini, 1987 |
| e-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| $a_1$-Antitrypain | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1975; Vasseur et al., 1980; Katinka et al., 1980, 1981; Tyndell et al., 1981; Dandolo et al., 1983; deVilliers et al., 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a,b, 1988; Bosze et al., 1986; Miksicek et al., 1986; Celander and Haseltine, 1987; Thiesen et al., 1988; Celander et al., 1988; Chol et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987, Stephens and Hentschel, 1987; Glue et al., 1988 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immunodeficiency Virus | Muesing et al., 1987; Hauber and Cullan, 1988; Jakobovits et al., 1988; Feng and Holland, 1988; Takebe et al., 1988; Rowen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia virus | Holbrook et al., 1987; Quinn et al., 1989 |

TABLE 3

ENHANCERS AND INDUCERS

| | Inducer | References |
|---|---|---|
| MT II | Phorbol Ester (TFA) Heavy metals | Palmiter et al., 1982; Haslinger and Karin, 1985; Searle et al., 1985; Stuart et al., 1985; Imagawa et al., 1987; Karin ®, 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Lee et al., 1984; Fonta et al., 1985; Sakai et al., 1986 |
| β-Interferon | Poly(rI)X Poly(rc) | Tavernier et al., 1983 |
| Adenovirus 5 E2 | Ela | Imperiale and Nevins, 1984 |
| Collagenase | Phorbol Ester (TPA) | Angle et al., 1987a |
| Stromelysin | Phorbol Ester (TPA) | Angle et al., 1987b |
| SV40 | Phorbol Ester (TFA) | Angel et al., 1987b |
| Murine MX Gene | Interferon, Newcastle Disease Virus | |

TABLE 3-continued

ENHANCERS AND INDUCERS

| | Inducer | References |
|---|---|---|
| GRP78 Gene | A23187 | Resendez et al., 1988 |
| a-2-Macroglobulin | IL-6 | Kunz et al., 1989 |
| Vimentin | Serum | Rittling et al., 1989 |
| MHC Class I Gene H-2kb | Interferon | Blanar et al., 1989 |
| HSP70 | Ela, SV40 Large T Antigen | Taylor et al., 1989; Taylor and Kingston, 1990a,b |
| Proliferin | Phorbol Ester-TPA | Mordacq and Linzer, 1989 |
| Tumor Necrosis Factor | FMA | Hensel et al., 1989 |
| Thyroid Stimulating Hormone a Gene | Thyroid Hormone | Chatterjee et al., 1989 |

It is understood in the art that to bring a coding sequence under the control of a promoter, one positions the 5' end of the transcription initiation site of the transcriptional reading frame of the protein between about 1 and about 50 nucleotides "downstream" of (i.e., 3' of) the chosen promoter. In addition, where eukaryotic expression is contemplated, one will also typically desire to incorporate into the transcriptional unit which includes the cotransporter protein, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

There are two basic procedures for studying the in vivo expression of cloned genes and their promoters. In transient systems, the gene of interest is introduced into a population of cultured cells, and its activity is assayed within a few hours to a few days. The original transient expression studies utilized encapsidated SV40 recombinants. Although only a small fraction of the cells take up and express the recombinant genes, transcription of the foreign gene can be readily detected. Alternatively, if the promoter (control region) of the recombinant gene is under study, the promoter and enhancer can be cloned with the coding region of a gene such as Herpes Simplex thymidine kinase (tk), *E. coli* chloramphenicol acetyltransferase (CAT), or luciferase (Luc). The activity of the promoter can be monitored by an assay for the presence of the appropriate gene product.

The second method for studying cloned genes and their control regions is stable transfection. Stable transfection is the preferred method for obtaining moderate expression levels from a transfected gene in a long term continuous culture. In this method the recombinant DNA molecule is introduced by DNA-mediated gene transfer techniques via viral infection. Identification of the recombinant stable transfectant among the population of untransformed cells requires a change in phenotype. Usually the inclusion of a drug selection marker aids in the discovery and selection of the stable transformants. Plasmids that are suitable for subcloning an expression cassette containing the target sequence and any of the promoter/enhancer combinations listed are well known to those of skill in the art. Such plasmids containing the target sequence and promoter/enhancer can be used in a stable transfection protocol or transient transfection procedure.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with an Osterix gene in its natural environment. Such promoters may include CMV, SV40, RSV, LacZ, LTR, TK, POLH, and MMTV or other promoters normally associated with other genes, and/or promoters isolated from any other bacterial, viral, eukaryotic, or mammalian cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al (1989). The promoters employed may be constitutive, or inducible, and can be used under the appropriate conditions to direct high level expression of the introduced DNA segment, such as is advantageous in the large-scale production of recombinant proteins or polypeptides. Appropriate promoter systems contemplated for use in high-level expression include, but are not limited to, CMV and SV40.

b. Expression Vectors

As mentioned above, in connection with expression embodiments to prepare recombinant Osterix proteins and polypeptides, it is contemplated that longer DNA segments will most often be used, with DNA segments encoding the entire Osterix protein being most preferred. However, it will be appreciated that the use of shorter DNA segments to direct the expression of Osterix polypeptides or epitopic core regions, such as may be used to generate anti-Osterix antibodies, also falls within the scope of the invention.

DNA segments that encode polypeptide antigens from about 15 to about 50 amino acids in length, or more preferably, from about 15 to about 30 amino acids in length are contemplated to be particularly useful. The polypeptides may, of course, be of any length in this range, such as 16, 17, 18, 19 or 20 amino acids in length. This is the meaning of "about" in about 15, about 20, about 25, about 30, about 35, about 40, about 45 or about 50 amino acids in length, with "about", in this one context meaning a range of from 1 to 4 amino acids longer or shorter than the stated length, with 14 or 15 or so still being the minimum length. DNA segments encoding polypeptides will generally have a minimum coding length in the order of about 45 to about 150, or to about 90 nucleotides. DNA segments encoding full length proteins may have a minimum coding length in the order of about 128 nucleotides for a protein in accordance with SEQ ID NO:2.

Turning to the expression of the Osterix protein or polypeptides of the invention, once a suitable (full length if desired) clone or clones have been obtained, whether they be cDNA based or genomic, one may proceed to prepare an expression system for the recombinant preparation of Osterix. The engineering of DNA segment(s) for expression in a prokaryotic or eukaryotic system may be performed by techniques generally known to those of skill in recombinant expression. It is believed that virtually any expression system may be employed in the expression of Osterix.

It is proposed that transformation of host cells with DNA segments encoding the Osterix protein will provide a convenient means for obtaining active Osterix. However, separate expression followed by reconstitution is also certainly within the scope of the invention.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired.

In addition, it is possible to express partial sequences, e.g., for the generation of antibodies against discrete portions of a gene product, even when the entire sequence of that gene product remains unknown. As noted herein, computer programs are available to aid in the selection of regions which have potential immunologic significance. For example, software capable of carrying out this analysis is readily available commercially, for example MacVector (IBI, New Haven, Conn.). The software typically uses standard algorithms such as the Kyte/Doolittle or Hopp/Woods methods for locating hydrophilic sequences which are characteristically found on the surface of proteins and are, therefore, likely to act as antigenic determinants.

In the recombinant production of large amounts of proteins or polypeptides, it may be advisable to analyze the protein to detect putative transmembrane sequences. Such sequences are typically very hydrophobic and are readily detected by the use of standard sequence analysis software, such as MacVector (IBI, New Haven, Conn.). The presence of transmembrane sequences is often deleterious when a recombinant protein is synthesized in many expression systems, especially E. Coli, as it leads to the production of insoluble aggregates that are difficult to renature into the native conformation of the protein. Deletion of transmembrane sequences typically does not significantly alter the conformation of the remaining protein structure.

Moreover, transmembrane sequences, being by definition embedded within a membrane, are inaccessible. Antibodies to these sequences will not, therefore, generally prove useful in in vivo or in situ studies. Deletion of transmembrane-encoding sequences from the genes used for expression can be achieved by standard techniques. For example, fortuitously-placed restriction enzyme sites can be used to excise the desired gene fragment, or PCR™-type amplification can be used to amplify only the desired part of the gene.

As used herein, the terms "engineered" and "recombinant" cells are intended to refer to a cell into which an exogenous DNA segment or gene, such as a cDNA or gene encoding an Osterix protein or polypeptide has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

To express a recombinant Osterix protein or polypeptide, whether mutant or wild-type, in accordance with the present invention one would prepare an expression vector that comprises an Osterix protein or polypeptide-encoding nucleic acid segment under the control of one or more promoters. To bring a coding sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or polypeptide expression in a variety of host-expression systems. Cell types available for expression include, but are not limited to, bacteria, such as E. coli and B. subtilis transformed with recombinant bacteriophage DNA, plasmid DNA or cosmid DNA expression vectors.

Certain examples of prokaryotic hosts are E. coli strain RR1, E. coli LE392, E. coli B, E. coli X 1776 (ATCC No. 31537) as well as E. coli W3110 (F-, lambda-, prototrophic, ATCC No. 273325); bacilli such as Bacillus subtilis; and other enterobacteriaceae such as Salmonella typhimurium, Serratia marcescens, and various Pseudomonas species.

In general, plasmid vectors containing replicon and control sequences which are derived from species compatible with the host cell are used in connection with these hosts. The vector ordinarily carries a replication origin, as well as marking sequences which are capable of providing phenotypic selection in transformed cells. For example, E. coli is often transformed using pBR322, a plasmid derived from an E. coli species. pBR322 contains genes for ampicillin and tetracycline resistance and thus provides means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as E. coli LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, mannose binding protein (MBP) and the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

The following details concerning recombinant protein production in bacterial cells, such as E. coli, are obtained from exemplary information on recombinant protein production in general, the adaptation of which to a particular recombinant expression system will be known to those of skill in the art.

Bacterial cells, for example, *E. coli,* containing the expression vector are grown in any of a number of suitable media, for example, LB. The expression of the recombinant protein may be induced, e.g., by adding IPTG to the media or by switching incubation to a higher temperature. After culturing the bacteria for a further period, generally of between 2 and 24 hours, the cells are collected by centrifugation and washed to remove residual media.

The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant protein is expressed in the inclusion bodies, as is the case in many instances, these can be washed in any of several solutions to remove some of the contaminating host proteins, then solubilized in solutions containing high concentrations of urea (e.g. 8M) or chaotropic agents such as guanidine hydrochloride in the presence of reducing agents, such as β-mercaptoethanol or DTT (dithiothreitol).

Under some circumstances, it may be advantageous to incubate the protein for several hours under conditions suitable for the protein to undergo a refolding process into a conformation which more closely resembles that of the native protein. Such conditions generally include low protein concentrations, less than 500 μg/ml, low levels of reducing agent, concentrations of urea less than 2 M and often the presence of reagents such as a mixture of reduced and oxidized glutathione which facilitate the interchange of disulfide bonds within the protein molecule.

The refolding process can be monitored, for example, by SDS-PAGE, or with antibodies specific for the native molecule (which can be obtained from animals immunized with the native molecule or smaller quantities of recombinant protein).

Following refolding, the protein can then be purified further and separated from the refolding mixture by chromatography on any of several supports including ion exchange resins, gel permeation resins or on a variety of affinity columns.

In addition to prokaryotes, eukaryotic microbes, such as yeast cultures, may also be used. *Saccharomyces cerevisiae,* or common baker's yeast, is the most commonly used among eukaryotic microorganisms, although a number of other strains are commonly available. For expression in *Saccharomyces,* the plasmid YRp7, for example, is commonly used (Stinchcomb et al., 1979; Kingsman et al., 1979; Tschemper et al., 1980). This plasmid already contains the trp1 gene which provides a selection marker for a mutant strain of yeast lacking the ability to grow in tryptophan, for example ATCC No. 44076 or PEP4–1 (Jones, 1977). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more Osterix protein or polypeptide coding sequences.

In a useful insect system, *Autograph californica* nuclear polyhidrosis virus (AcNPV) is used as a vector to express foreign genes. The virus grows in *Spodoptera frugiperda* cells. The Osterix protein or polypeptide coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051 (Smith)).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein.

Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for glycosylation, intracellular transport, high expression and DNA replication may be used if desired, with a cell that allows for high expression being preferred.

Expression vectors for use in mammalian such cells ordinarily include an origin of replication (as necessary), a promoter located in front of the gene to be expressed, along with any necessary ribosome binding sites, RNA splice sites, polyadenylation site, and transcriptional terminator sequences. The origin of replication may be obtained from either construction of the vector to include an exogenous origin, such as may be derived from SV40 or other viral (e.g., Polyoma, Adeno, VSV, BPV) source, or may be obtained from the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired Osterix gene sequence, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication. Further, it is also possible and often desirable to utilize promoter or control sequences normally associated with the desired gene sequence, provided such control sequences are compatible with the host cell systems.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing Osterix proteins in infected hosts.

Specific initiation signals may also be required for efficient translation of Osterix coding sequences. These signals include the ATG initiation codon and adjacent Kosak sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators (Bittner et al., 1987).

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination codon of the protein at a position prior to transcription termination.

For long-term, high-yield production of recombinant Osterix proteins, stable expression is preferred. For example, cell lines that stably express constructs encoding Osterix proteins or polypeptides may be engineered. Rather than using expression vectors that contain viral origins of replication, host cells can be transformed with vectors controlled by appropriate expression control elements (e.g., promoter, enhancer, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited to, the herpes simplex virus thymidine kinase (Wigler et al., 1977), hypoxanthine-guanine phosphoribosyltransferase (Szybalska et al., 1962) and adenine phosphoribosyltransferase genes (Lowry et al., 1980), in tk-, hgprt- or aprt- cells, respectively. Also, antimetabolite resistance can be used as the basis of selection for dhfr, that confers resistance to methotrexate (Wigler et al., 1980; O'Hare et al., 1981); gpt, that confers resistance to mycophenolic acid (Mulligan et al., 1981); neo, that confers resistance to the aminoglycoside G-418 (Colberre-Garapin et al., 1981); and hygro, that confers resistance to hygromycin (Santerre et al., 1984).

It is contemplated that the Osterix of the invention may be "overexpressed", i.e., expressed in increased levels relative to its natural expression in osteoblast cells, or even relative to the expression of other proteins in the recombinant host cell. Such overexpression may be assessed by a variety of methods, including radio-labeling and/or protein purification. However, direct methods are preferred, for example, those involving SDS/PAGE and protein staining or western blotting, followed by quantitative analyses, such as densitometric scanning of the resultant gel or blot. A specific increase in the level of the recombinant protein or polypeptide in comparison to the level in natural osteoblasts is indicative of overexpression, as is a relative abundance of the specific protein in relation to the other proteins produced by the host cell and, e.g., visible on a gel.

Currently preferred methods for producing Osterix proteins or polypeptides by recombinant expression are described herein. For example, Example 5 provides that Osterix proteins or polypeptides may be obtained by recombinant expression in *E. coli*.

C. Osterix Proteins or Polypeptides

1. Purification of Osterix Proteins

Further aspects of the present invention concern the purification, and in particular embodiments, the substantial purification, of an Osterix protein or polypeptide. The term "purified protein" as used herein, is intended to refer to an Osterix composition, isolatable from osteoblasts, C2C12 cells, or recombinant host cells, wherein the Osterix is purified to any degree relative to its naturally-obtainable state, i.e., in this case, relative to its purity within a osteoblasts or C2C12 cell extract. A purified Osterix protein therefore also refers to a protein, free from the environment in which it may naturally occur in intact cells.

It is contemplated that the purified Osterix proteins or polypeptides of the invention will generally possess Osterix activity. That is, they will have the capacity to bind to putative ligands introduced to osteoblasts and promote osteoblast differentiation and/or bone formation.

Generally, "purified" will refer to an Osterix composition which has been subjected to fractionation to remove various non-Osterix components such as other cell components. Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques. A specific example presented herein is the purification of Osterix using immunoprecipitation with anti-Osterix antibodies.

Where the term "substantially purified" is used, this will refer to a composition in which Osterix forms the major component of the composition, such as constituting about 50% of the proteins in the composition or more. In preferred embodiments, a substantially purified protein will constitute more than 60% of the proteins in the composition.

A polypeptide or protein that is "purified to homogeneity," as applied to the present invention, means that the polypeptide or protein has a level of purity where the polypeptide or protein is substantially free from other proteins and biological components. For example, a purified polypeptide or protein will often be sufficiently free of other protein components so that degradative sequencing may be performed successfully.

Various methods for quantifying the degree of purification of the Osterix protein will be known to those of skill in the art in light of the present disclosure. These include, for example, determining the specific activity of an active fraction, or assessing the number of polypeptides within a fraction by gel electrophoresis. Assessing the number of polypeptides within a fraction by SDS/PAGE analysis will often be preferred in the context of the present invention, e.g., in assessing protein purity.

A preferred method for assessing the purity of an Osterix fraction is to calculate the specific activity of the fraction, to compare it to the specific activity of the initial osteoblast cell or C2C12 extract, and to thus calculate the degree of purity, herein assessed by a "-fold purification number".

The actual units used to represent the amount of transcriptional activity will, of course, be dependent upon the particular assay technique chosen to follow the purification. As discussed above, the present inventors prefer to use SDS-PAGE and western blotting to examine the relative amounts of Osterix proteins. For this purpose, it is preferred to use polyclonal antibodies against Osterix, antibodies that recognize several epitopes of these molecules. The inventors currently have rabbit polyclonal antibodies against synthetic polypeptide of Osterix assays, the test samples will be examined for protein concentration, separated by SDS-PAGE, and stained by coomassie blue. An additional SDS-PAGE gel that will be run in parallel will then be examined by western blotting with polyclonal antibodies to identify the putative band for Osterix. The amounts of Osterix proteins will then be calculated by multiplying the total protein concentration with the relative purity that will be determined by densitometric analysis of the coomassie-stained SDS-PAGE gel. For example, if one fraction contains 1 mg/ml protein and contains Osterix 70% purity, this fraction is calculated to contain 0.7 mg/ml Osterix protein. An advantage of this system will be that one can test simultaneously the protein profile of Osterix, so that one can eliminate contamination problems of degraded Osterix.

For a more rapid and routine analysis, the inventors will employ a double sandwich ELISA assay in which ELISA plates were first coated with a MAb against Osterix, incubated with test samples, and finally incubated with polyclonal antibodies against Osterix. The amounts of Osterix in the test samples will be determined based on the amounts of polyclonal antibodies binding to the plates.

Relative protein amounts of Osterix may not necessarily represent relative biological activities. This is especially the case when Osterix proteins are degraded and/or denatured during purification procedures or if different isoforms of Osterix protein exhibit different degrees of biological activity. Therefore, it will be important to measure relative biological activity. The present inventors prefer to determine the biological activity based on the capacity to bind to osteoblasts.

As is generally known in the art, to determine the specific activity, one would calculate the number of units of activity per milligram of total protein. In the purification procedure, the specific activity of the starting material, i.e., tissue extract, would represent the specific activity of the Osterix in its natural state. At each step, one would generally expect the specific activity of the Osterix to increase above this value, as it is purified relative to its natural state. In preferred embodiments, it is contemplated that one would assess the degree of purity of a given Osterix fraction by comparing its specific activity to the specific activity of the starting material, and representing this as X-fold purification. The use of "fold purification" is advantageous as the purity of an inhibitory fraction can thus be compared to another despite any differences which may exist in the actual units of activity or specific activity.

It is contemplated that the Osterix of the present invention be purified to between about 10-fold and about 30-fold, and preferably, of between about 30-fold and about 100-fold, and even more preferably, to about 300-fold, relative to its natural state.

The preferred purification method disclosed hereinbelow contains several steps and represents the best mode presently known by the inventors to prepare a substantially purified Osterix protein. This method is currently preferred as it results in the substantial purification of the protein or polypeptide, as assessed by western blotting, in yields sufficient for further characterization and use. This preferred mode of Osterix protein or polypeptide purification involves the execution of certain purification steps in the order described hereinbelow. However, as is generally known in the art, it is believed that the order of conducting the various purification steps may be changed, or that certain steps may be omitted, and still result in a suitable method for the preparation of a substantially purified Osterix protein or polypeptide.

As mentioned above, although preferred for use in certain embodiments, there is no general requirement that the Osterix proteins or polypeptides always be provided in their most purified state. Indeed, it is contemplated that less substantially purified proteins or polypeptides, which are nonetheless enriched in Osterix activity relative to the natural state, will have utility in certain embodiments. For example, less purified Osterix preparations may contain molecules that are associated naturally with Osterix. If so, this may, ultimately, lead to the identification of unique molecules that associate with Osterix on the cell surfaces (e.g., co-receptors) or in the cytoplasma (e.g., signaling components).

Methods exhibiting a lower degree of relative purification may have advantages in total recovery of protein product, or in maintaining the activity of an expressed protein. Inactive products also have utility in certain embodiments, such as, e.g., in antibody generation.

Partially purified Osterix fractions for use in such embodiments may be obtained by subjecting osteoblasts or C2C12 cell extract to one or a combination of the steps described. Substituting certain steps with improved equivalents is also contemplated to be useful. For example, it is appreciated that a cation-exchange column chromatography performed utilizing an HPLC apparatus will generally result in a greater-fold purification than the same technique utilizing a low pressure chromatography system.

However, it is known that the migration of a polypeptide can vary, sometimes significantly, with different conditions of SDS/PAGE (Capaldi et al., 1977, incorporated herein by reference). It will therefore be appreciated that under differing electrophoresis conditions, these molecular weights may vary.

2. Biologically Functional Equivalents and Structural Equivalents

As mentioned above, modification and changes may be made in the structure of Osterix and still obtain a molecule having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules, receptors, or osteoblasts. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. Equally, the same considerations may be employed to create a protein or polypeptide with countervailing (e.g., antagonistic) properties. It is thus contemplated by the inventors that various changes may be made in the sequence of Osterix protein or polypeptide (or underlying DNA) without appreciable loss of their biological utility or activity.

In terms of functional equivalents, it is also well understood by the skilled artisan that, inherent in the definition of a biologically functional equivalent protein or polypeptide, is the concept that there is a limit to the number of changes that may be made within a defined portion of the molecule and still result in a molecule with an acceptable level of equivalent biological activity. Biologically functional equivalent polypeptides are thus defined herein as those polypeptides in which certain, not most or all, of the amino acids may be substituted. Of course, a plurality of distinct proteins/polypeptides with different substitutions may be made and used in accordance with the invention.

It is also well understood that where certain residues are shown to be particularly important to the biological or structural properties of a protein or polypeptide, e.g., residues in active sites, such residues may not generally be exchanged.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine; and phenylalanine, tryptophan and tyrosine; are defined herein as biologically functional equivalents.

Conservative substitutions well known in the art include, for example, the changes of alanine to serine; arginine to lysine; asparagine to glutamine or histidine; aspartate to glutamate; cysteine to serine; glutamine to asparagine; glutamate to aspartate; glycogen to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent protein or polypeptide thereby created is intended for use in immunological embodiments, as in the present case. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented herein for use in such embodiments, as well as for other uses, such as in the design of probes and primers and the like.

Polypeptides corresponding to one or more antigenic determinants, or "epitopic core regions", of Osterix can also be prepared. Such polypeptides should generally be at least five or six amino acid residues in length, and may contain up to about 35–50 residues or so.

Synthetic polypeptides will generally be about 35 residues long, which is the approximate upper length limit of automated polypeptide synthesis machines, such as those available from Applied Biosystems (Foster City, Calif.). Longer polypeptides may also be prepared, e.g., by recombinant means.

U.S. Pat. No. 4,554,101 (Hopp, incorporated herein by reference) teaches the identification and preparation of epitopes from primary amino acid sequences on the basis of hydrophilicity. Through the methods disclosed in Hopp, one of skill in the art would be able to identify epitopes from within an amino acid sequence.

Numerous scientific publications have also been devoted to the prediction of secondary structure, and to the identification of epitopes, from analyses of amino acid sequences (Chou and Fasman, 1974a,b; 1978a,b, 1979). Any of these may be used, if desired, to supplement the teachings of Hopp in U.S. Pat. No. 4,554,101.

Moreover, computer programs are currently available to assist with predicting antigenic portions and epitopic core regions of proteins. Examples include those programs based upon the Jameson-Wolf analysis (Jameson and Wolf, 1988; Wolf et al., 1988), the program PepPlot® (Brutlag et al., 1990; Weinberger et al., 1985), and other new programs for protein tertiary structure prediction (Fetrow and Bryant, 1993). Further commercially available software capable of carrying out such analyses is termed MacVector (IBI, New Haven, Conn.).

In further embodiments, major antigenic determinants of a polypeptide may be identified by an empirical approach in which portions of the gene encoding the polypeptide are expressed in a recombinant host, and the resulting proteins tested for their ability to elicit an immune response. For example, PCR™ can be used to prepare a range of polypeptides lacking successively longer fragments of the C-terminus of the protein. The immunoactivity of each of these polypeptides is determined to identify those fragments or domains of the polypeptide that are immunodominant. Further studies in which only a small number of amino acids are removed at each iteration then allows the location of the antigenic determinants of the polypeptide to be more precisely determined.

Once one or more such analyses are completed, polypeptides are prepared that contain at least the essential features of one or more antigenic determinants. The polypeptides are then employed in the generation of antisera against the polypeptide. Minigenes or gene fusions encoding these determinants can also be constructed and inserted into expression vectors by standard methods, for example, using PCR™ cloning methodology.

The use of such small polypeptides for vaccination typically requires conjugation of the polypeptide to an immunogenic carrier protein, such as hepatitis B surface antigen, keyhole limpet hemocyanin or bovine serum albumin. Methods for performing this conjugation are well known in the art.

In addition to the peptidyl compounds described herein, the inventors also contemplate that other sterically similar compounds may be formulated to mimic the key portions of the polypeptide structure. Such compounds, which may be termed peptidomimetics, may be used in the same manner as the polypeptides of the invention and hence are also functional equivalents.

Certain mimetics that mimic elements of protein secondary structure are described in Johnson et al. (1993). The underlying rationale behind the use of polypeptide mimetics is that the polypeptide backbone of proteins exists chiefly to orientate amino acid side chains in such a way as to facilitate molecular interactions, such as those of antibody and antigen. A polypeptide mimetic is thus designed to permit molecular interactions similar to the natural molecule.

Some successful applications of the polypeptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

The generation of further structural equivalents or mimetics may be achieved by the techniques of modeling and chemical design known to those of skill in the art. The art of receptor modeling is now well known, and by such methods a chemical that binds to the osteoblast Osterix receptor can be designed and then synthesized. It will be understood that all such sterically similar constructs fall within the scope of the present invention.

3. Production of Antibodies Against Osterix

Means for preparing and characterizing antibodies are well known in the art (See, e.g., Antibodies: A Laboratory Manual, Cold Spring Harbor Laboratory, 1988; incorporated herein by reference). The methods for generating monoclonal antibodies (MAbs) generally begin along the same lines as those for preparing polyclonal antibodies. Briefly, a polyclonal antibody is prepared by immunizing an animal with an immunogenic composition in accordance with the present invention (either with or without prior immunotolerizing, depending on the antigen composition and protocol being employed) and collecting antisera from that immunized animal.

A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, μ-maleimidobencoyl-N-hydroxysuccinimide ester, carbodiimyde and bis-biazotized benzidine.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, toxins or synthetic compositions.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion. MHC antigens may even be used.

Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, may also be given. The process of boosting and titering is repeated until a suitable titer is achieved. When a desired level of immunogenicity is obtained, the immunized animal can be bled and the serum isolated and stored, and/or the animal can be used to generate monoclonal antibodies (MAbs).

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a polypeptide bound to a solid matrix, or by using, e.g., protein A or protein G chromatography.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified Osterix protein, polypeptide or peptide (or any osteoblast composition, if used after tolerization to common antigens). The immunizing composition is administered in a manner effective to stimulate antibody producing cells.

The methods for generating MAbs generally begin along the same lines as those for preparing polyclonal antibodies. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions. The inventors have generated the MAb against mouse Osterix in rats. This was primarily because it is technically difficult to immune mice with molecules of mouse origin. On the other hand, the inventors will prefer mice for the generation of MAb against human Osterix.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is accessible.

Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8,×63-Ag8.653, NS1/1.Ag 41, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1 \times 10^{-6}$ to $1 \times 10^{31\ 8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, rapid and easy to use, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways.

A sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration.

The individual cell lines could also be cultured in vitro, where the MAbs are naturally secreted into the culture medium from which they can be readily obtained in high concentrations.

In another embodiment, MAbs will be chimeric MAbs, including "humanized" MAbs. In such an approach, the chimeric MAb is engineered by cloning recombinant DNA containing the promoter, leader, and variable-region sequences from a mouse anti-Osterix producing cell and the constant-region exons from a human antibody gene. That is, mouse complementary determining regions ("CDRs") are transferred from heavy and light V-chains of the mouse Ig into a human V-domain. This can be followed by the replacement of some human residues in the framework regions of their murine counterparts.

The antibody encoded by such recombinant genes is a mouse-human chimera. Its antibody specificity is determined by the variable region derived from mouse sequences. Its isotype, which is determined by the constant region, is derived from human DNA. These humanized anti-Osterix antibodies are especially suitable for use in in vivo diagnostic and therapeutic methods. To produce humanized MAb as recombinant proteins, the nucleotide sequence encoding the variable domain of the light and heavy chains of mouse anti-human Osterix or mouse anti-human Osterix MAb will be first cloned by PCR™ and then inserted into the expression vector containing the human light and heavy chain constant regions. These expression vectors are used routinely by many investigators (Co et al., 1996; Co et al., 1992). It is contemplated that choosing a most appropriate human framework may be required. For example, designing antibodies with minimal positional templates is one way for this purpose (Caouto et al., 1995). Recombinant proteins may be produced in mammalian cells (e.g., mouse myeloma cell line S194) and then purified with protein A sepharose column.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

The MAbs of the invention will be useful in many ways. For example, they can be used to isolate and/or identify osteoblasts or the Osterix protein in biological systems or they may be used.

It is also contemplated that a molecular cloning approach may be used to generate MAbs. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

It is also contemplated that autoantibodies against Osterix proteins and/or polypeptides may be generated in mice, as well as other species (e.g., humans), under pathological conditions. For example, such autoantibodies may be present in detectable levels in human patients with symptoms for immunodeficiency. Autoantibodies may be detected by ELISA using relevant antibodies that recognize Osterix proteins or polypeptides. ELISA plates will be first coated with (rabbit) anti-Osterix antibodies and then coated with recombinant or native form of Osterix. These plates will be incubated with test samples (e.g., human serum) and then with antibodies against (human) immunoglobulin. Alternatively, recombinant or native forms of Osterix may be immobilized directly on the ELISA plates. The amounts of autoantibodies will be determined by measuring the amounts of anti-immunoglobulin antibodies that bind to the plates. This and other assays to measure autoantibodies against Osterix may be useful for diagnostic purposes.

D. Development of Osterix-related Agents and Assays

It is contemplated that the Osterix-related agents described herein will be useful in many areas, for example in screening assays, monitoring amounts and qualities of Osterix in clinical samples or to target the expression of foreign genes into osteoblasts, all as described in more detail herein. As used herein, the term "Osterix-related agents" refers to full length as well as partial DNA segments; other members of the Osterix family; isolated and purified native Osterix as well as recombinantly produced Osterix; antibodies raised to any of the above forms; cells and animals engineered to overproduce Osterix.

The Osterix-related agents described herein may, of course, additionally be used to search for molecules that modulate the expression and/or function of Osterix (e.g., naturally occurring proteins, chemicals, synthetic peptides, carbohydrates, lipids, recombinant proteins, cell extracts, and supernatant, etc.). This may, for example, involve the use of Osterix transfectants to search for molecules that bind to Osterix in the cell to enhance its activity thereby enhancing bone production.

Another contemplated use of the agents of the invention is to regulate cell differentiation for example, to regulate the differentiation of precursor cells, such as mesenchymal precursor cells, to form osteoblasts. In another example one may establish osteoblast lines by introducing Osterix promoters. This may be accomplished by using the 5'-flanking region of the Osterix gene to drive cellular differentiation toward osteoblasts or by using oncogenes (e.g., c-myc) driven by osteoblast-specific promoters.

It is also contemplated that the Osterix related agents described herein may be used to regulate the in vitro production of antibodies.

1. Osterix-related Agents and Assays

The following reagents are included in the present invention as "Osterix-related reagents": a) DNA segments of Osterix, including the 5'- and 3'-flanking regions, b) RNA segments of sense or anti-sense strands of Osterix, including truncated or mutated transcripts, c) Osterix polypeptides or proteins, including truncated or mutated forms and their biological equivalents, d) polyclonal or monoclonal antibodies against Osterix, e) C2C12 and other cell lines that express Osterix, f) vectors designed to produce Osterix polypeptides or proteins, g) cell lines that are engineered to express Osterix, h) other members of the Osterix family of genes and their products which can be identified with the above reagents, and i) relevant ligands of Osterix which can be identified with above reagents.

The following assays that employ Osterix-related reagents are also included in the present invention as "Osterix-related assays": a) assays to detect Osterix DNA, including Southern blotting, genomic PCR™, colony and plaque hybridization, and slot blotting; b) assays to detect Osterix RNA, including northern blotting, RT-PCR™, in situ hybridization, primer extension assay, and RNase protection assay; c) assays to detect Osterix polypeptides or proteins, including ELISA, Western blotting, immunoprecipitation, radioimmuno-absorption and -competition assays, and immunofluorescence and immunohistochemical stainings; and d) assays to search for reagents that modulate Osterix-dependent osteoblast interaction, including Osterix binding assay, DC-induced T cell activation assay, osteoblast adhesion assay, and assays to examine Osterix expression. Detailed methodologies for these assays will be described in the following sections.

2. Assays to Examine Osterix at DNA Levels

Nucleotides of Osterix (SEQ ID NO:1) or related nucleotides that exhibit significant homologies with or that contain portions of Osterix will be used as probes to detect members of the Osterix family of genes. The Osterix family of genes is defined as genes that are detectable with at least one of these probes. For this purpose, standard assays, including Southern blotting, PCR™, colony and plaque hybridization, and slot blot hybridization will be employed under various conditions with different degrees of stringency as described previously. Specimens to be tested include cDNA libraries, genomic DNA, cDNA, and DNA fragments isolated from cells or tissues. These assays may be modified to detect selectively mutated Osterix DNA. For this purpose, Southern blotting or PCR™ will be employed to detect or amplify the mutated DNA segments. These segments will then be sequenced to identify the mutated nucleotides. Alternatively, a combination of selected restriction enzymes will be employed to reveal molecular heterogeneity in Southern blotting. Moreover, these assays may be modified to detect selectively different domains or different portions of the Osterix nucleotide sequences. For this aim, one may employ probes or primers for different portions of the nucleotide sequences. More sophisticated methods may be employed to screen point mutations. For example, it is contemplated that one may choose a PCR™-single-strand conformation polymorphism (PCR™-SSCP) analysis (Sarkar et al., 1995).

3. Assays to Examine Osterix at RNA Levels

Nucleotides of Osterix (SEQ ID NO:1) or related nucleotides that exhibit significant homologies with or that contain portions of with Osterix will be used as probes to detect transcripts of the Osterix family of genes. For this purpose, standard assays, including northern blotting, RT-PCR™, in situ hybridization, primer extension assay and RNase protection assay will be employed under various conditions with different degrees of stringency as described previously. Specimens to be tested include total RNA and mRNA isolated from cells or tissues and cell and tissue samples themselves obtained from living animals or patients. These assays may be modified to detect selectively the transcripts for different domains or different isoforms. For this purpose, the inventors will employ probes or primers for different portions of the nucleotide sequences. In fact, the inventors have been able to identify several truncated transcripts of Osterix by RT-PCR™ using a panel of different primer sets. These transcripts have been found to be produced by alternative splicing mechanisms. Similar methods using RT-PCR™ may be employed to identify other spliced variants and even other isoforms that are produced by other mechanisms. Alternatively, northern blotting may be used to detect selectively different isoforms. For this purpose, oligonucleotide probes will be constructed, each covering different portions of the nucleotide sequences. To defined the nucleotides that are deleted from the original sequence, RNase protection assays may be employed. Detection of mutated RNA is also included in the present invention. For this aim, RNA isolated from osteoblasts will be analyzed by northern blotting or RT-PCR™.

It is further contemplated that assays may be designed to detect selectively different RNA species. Similar methods using RT-PCR™ may be employed to identify spliced variants and even other isoforms that are produced by other mechanisms. Alternatively, northern blotting may be used to detect selectively different isoforms. For this purpose, oligonucleotide probes will be constructed, each covering different portions of the nucleotide sequences. To define the nucleotides that are deleted from the original sequence, RNase protection assays may be employed.

4. Assays to Examine Osterix at Protein or Polypeptide Levels

Antibodies against Osterix will be used to detect Osterix proteins or polypeptides. For this purpose, standard assays, including ELISA, western blotting, immunoprecipitation, radioimmuno-absorption and radioimmuno-competition assays, and immunofluorescence and immunohistochemical stainings will be employed under various conditions with different degrees of specificity and sensitivity. Specimens to be tested include viable cells, whole cellular extracts, and different subcellular fractions of established cell lines, as well as cells, tissues, and body fluids isolated from living animals or patients. These assays may be modified to detect selectively different epitopes, domains, or isoforms of Osterix polypeptides or proteins. For this purpose, the inventors will develop and employ a panel of MAb against different epitopes or domains.

5. Assays to Search for Reagents that Modulate the Activity of Osterix and the Expression of Osterix Gene Finally, the Osterix-related assays described above may also be used to search for molecules that modulate Osterix-dependent activity, comprising admixing a Osterix expressing cell with a candidate substance and identifying if the candidate substance inhibits/stimulates the expression of Osterix. Preferably, the Osterix expressing cell will be an osteoblast. Alternatively, the Osterix expressing cell may comprise an engineered cells that expresses recombinant Osterix.

The first screening will determine whether the candidate substance affects the expression of Osterix. For this purpose, osteoblast expressing cells (e.g., C2C12 cells, mouse osteoblasts, human osteoblasts) will be treated with the candidate substance(s) either individually or in combination and then examined for enhanced Osterix activity at the levels of mRNA, protein, and function. Alternatively, the candidate substances may be tested in vivo by administering into live animals such as mice. In this case, osteoblasts will be isolated from mice after treatment with the candidate substance(s) or combinations thereof and examined in vitro for enhanced Osterix activity, once again, by measuring the levels of mRNA, protein, and/or function. In performing these assays, it will be important to also examine the effect(s) of candidate substances on the activity of different isoforms of Osterix. In preferred embodiments, these agents that enhance or stimulate Osterix expression will be formulated in a pharmaceutical acceptable medium.

A candidate substance(s) that inhibits the activity of Osterix within osteoblasts may be identified by inhibition of osteoblast differentiation or bone formation. The invention thus, provides agents that inhibit Osterix-mediated activation of osteoblasts. In preferred embodiments, the agent of the invention will be formulated in a pharmaceutical acceptable medium.

The present invention further provides a method for purifying osteoblasts. Preferably, the method comprises the steps of:
(a) preparing an immobilized Osterix composition comprising an Osterix protein or polypeptide linked to a solid support;
(b) contacting said immobilized Osterix composition with a test composition suspected of containing osteoblasts under conditions effective to allow osteoblast binding to said Osterix;
(c) removing unbound components from said test composition; and
(d) releasing bound osteoblasts from said immobilized Osterix composition.

In still further embodiments, the present invention concerns a method for identifying new osteoblast interaction inhibitory/stimulatory compounds, which may be termed as "candidate substances." It is contemplated that this screening technique will prove useful in the general identification of any compound that will serve the purpose of inhibiting/stimulating osteoblast activation. Stimulators of Osteoblast activation have therapeutic applications in diseases such as osteoporosis, bone reconstructions in bone fracture repair etc.

It is further contemplated that useful compounds in this regard will in no way be limited to antibodies. In fact, it may prove to be the case that the most useful pharmacological compounds for identification through application of the screening assay will be non-peptidyl in nature and serve to inhibit the osteoblast activation process through a tight binding or other chemical interaction.

Candidate molecules may be examined for their capacities to suppress or to enhance the expression of Osterix by osteoblasts at mRNA or protein levels. For this aim, osteoblasts will be incubated with test samples and then examined for Osterix expression by northern blotting, RT-PCR™, in situ hybridization, primer extension assay and RNase protection assay (at RNA levels) or by ELISA, western blotting, immunoprecipitation, radioimmuno-absorption and competition assays, and immunofluorescence and immunohistochemical stainings (at protein levels).

While a candidate substance may be any type of substance that may interact with Osterix to enhance its activity and stimulate bone formation, one preferred method for obtaining candidate substances will be by utilizing combinatorial chemistry techniques. Such techniques are well known to the skilled artisan and include methods as described in VanHijfte L, et al., 1999 and Floyd C. D. et al., 1999 (incorporated herein by reference).

E. Other Members of the Osterix Family and Ligands of Osterix

1. Other Members of the Osterix Family

It is expected that there exists other molecules that share structural or functional properties with Osterix. For example, human equivalents have been identified for the molecule that was originally discovered in mice. These molecules, including Osterix-equivalents in other species, Osterix isoforms, and Osterix subunits, are designated as members of the Osterix family and are included in the present invention. This is because the availability of Osterix-related reagents and assays allows the inventors to identify those molecules that share structural or functional properties with Osterix.

To identify human equivalents of Osterix, genomic PCR™ and RT-PCR™ amplification may be used. In these methods, human genomic DNA or cDNA will be amplified, under various conditions with different degrees of stringency, using primer sets designed on the basis of murine Osterix nucleotide/amino acid sequences as described above. PCR™ products will then be cloned and sequenced. If they exhibit significant homologies to murine Osterix at the level of either nucleotide or amino acid, these PCR™ products will be used to clone relevant cDNA from a cDNA library prepared from human cells.

To perform colony hybridization, a cDNA library prepared from human osteoblasts or peripheral blood leukocytes or a human genomic DNA library will be hybridized under various conditions with different degrees of stringency, with murine Osterix cDNA or targeted fragments of these cDNA. Alternatively, these libraries may be hybridized with oligonucleotides synthesized based on the sequences of murine Osterix and Osterix.

In fact, the inventors have been able to detect a human equivalent of Osterix by Southern blotting. These results indicate that murine Osterix and human Osterix show a nucleotide sequence homology that is high enough to be detectable with the nucleotide sequence of SEQ ID NO:1. These results validate that human equivalents of Osterix are detectable with cDNA probes of mouse origin. Human Osterix also showed 95% identity in amino acid sequence to mouse Osterix by alignments of DNA sequences.

It is contemplated that antibodies which recognize human osteoblasts will be useful in a number of ways. For example, antibodies that recognize human osteoblasts may be used to identify human equivalents of Osterix. More specifically, relevant proteins may be purified by immunoprecipitation and then sequenced. cDNA encoding human equivalents may then be cloned by PCR™ and/or colony hybridization using PCR™ products (amplified with primers designed from the amino acid sequences) or oligonucleotides.

Relevant ligands of murine Osterix may serve as molecular probes to identify human equivalents of Osterix. More specifically, soluble forms of ligands for murine Osterix are first examined for their binding to human osteoblasts. If they show significant binding, an expression cDNA cloning strategy is employed, in which a non-osteoblast line (which express no detectable Osterix) is transfected with a cDNA library prepared from human osteoblasts. Transfectants that bind soluble ligands (in other words, expressing human equivalents of Osterix) are isolated by FACS or panning.

This procedure will be repeated to identify the cDNA that encode human equivalents of Osterix.

It is contemplated that other polypeptides that interact with Osterix can be identified by the yeast two hybrid system. The yeast two-hybrid system is extremely useful and well known in the art for studying protein:protein interactions and therefore is used herein to determine the interaction of other polypeptides with Osterix. Variations of the system are available for screening yeast phagemid (Harper et al., 1993; Elledge et al., 1991) or plasmid (Bartel et al., 1993a,b; Finley and Brent, 1994) cDNA libraries to clone interacting proteins, as well as for studying known protein pairs.

The two-hybrid system is a genetic method that uses transcriptional activity as a measure of protein::protein interaction. It relies on the modular nature of many site-specific transcriptional activators, which consist of a DNA-binding domain and a transcriptional activation domain. The DNA binding- domain serves to target the activator to the specific genes that will be expressed and the activation domain contacts other proteins of the transcriptional machinery to enable transcription to occur. The two-hybrid system is based on the observation that the two domains of the activator need not be covalently linked and can be brought together by the interaction of any two proteins. The application of this system requires that two hybrids be constructed: a DNA-binding domain (of Osterix) fused to a protein, and a transcription activation domain (of Osterix) fused to some protein. These two hybrids are expressed in a cell containing one or more reporter genes. If the X and Y proteins interact, they create a functional activator by bringing the activation domain into close proximity with the DNA-binding domain. This can be detected by expression of the reporter genes. While the assay has been generally performed in yeast cells, it works similarly in mammalian cells and is applicable in other eukaryotic cells as well. See, Phizicky, E. M. and S. Fields (1995) Protein-Protein Interactions: Methods for detection and analysis. Microbiological Reviews. 59:94–123, 105.

The success of the two-hybrid system relies upon the fact that the DNA binding and polymerase activation domains of many transcription factors, such as GAL4, can be separated and then rejoined to restore functionality (Morin et al., 1993). Yeast strains with integrated copies of various reporter gene cassettes are co-transformed with two plasmids, each expressing a different fusion protein. One plasmid encodes a fusion between protein "X" and the DNA binding domain of, for example, the GAL4 yeast transcription activator (Brent and Ptashne, 1985; Ma and Ptashne, 1987; Keegan et al., 1986), while the other plasmid encodes a fusion between protein "Y" and the RNA polymerase activation domain of GAL4 (Keegan et al., 1986). The plasmids are transformed into a strain of the yeast that contains a reporter gene, such as lacZ, whose regulatory region contains GAL4 binding sites. If proteins X and Y interact, they reconstitute a functional GAL4 transcription activator protein by bringing the two GAL4 components into sufficient proximity to activate transcription. Either hybrid protein alone must be unable to activate transcription of the reporter gene, the DNA-binding domain hybrid, because it does not provide an activation function, and the activation domain hybrid, because it cannot localize to the GAL4 binding sites. Interaction of the two test proteins reconstitutes the function of GAL4 and results in expression of the reporter gene. The reporter gene cassettes consist of minimal promoters that contain the GAL4 DNA recognition site (Johnson and Davis, 1984; Lorch and Kornberg, 1984) cloned 5' to their TATA box. Transcription activation is scored by measuring either the expression of β-galactosidase or the growth of the transformants on minimal medium lacking the specific nutrient that permits auxotrophic selection for the transcription product, e.g., URA3 (uracil selection) or HIS3 (histidine selection). See, Bartel et al., 1993a; Durfee et al., 1993; Fields and Sternglantz, 1994, and U.S. Pat. No. 5,283,173. These and all references cited in this application are hereby incorporated by reference.

In addition to the two-hybrid system other methods such as co-immunoprecipitation, crosslinking, and copurification through gradients or chromatographic columns may also be used to identify polypeptides and proteins that interact with Osterix. The co-purified or co-precipitated proteins may then be identified by methods known in the art including protein sequencing.

Mammalian cells transfected with Osterix cDNA may be used to identify peptides that bind to Osterix. Specifically, *E. coli* expressing a random peptide display library (e.g., FliTrx™) will be screened for the binding to the above transfectants by panning. After several rounds of screening, positive clones will be sequenced. Full-length polypeptides will then be identified by colony hybridization of an osteoblast cDNA library using oligonucleotide or PCR™ primers synthesized based on the peptide sequence.

For an alternate, biochemical approach to isolating relevant ligands for Osterix, total cell extracts or membrane fractions prepared from an osteoblast line will be applied onto an affinity column conjugated with soluble Osterix. Molecules bound to the column (i.e., putative ligands) will then be eluted by changing the pH or washing with EDTA or carbohydrates. The eluents will be purified by conventional column chromatography and HPLC and then examined for amino acid sequences. cDNA encoding these ligands will be cloned by colony hybridization of an osteoblast cDNA library using oligonucleotide or PCR™ primers synthesized based on the revealed amino acid sequence.

F. Clinical and Subclinical Application of Osterix-Related Reagents and Assays

It is further contemplated that the Osterix related agents described herein, i.e., Osterix proteins or polypeptides, antibodies raised against such proteins or polypeptides, mutated, truncated or elongated forms of Osterix, antibodies raised against such forms, cells engineered to overproduce or lack Osterix, proteins that interact with Osterix, and agents that stimulate, activate, inhibit or modulate Osterix gene expression may be used to promote bone formation. That is, they may be used for the treatment of bone disorders, such as osteoporosis, glucocorticoid induced osteoporosis, Paget's disease, abnormally increased bone turnover, periodontal disease, tooth loss, bone fractures, rheumatoid arthritis, periprosthetic osteolysis, osteogenesis imperfecta, metastatic bone disease, hypercalcemia of malignancy and the like.

1. Pharmacological Application to Search for Reagents that Modulate Osterix-dependent Osteoblast Function One may choose to determine whether candidate substances may affect the expression of Osterix by osteoblasts. For this purpose, osteoblast preparations (e.g., C2C12 cells, mouse osteoblasts, human osteoblasts) will be treated with candidate substances either individually or in combination and then examined for Osterix expression at the levels of mRNA, protein, and function. Alternatively, those candidate substances may be tested in vivo by administering into living animals. In this case, osteoblasts will be isolated from those mice after treatment and then examined in vitro for Osterix expression, once again, at the levels of mRNA, protein, and function. In performing these assays, it will be important to also examine the effect(s) of candidate substances on the expression of different isoforms of Osterix.

In these embodiments, the present invention is directed to a method for determining the ability of a candidate substance to stimulate the osteoblast activation process, the method including generally the steps of:

(a) admixing a first composition comprising a population of recombinant cells expressing Osterix with a second composition comprising a population of osteoblasts (and relevant antigen if required);

(b) incubating the admixture with a candidate substance;

(c) testing said admixture for enhanced osteoblast activation; and (d) identifying a candidate substance that inhibits the activation of osteoblasts.

To identify a candidate substance, one would first obtain an Osterix composition that is capable of activating osteoblasts. Naturally, one would measure or determine the osteoblast activation capacity of the Osterix composition in the absence of the added candidate substance. One would then add the candidate substance to the Osterix composition and re-determine the ability of the Osterix composition to activate osteoblasts in the presence of the candidate substance. A candidate substance which increases the osteoblast activation capacity of the Osterix composition relative to the activity in its absence is indicative of a candidate substance with stimulatory capability.

The candidate screening assay is quite uncomplicated to set up and perform, and is related in many ways to the assay discussed above for determining protein or polypeptide activity. Thus, after obtaining a relatively purified preparation of the protein or polypeptide, either from native or recombinant sources, one will desire to admix a candidate substance with the protein preparation, preferably under conditions which would allow the protein to perform its osteoblast activation function. In this fashion, one can measure the ability of the candidate substance to increase osteoblast activation capacity relatively in the presence of the candidate substance.

It will, of course, be understood that all the screening methods of the present invention are useful in themselves notwithstanding the fact that effective candidates may not be found, since it would be a practical utility to know that Osterix agonists and/or antagonists do not exist. The invention provides methods for screening for such candidates, not in finding them.

Candidate molecules may augment Osterix-dependent osteoblast interaction. To test this possibility, test samples will be added to the osteoblast activation assay, the Osterix-binding assay, or the osteoblast adhesion assay. Samples that enhance the function of Osterix in one of these assays will be considered to possess an augmentative property.

Any molecule can be a candidate molecule for the purposes of the present invention. It is envisioned that candidate molecules will be designed and created most effectively using well known combinatorial chemistry techniques, such as those described in VanHijfte L, et al., 1999 and Floyd C. D. et al., 1999, incorporated herein by reference.

F. Therapies using Osterix

As Osterix is involved in bone formation it may be effectively used for the treatment of bone disorders, such as osteoporosis, glucocorticoid induced osteoporosis, Paget's disease, abnormally increased bone turnover, periodontal disease, tooth loss, bone fractures, rheumatoid arthritis, periprosthetic osteolysis, osteogenesis imperfecta, metastatic bone disease, hypercalcemia of malignancy and the like.

1. Protein Therapy of Osterix

Another therapy approach is the provision, to a subject, of Osterix polypeptide, active fragments, synthetic peptides, mimetics or other analogs thereof. The protein may be produced by recombinant expression means or, if small enough, generated by an automated peptide synthesizer. Formulations would be selected based on the route of administration and purpose including but not limited to liposomal formulations and classic pharmaceutical preparations.

2. Genetic-based Therapies with Osterix

One of the therapeutic embodiments contemplated by the present inventors is the intervention, at the molecular level, in the events involved in the bone formation. Specifically, the present inventors intend to provide, to a bone cell or a precursor cell, an expression construct capable of providing a Osterix polypeptide to that cell. Because the sequence homology between the human, mouse, rat, rabbit, murine, primate and dog genes, any of these nucleic acids could be used in human therapy, as could any of the gene sequence variants which would encode the same, or a biologically equivalent polypeptide. The lengthy discussion above of expression vectors and the genetic elements employed therein is incorporated into this section by reference. Particularly preferred expression vectors are viral vectors.

Those of skill in the art are well aware of how to apply gene delivery to in vivo and ex vivo situations. For viral vectors, one generally will prepare a viral vector stock. Depending on the kind of virus and the titer attainable, one will deliver 1 to 100, 10 to 50, 100–1000, or up to $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, or $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for different disease types. The section below on routes contains an extensive list of possible routes. In a different embodiment, ex vivo gene therapy is contemplated. In an ex vivo embodiment, cells from the patient are removed and maintained outside the body for at least some period of time. During this period, a Osterix gene is delivered to these cells, after which the cells are reintroduced into the patient.

In some embodiments of the present invention a subject is exposed to a viral vector and the subject is then monitored for expression construct-based toxicity, where such toxicity may include, among other things, causing a condition that is injurious to the subject.

3. Pharmaceutical Formulations and Delivery

In a preferred embodiment of the present invention, a method of treatment for a bone disorder by the delivery of an expression construct encoding a Osterix polypeptide is contemplated. Bone disorders, such as osteoporosis, glucocorticoid induced osteoporosis, Paget's disease, abnormally increased bone turnover, periodontal disease, tooth loss, bone fractures, rheumatoid arthritis, periprosthetic osteolysis, osteogenesis imperfecta, metastatic bone disease, hypercalcemia of malignancy and the like may be treated.

An effective amount of the pharmaceutical composition, generally, is defined as that amount sufficient to detectably and repeatedly to ameliorate, reduce, minimize or limit the extent of the disease or its symptoms. More rigorous definitions may apply, including elimination, eradication or cure of disease.

(i) Administration

The therapeutic expression construct expressing an Osterix polypeptide may be administered by any of the routes and the route of administration will vary, naturally, with the location and nature of the lesion, and include, e.g., intradermal, transdermal, parenteral, intravenous, intramuscular, intranasal, subcutaneous, percutaneous, intratracheal, intraperitoneal, intratumoral, perfusion, lavage, direct injection, and oral administration and formulation. Treatment regimens may vary as well, and often depend on disease progression, and health and age of the patient. The clinician will be best suited to make such decisions based on the known efficacy and toxicity (if any) of the therapeutic formulations.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time. Unit dose of the present invention may conveniently be described in terms of plaque forming units (pfu) for a viral construct. Unit doses range from $10^3$, $10^4$, $10^5$, $10^6$, $10^7$, $10^8$, $10^9$, $10^{10}$, $10^{11}$, $10^{12}$, $10^{13}$ pfu and higher. Alternatively, depending on the kind of virus and the titer attainable, one will deliver 1 to 100, 10 to 50, 100–1000, or up to about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, or $1\times10^{15}$ or higher infectious viral particles (vp) to the patient or to the patient's cells.

Injection of nucleic acid constructs may be delivered by syringe or any other method used for injection of a solution, as long as the expression construct can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vaccuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The terms "contacted" and "exposed," when applied to a cell, are used herein to describe the process by which a therapeutic construct encoding a Osterix polypeptide is delivered to a target cell.

H. Knockouts, Transgenic Animals And Cells

Cells, cell lines and animals deficient for the Osterix gene can be generated and utilized, for example, as part of the identification of specific modulators such as stimulators or inhibitors of osteoblast gene expression and activity in addition to the identification assays described above. Thus, Osterix deficient cells, cell lines and animals will frequently be used herein as a representative example.

The term "Osterix-deficient", as used herein, refers to cells, cell lines and/or animals which exhibit a lower level of functional Osterix activity than corresponding cells, or cell lines or animals whose cells, contain two normal, wild type copies of the Osterix gene. Preferably, "Osterix-deficient" refers to an absence of detectable functional Osterix activity.

A representative Osterix-deficient, or "knockout" animal is a mouse Osterix-deficient animal. Knockout animals are well known to those of skill in the art. See, for example, Horinouchi et al., 1995; and Otterbach and Stoffel, 1995, both of which are incorporated herein by reference in their entirety. Techniques for generating additional Osterix knockout cells, cell lines and animals are described below.

Cells and cell lines deficient in Osterix activity can be derived from Osterix knockout animals, utilizing standard techniques well known to those of skill in the art. Such animals may be used to derive a cell line which may be used as an assay substrate in culture. While primary cultures may be utilized, the generation of continuous cell lines is preferred. For examples of techniques which may be used to derive a continuous cell line from the transgenic animals, see Small et al, 1985. Such techniques for generating cells and cell lines can also be utilized in the context of the transgenic and genetically engineered animals described below.

With respect to Osterix deficient cells, such cells can, for example, include cells taken from and cell lines derived from patients exhibiting bone disorders, such as osteoporosis. Additional Osterix-deficient cells and cell lines can be generated using well known recombinant DNA techniques such as, for example, site-directed mutagenesis, to introduce mutations into Osterix gene sequences which will disrupt Osterix activity.

Osterix-deficient cells and animals can be generated using the Osterix nucleotide sequences described in the present invention. Such animals can be any species, including but not limited to mice, rats, rabbits, guinea pigs, pigs, micropigs, and non-human primates, e.g., baboons, squirrel monkeys and chimpanzees.

Any technique known in the art may be used to introduce a transgene, such as an inactivating gene sequence, into animals to produce the founder lines of transgenic animals. Such techniques include, but are not limited to pronuclear microinjection (U.S. Pat. No. 4,873,191); retrovirus mediated gene transfer into germ lines (Van der Putten et al., 1985); gene targeting in embryonic stem cells (Thompson et al., 1989,); electroporation of embryos (Lo, 1983); and sperm-mediated gene transfer (Lavitrano et al., 1989); etc. For a review of such techniques, see Gordon, 1989, which is incorporated by reference herein in its entirety.

As listed above, standard embryonal stem cell (ES) techniques can, for example, be utilized for generation of Osterix knockouts. ES cells can be obtained from preimplantation embryos cultured in vitro (See, e.g., Evans et al., 1981; Bradley et al., 1984; Gossler et al., 1986; Robertson et al., 1986; Wood et al., 1993) The introduced ES cells thereafter colonize the embryo and contribute to the germ line of a resulting chimeric animal (Jaenisch, 1988).

To accomplish Osterix gene disruptions, the technique of site-directed inactivation via gene targeting may be used (Thomas, K. R. and Capecchi, M. R., 1987) and review in Frohman et al., 1989; Cappecchi, 1989; Barribault et al., 1989; Wagner, 1990; and Bradley et al., 1992.

Further, standard techniques such as, for example, homologous recombination, coupled with Osterix sequences, can be utilized to inactivate or alter any Osterix genetic region desired. A number of strategies can be utilized to detect or select rate homologous recombinants. For example, PCR can be used to screen pools of transformant cells for homologous insertion, followed by screening of individual clones (Kim et al., 1988; Kim et al., 1991). Alternatively, a positive genetic selection approach can be taken in which a marker gene is constructed which will only be active if homologous insertion occurs, allowing these recombinants to be selected directly (Sedivy et al., 1989). Additionally, the positive-negative approach (PNS) method can be utilized (Mansour et al., 1988; Capecchi, 1989; Capecchi, 1989). Utilizing the PNS method, nonhomologous recombinants are selected against by using the Herpes Simplex virus thymidine kinase (HSV-TK) gene and selecting against its nonhomologous insertion with herpes drugs such as ganciclovir or FIAU. By such counter-selection, the number of homologous recombinants in the surviving transformants is increased.

ES cells generated via techniques such as these, when introduced into the germline of a nonhuman animal make possible the generation of non-mosaic, i.e., non-chimeric progeny. Such progeny will be referred to herein as founder animals. Once the founder animals are produced, they may be bred, inbred, outbred, or crossbred to produce colonies of the particular animal.

Taking as an example of the above, the generation of a Osterix knockout mouse, first, standard techniques can be utilized to isolate mouse Osterix genomic sequences. Such sequences can be routinely isolated by utilizing standard molecular techniques and human Osterix nucleotide sequences as probes and/or as PCR primers, as discussed below.

An inactive allele of the Osterix gene can then be generated by targeted mutagenesis using standard procedures of combined positive and negative selection for homologous recombination in embryonic stem (ES) cells. Osterix genomic clones can be isolated, for example, from a 129/sv mouse genomic library, which is isogenic with the ES cells to be used for gene targeting. The null targeting vector can be constructed containing homologous sequences flanking both 5' and 3' sides of a deletion of the first coding exon (exon 2), including the translational initiation codon, and other essential coding sequences of the gene. The vector carries a resistance marker, e.g., a neomycin resistance marker (Neo) for positive selection and a negative marker, e.g., a thymidine kinase (TK) marker, for negative selection. Vectors can be utilized which are analogous to previously reported targeting vectors, successfully used for generating knock-out mice for other genes, e.g., for Niemann-Pick Disease, NMDA receptor and thyroid hormone receptor.

Briefly, vector DNA can be electroporated into W9.5 ES cells (male-derived), which can then be cultured and selected on feeder layers of mouse embryonic fibroblasts derived from transgenic mice expressing a Neo gene. G418 (350 mg/ml; for gain of Neo) and ganciclovir (2 mM; for loss of TK) can be added to the culture medium to select for resistant ES cell colonies that have undergone homologous recombination at the URO-D gene. Recombinants are identified by screening genomic DNA from ES cell colonies by Southern blot hybridization analysis. Correctly targeted ES cell clones, which also carry a normal complement of 40 chromosomes, can be used to derive mice carrying the mutation. ES cells can be micro-injected into blastocysts at 3.5 days post-coitum obtained from C57BL/6J mice, and blastocysts will be re-implanted into pseudopregnant female mice, which serve as foster mothers. Chimeric progeny derived largely from the ES cells will be identified by a high proportion of agouti coat color (the color of the 129/sv strain of origin of the ES cells) against the black coat color derived from the C57BL/6J host blastocyst. Male chimeric progeny will be tested for germline transmission of the mutation by breeding with C57BL/6J females. Agouti progeny derived from these crosses will be expected to be heterozygous for the mutation, which will be confirmed by Southern blot analysis. These F1 heterozygous progeny will be inter-bred to generate F2 litters containing progeny of all three genotypes (wild type, heterozygous and homozygous mutants) for phenotypic analyses. 1. Methods of making Transgenic Animals Thus, a particular embodiment of the present invention provides transgenic animals which are knockouts for the Osterix gene and thus serve as models for bone disorders involving Osterix and also provides an assay system for identification of modulators which includes both inhibitors and stimulators of Osterix gene expression as well as Osterix functional activity.

Although the present discussion refers to transgenic mice, it is understood that mice are merely exemplary model animal, and any other mammalian animal routinely used as model animal (e.g., rat, guinea pig, rabbit, cats, dogs, pigs and the like) may be generated using the technology described herein. In a general aspect, a transgenic animal is produced by the integration of a given transgene into the genome in a manner that permits the expression of the transgene. The terms "animal" and "non-human animal", as used herein, include all vertebrate animals, except humans. It also includes individual animals in all stages of development, including embryonic and fetal stages. A "transgenic animal" is any animal containing one or more cells bearing genetic information received, directly or indirectly, by deliberate genetic manipulation at the subcellular level. The genetic manipulation can be performed by any method of introducing genetic material to a cell, including, but not limited to, microinjection, infection with a recombinant virus, particle bombardment or electroporation. The term is not intended to encompass classical cross-breeding or in vitro fertilization, but rather is meant to encompass animals in which one or more cells receive a recombinant DNA molecule. This molecule may be integrated within a chromosome, or it may be extrachromosomally replicating DNA. The genetic information may be foreign to the species of animal to which the recipient belongs, foreign only to the individual recipient, or genetic information already possessed by the recipient expressed at a different level, a different time, or in a different location than the native gene.

Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which are knockouts of Osterix.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 µg/ml in 5 mM Tris, pH 7.4 and 0.1 mM EDTA.

Other methods for purification of DNA for microinjection are described in Hogan et al, *Manipulating the Mouse Embryo* (Cold Spring Harbor Laboratory, Cold Spring Harbor, N.Y., 1986), in Palmiter et al. *Nature* 300:611 (1982); in *The Qiagenologist, Application Protocols*, 3rd edition, published by Qiagen, Inc., Chatsworth, Calif.; and in Sambrook et al. *Molecular Cloning: A Laboratory Manual* (Cold Spring Harbor Laboratory, Cold Spring Harbor, N.Y., 1989).

Female mice are induced to superovulate, e.g., by using an injection of pregnant mare serum gonadotropin (PMSG; Sigma) followed, 48 hours later, by an injection of human chorionic gonadotropin (hCG; Sigma). Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

25 μg of a SalI-linearized SGC targeting vector is electroporated into $1 \times 10^7$ embryonic stem (ES) cells, After a suitable period of incubation, e.g., 36 hr, the transfected cells are then selected using G418 and FIAU. The G418-FIAU-resistant ES colonies are picked into 96-well plates (Ramirez-Solis et al, 1993). Positive ES clones are injected into C57BL/6 blastocysts and transferred into pseudopregnant ICR female recipients. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

The resulting male chimeras are bred with C57BL/6 females. Germline transmission can be screened by using a phenotype, such as coat color and confirmed by Southern analysis.

As noted above, transgenic animals and cell lines derived from such animals may find use in certain testing experiments. In this regard, Osterix transgenic animals and cell lines may be exposed to test substances. These test substances can be screened for the ability to induce differentiastion of cells to osteoblasts. Compounds identified by such procedures will be useful in the treatment of bone disorders such as osteoporosis. Thus the compounds identified may be used to prevent, treat, ameliorate bone loss.

a. ES Cells

ES cells are obtained from pre-implantation embryos cultured in vitro (Evans et al. 1981; Bradley et al. 1984; Gossler et al. 1986; Robertson et al. (1986). Transgenes are introduced into ES cells using a number of means well known to those of skill in the art. The transformed ES cells can thereafter be combined with blastocysts from a non-human animal. The ES cells thereafter colonize the embryo and contribute to the germ line of the resulting chimeric animal (for a review see Jaenisch, 1988).

Once the DNA is introduced, e.g., by electroporation (Troneguzzo et al., 1988; Quillet et al., 1988; Machy et al., 1988), the cells are cultured under conventional conditions well known in the art. In order to facilitate the recovery of those cells which have received the DNA molecule containing the desired gene sequence, it is preferable to introduce the DNA containing the desired gene sequence in combination with a second gene sequence which would contain a detectable marker gene sequence. For the purposes of the present invention, any gene sequence whose presence in a cell permits one to recognize and clonally isolate the cell may be employed as a detectable (selectable) marker gene sequence. The presence of the detectable (selectable) marker sequence in a recipient cell may be recognized by PCR, by detection of radiolabeled nucleotides, or by other assays of detection which do not require the expression of the detectable marker sequence. Typically, the detectable marker gene sequence will be expressed in the recipient cell, and will result in a selectable phenotype. Selectable markers are well known to those of skill in the art. Some examples include the hprt gene (Littlefield, 1964), the neo gene, the tk (thyroidinc kinase) gene of herpes simplex virus (Giphart-Gassler et al., 1989), or other genes which confer resistance to amino acid or nucleoside analogues, or antibiotics, etc.

Any ES cell may be used in accordance with the present invention. It is, however, preferred to use primary isolates of ES cells. Such isolates may be obtained directly from embryos such as the CCE cell line disclosed by Robertson (1989), or from the clonal isolation of ES cells from the CCE cell line (Schwartzberg et al., 1989). Such clonal isolation may be accomplished according to the method of Robertson (1987). The purpose of such clonal propagation is to obtain ES cells which have a greater efficiency for differentiating into an animal. Clonally selected ES cells are approximately 10-fold more effective in producing transgenic animals than the progenitor cell line CCE.

b. Homologous Recombination

Homologous recombination (Koller and Smithies, 1992), directs the insertion of the transgene to a specific location. This technique allows the precise modification of existing genes, and overcomes the problems of positional effects and insertional inactivation observed with transgenic animals generated by pronuclear injection or use of viral vectors. Additionally, it allows the inactivation of specific genes as well as the replacement of one gene for another. In particular embodiments, the DNA segment comprises two selected DNA regions that flank the Osterix coding region, thereby directing the homologous recombination of the coding region into the genomic DNA of a non-human animal species.

Thus, a preferred method for the delivery of transgenic constructs involves the use of homologous recombination, or "knock-out technology". Homologous recombination relies, like antisense, on the tendency of nucleic acids to base pair with complementary sequences. In this instance, the base pairing serves to facilitate the interaction of two separate nucleic acid molecules so that strand breakage and repair can take place. In other words, the "homologous" aspect of the method relies on sequence homology to bring two complementary sequences into close proximity, while the "recombination" aspect provides for one complementary sequence to replace the other by virtue of the breaking of certain bonds and the formation of others.

Put into practice, homologous recombination is used as follows. First, the target gene is selected within the host cell. Sequences homologous to the target gene are then included in a genetic construct, along with some mutation that will render the target gene inactive (stop codon, interruption, and the like). The homologous sequences flanking the inactivating mutation are said to "flank" the mutation. Flanking, in this context, simply means that target homologous sequences are located both upstream (5') and downstream (3') of the mutation. These sequences should correspond to some sequences upstream and downstream of the target gene. The construct is then introduced into the cell, thus permitting recombination between the cellular sequences and the construct.

As a practical matter, the genetic construct will normally act as far more than a vehicle to interrupt the gene. For example, it is important to be able to select for recombinants and, therefore, it is common to include within the construct a selectable marker gene. This gene permits selection of cells that have integrated the construct into their genomic DNA by conferring resistance to various biostatic and biocidal drugs. In addition, a heterologous gene that is to be expressed in the cell also may advantageously be included within the construct. The arrangement might be as follows:

... vector.5'-flanking sequence-heterologous gene. selectable marker gene.flanking sequence-3'.vector ...

Thus, using this kind of construct, it is possible, in a single recombinatorial event, to (i) "knock out" an endogenous gene, (ii) provide a selectable marker for identifying such an event and (iii) introduce a transgene for expression.

Another refinement of the homologous recombination approach involves the use of a "negative" selectable marker. This marker, unlike the selectable marker, causes death of cells which express the marker. Thus, it is used to identify undesirable recombination events. When seeking to select homologous recombinants using a selectable marker, it is difficult in the initial screening step to identify proper homologous recombinants from recombinants generated from random, non-sequence specific events. These recombinants also may contain the selectable marker gene and may express the heterologous protein of interest, but will, in all likelihood, not have the desired "knock out" phenotype. By attaching a negative selectable marker to the construct, but outside of the flanking regions, one can select against many random recombination events that will incorporate the negative selectable marker. Homologous recombination should not introduce the negative selectable marker, as it is outside of the flanking sequences. Examples of processes that use negative selection to enrich for homologous recombination include the disruption of targeted genes in embryonic stem cells or transformed cell lines (Mortensen, 1993; Willnow and Herz, 1994) and the production of recombinant virus such as adenovirus (Imler et al., 1995).

Since the frequency of gene targeting is heavily influenced by the origin of the DNA being used for targeting, it is beneficial to obtain DNA that is as similar (isogenic) to the cells being targeted as possible. One way to accomplish this is by isolation of the region of interest from genomic DNA from a single colony by long range PCR. Using long range PCR it is possible to isolate fragments of 7–12 kb from small amounts of starting DNA.

Gene trapping is a useful technique suitable for use with the present invention. This refers to the utilization of the endogenous regulatory regions present in the chromosomal DNA to activate the incoming transgene. In this way expression of the transgene is absent or minimized when the transgene inserts in a random location. However, when homologous recombination occurs the endogenous regulatory region are placed in apposition to the incoming transgene, which results in expression of the transgene.

C. Site Specific Recombination

Members of the integrase family are proteins that bind to a DNA recognition sequence, and are involved in DNA recognition, synapsis, cleavage, strand exchange, and religation. Currently, the family of integrases includes 28 proteins from bacteria, phage, and yeast which have a common invariant His-Arg-Tyr triad (Abremski and Hoess, 1992). Four of the most widely used site-specific recombination systems for eukaryotic applications include: Cre-loxP from bacteriophage P1 (Austin et al., 1981); FLP-FRT from the 2μplasmid of *Saccharomyces cerevisiae* (Andrews et al., 1985); R-RS from *Zygosaccharomyces rouxii* (Maeser and Kahmann, 1991) and gin-gix from bacteriophage Mu (Onouchi et al., 1995). The Cre-loxP and FLP-FRT systems have been developed to a greater extent than the latter two systems. The R-RS system, like the Cre-loxP and FLP-FRT systems, requires only the protein and its recognition site. The Gin recombinase selectively mediates DNA inversion between two inversely oriented recombination sites (gix) and requires the assistance of three additional factors: negative supercoiling, an enhancer sequence and its binding protein Fis.

The present invention contemplates the use of the Cre/Lox site-specific recombination system (Sauer, 1993, available through Gibco/BRL, Inc., Gaithersburg, Md.) to rescue specific genes out of a genome, and to excise specific transgenic constructs from the genome. The Cre (causes recombination)-lox P (locus of crossing-over(x)) recombination system, isolated from bacteriophage P1, requires only the Cre enzyme and its loxP recognition site on both partner molecules (Sternberg and Hamilton, 1981). The loxP site consists of two symmetrical 13 bp protein binding regions separated by an 8 bp spacer region, which is recognized by the Cre recombinase, a 35 kDa protein. Nucleic acid sequences for loxP (Hoess et al., 1982) and Cre (Sternberg et al., 1986) are known. If the two lox P sites are cis to each other, an excision reaction occurs; however, if the two sites are trans to one another, an integration event occurs. The Cre protein catalyzes a site-specific recombination event. This event is bidirectional, i.e., Cre will catalyze the insertion of sequences at a LoxP site or excise sequences that lie between two LoxP sites. Thus, if a construct for insertion also has flanking LoxP sites, introduction of the Cre protein, or a polynucleotide encoding the Cre protein, into the cell will catalyze the removal of the construct DNA. This technology is enabled in U.S. Pat. No. 4,959,317, which is hereby incorporated by reference in its entirety.

An initial in vivo study in bacteria showed that the Cre excises loxP-flanked DNA extrachromosomally in cells expressing the recombinase (Abremski et al., 1983). A major question regarding this system was whether site-specific recombination in eukaryotes could be promoted by a bacterial protein. However, Sauer (1987) showed that the system excises DNA in *S. cerevisiae* with the same level of efficiency as in bacteria.

Further studies with the Cre-loxP system, in particular the ES cells system in mice, has demonstrated the usefulness of the excision reaction for the generation of unique transgenic animals. Homologous recombination followed by Cre-mediated deletion of a loxP-flanked neo-tk cassette was used to introduce mutations into ES cells. This strategy was repeated for a total of 4 rounds in the same line to alter both alleles of the rep-3 and mMsh2 loci, genes involved in DNA mismatch repair (Abuin and Bradley, 1996). Similarly, a transgene which consists of the 35S promoter/luciferase gene/loxP/35S promoter/hpt gene/loxP ($luc^+hyg^+$) was introduced into tobacco. Subsequent treatment with Cre causes the deletion of the hyg gene ($luc^+hyg^s$) at 50% efficiency (Dale and Ow, 1991). Transgenic mice which have the Ig light chain κ constant region targeted with a loxP-flanked neo gene were bred to Cre-producing mice to remove the selectable marker from the early embryo (Lakso et al., 1996). This general approach for removal of markers stems from issues raised by regulatory groups and consumers concerned about the introduction of new genes into a population.

An analogous system contemplated for use in the present invention is the FLP/FRT system. This system was used to target the histone 4 gene in mouse ES cells with a FRT-flanked neo cassette followed by deletion of the marker by FLP-mediated recombination. The FLP protein could be obtained from an inducible promoter driving the FLP or by using the protein itself (Wigley et al., 1994).

The present invention also contemplates the use of recombination activating genes (RAG) 1 and 2 to excise specific transgenic constructs from the genome, as well as to rescue specific genes from the genome. RAG-1 (GenBank accession number M29475) and RAG-2 (GenBank accession numbers M64796 and M33828) recognize specific recombination signal sequences (RSSs) and catalyze V(D)J recombination required for the assembly of immunoglobulin and T cell receptor genes (Schatz et al., 1989; Oettinger et al., 1990; Cumo and Oettinger, 1994). Transgenic expression of RAG-1 and RAG-2 proteins in non-lymphoid cells supports V(D)J recombination of reporter substrates (Oettinger et al., 1990). For use in the present invention, the transforming construct of interest is engineered to contain flanking RSSs. Following transformation, the transforming construct that is internal to the RSSs can be deleted from the genome by the transient expression of RAG-1 and RAG-2 in the transformed cell.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Following are the methods used in Example 1 to Example 5.

Materials and Methods

Cell Cultures. Mouse muscle myoblast C2C12 cells, mouse embryo fibroblast C3H10T1/2 clone, COS-7 cells, BALB/3T3 cells, S194 cells and PC12 cells were obtained from the American Type Culture Collection. C2C12 cells were maintained in Dulbecco's modified Eagle's medium (DMEM, Gibco BRL) containing 15% fetal bovine serum (FBS) and antibiotics (100 units/ml penicillin). When the C2C12 cells were incubated with human recombinant BMP-2, or TGF-β1, medium was replaced by DMEM containing 5% FBS and antibiotics. C3H10T1/2 cells, COS-7 cells, BALB/3T3 cells, S194 cells and PC12 cells were maintained in Dulbecco's modified Eagle's medium (DMEM) in the presence of 10% FBS and antibiotics.

RNA Isolation and Analysis.

Total RNA was isolated from the cells and mouse tissue by using Trizol (Gibco BRL) and poly(A)+ RNA was purified with Oligotex-dT30 (Qiagen) following the manufacturer's instructions. Analysis of RNA expression was performed by Northern blot as previously described (Sambrook et al., 1989). Probes used include a probe containing 3'-untranslated sequences of Osterix cDNA, the mouse Osteocalcin cDNA, mouse OSF2/Cbfa1 cDNA an 18S rRNA cDNA and the human GAPDH cDNA.

cDNA Cloning. C2C12 cells were cultured in DMEM containing 15% FBS to reach confluency, the serum was reduced to 5%, and the cells were allowed to grow in the presence or absence of 300 ng/ml BMP-2 for additional 24 h (Katagiri et al., 1994). Total RNA was extracted from the cells. Poly(A)+ RNA was further purified. cDNA from each total RNA was synthesised, amplified and subtracted by PCR by using PCR-Select cDNA Subtraction Kit (Clontech) following the manufacturer's instructions. After subtraction, the cDNA products were ligated into pCR2.1 (Invitrogen). Subtracted cDNA libraries were further screened by differential hybridisation with Differential Screening Kit (Clontech). To isolate full-length cDNA of Osterix, mouse calvaria cDNA library was screened with Osterix specific cDNA probe.

5'-RACE.

5'-RACE was performed by using FirstChoice RLM-RACE kit (Ambion) following the manufacturer's instructions.

In Situ Hybridization. To generate a probe for in situ hybridization analysis, the inventors cloned a 563-bp EcoRI fragment of Osterix cDNA encoding the 3'-untranslated sequence into EcoRi site of pBluescript KS(+). DNA was then either linearized with NotI and transcribed with T3 polymerase to yield a sense RNA probe, or linearized with XhoI and transcribed with T7 polymerase to yield an anti-sense RNA probe. Transcription reactions included [35S] UTP as label. In situ hybridizations were performed as described previously (Ausubel et al., 1995) with minor modifications. Slides were exposed for 8 days.

Plasmid Construction. A segment of the Osterix cDNA coding for amino acids 27–428 was cloned into the BamH1 and Xba1 sites of the vector pcDNA3.1–5UT-Flag (Lefebvre et al., 1997) to generate the mammalian expression plasmid pcDNAFlag-Osterix.

Gel Shift Analysis. For gel shift analysis, double-stranded oligonucleotides were labeled with polynucleotide kinase and [[gamma ]-32P]ATP. Probe oligonucleotides (20,000 cpm) were incubated with extract of COS-7 cells transfected with the Osterix expression vector at room temperature for 20 min. The reaction products were run on 4% polyacrylamide gels containing 0.25 X Tris borate-EDTA buffer at 4° C.

Transfection. For transcriptional activation studies, various segments of the Osterix cDNA were cloned between the EcoRI and XbaI sites of the Gal4 expression vector, pSG424 (Sadowski and Patshne, 1989) in-frame with the Gal4 DNA-binding domain. COS-7 cells were grown in DMEM containing 10% fetal calf serum in 8% C02. One microgram of Gal4 expression plasmid was transfected into cells along with 0.25 µg of a luciferase reporter plasmid containing five Gal4 DNA-binding sites and E1b promoter (Luo and Sawadogo, 1996) and 0.25 µg of pSV-β-Gal as an internal control. The cells were transfected with Fugene6 (Gibco BRL) and harvested 24 h after transfection. Luciferase activities and β-Galactosidase activities were measured as described (Ausubel et al., 1995). To obtain recombinant Osterix protein, pcDNAFlag-Osterix was transfected into COS-7 cells with Fugene6 (Gibco BRL) and harvested 24 h after transfection.

Purification of anti Osterix antibodies. Antibodies were created by immunizing rabbits with a 14-amino acid peptide (AHGGSPEQSNLLEI; SEQ ID NO: 3) located at the C-terminus of the Osterix protein. The antibodies were affinity purified over a 3M Emphaze Biosupport Medium AB1 column (Pierce) coupled to the 14-amino acid peptide and were eluted at low and high pH. They were then dialysed against Tris-buffered saline.

Western Blotting. Cell lysates were prepared as described previously (Schreiber et al., 1989), and Western blotting was performed with the ECL kit (Amersham). Mouse anti-FLAG M2 antibodies and mouse anti-Gal4 DNA-binding domain were purchased from Sigma and Santa Cruz, respectively.

Chromosome Localization. The chromosomal location of Osterix was determined by Southern hybridization to a mouse interspecific mapping panel obtained from The Jackson Laboratory. The panel was composed of genomic DNA from 94 backcross progeny from an interspecific cross between (C56BL/6J X SPRET/Ei) F1 hybrid female and SPRET/Ei male mice (Rowe et al., 1994). A Southern blot membrane containing genomic DNA samples from backcross progeny digested with HindIII was hybridized with the 0.5-kb DNA probe. The restriction fragment length polymorphism distribution pattern was submitted to The Jackson Laboratory for analysis.

Example 1

Cloning of a cDNA for an Osteoblast-enriched Transcription Factor

To identify potential osteoblast-specific proteins the inventors used a suppression-subtractive hybridization method combined with differential hybridization screening. The growth medium of C2C12 cells, consisting of DMEM containing 15% FBS, was reduced to 5% serum, and when the cells reached confluency, the cells allowed to grow in the presence or absence of 300 ng/ml BMP-2 for an additional 24 h (Katagiri et al., 1994). Thereafter, poly(A)+ RNA from both cells were prepared, reverse transcribed into first strand cDNAs. After synthesis of second strand cDNAs, these cDNA pools were then used for the PCR-based suppression-subtractive hybridization. In this procedure cDNAs corresponding to C2C12 cells grown in the absence of BMP were subtracted from cDNAs corresponding to C2C12 cells grown in the presence of BMP. Five hundred clones randomly chosen from the subtracted cDNA library were used in a differential hybridization screening. Twenty-eight cDNA clones were chosen that were positive with cDNA probes prepared from C2C12 cells after BMP-2-treatment but were negative with cDNA probes from these cells not treated with BMP-2. The DNA sequence of the clones was determined and tested in Genbank searches. Twelve cDNA clones corresponded to previously identified proteins in humans or mice. Sixteen cDNA clones were further tested in Northern hybridizations with RNAs from C2C12 cells either untreated or treated with BMP2. Eight cDNA clones showed no hybridization to RNA from untreated C2C12 cells and a strong signal with RNAs from BMP-2-treated cells. One of these cDNAs hybridized to a major transcript of approximately 3.0 kb that was strongly induced in the BMP-2-treated cells (see below). This cDNA clone was subsequently used to identify full length cDNA, the sequencing of which showed an open reading frame of 1284 nucleotides beginning with a ATG codon capable of encoding a 428-amino acid polypeptide with predicted molecular weight of 44.7 kDa (FIG. 2A). A 5' RACE experiment was performed to identify the 5' end of the mRNA in BMP-2-treated C2C12 cells. An additional 71 nucleotides were identified that preceded the sequence of the cDNA clone shown in FIG. 2A. This sequence which did not contain an additional in-frame methionine codon or stop codons, was also found immediately preceding the most 5' 49 nucleotides of FIG. 2A in the mouse genome.

To examine the size of the endogenous polypeptide, antibodies were raised against a 14 amino acid peptide located at the C-termini of the polypeptide and further purified. The purified antibodies recognised a 46 kDa protein present in extracts from C2C12 cells treated with BMP-2. The mobility of this polypeptide in SDS-PAGE was identical to that of the recombinant polypeptide expressed in COS-7 cells (FIG. 3). The predicted molecular weight of the endogenous polypeptide was in agreement with the size predicted from the deduced amino acid sequence. The mobility of the polypeptide in SDS-PAGE was also not affected by reducing agents. Thus, the cDNA as depicted by FIG. 2A encodes the full-length polypeptide.

The amino acid sequence predicts the existence of three C2H2 type zinc-finger motifs at the carboxyl terminus. As shown in FIG. 2B these zinc-fingers have a high degree of homology with those present in Sp1, Sp3, and SP4. A lower but significant homology was also found with the zinc-finger regions of other proteins including, Sp2, FKLF-2, BTEB-1, and the TGF-β inducible early gene TIEG-1 and TIEG-2. The amino terminal 285 amino acids of the protein contain a domain rich in proline (14.7%) and serine (10.2%) residues characteristic of transcriptional activation domains. Upstream of the zinc finger domain was a stretch of basic amino acids similar to a region in EGR-1 that has been shown to be important for nuclear localization (Gashler et al., 1993). Thus, a novel polypeptide bearing transcription factor domains is provided herein.

Example 2

Expression Pattern

Figure 1A:
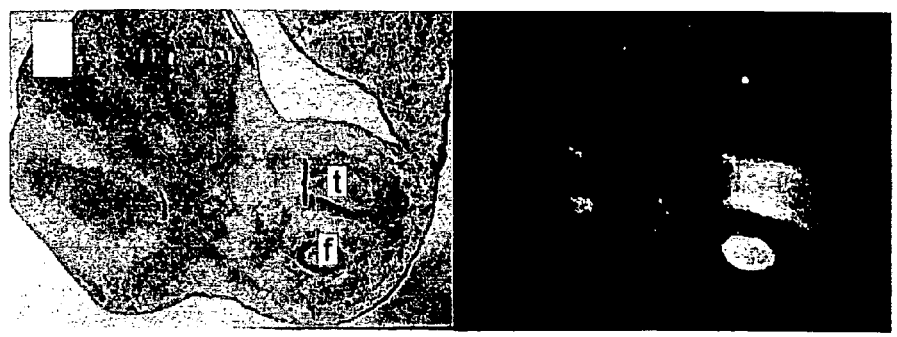
FIG. 1A, FIG. 1B, FIG. 1C, FIG. 1D, FIG. 1E, and FIG. 1F. Expression of Osterix mRNA in skeletal cells as detected by in situ hybridization.
Figure 1B:
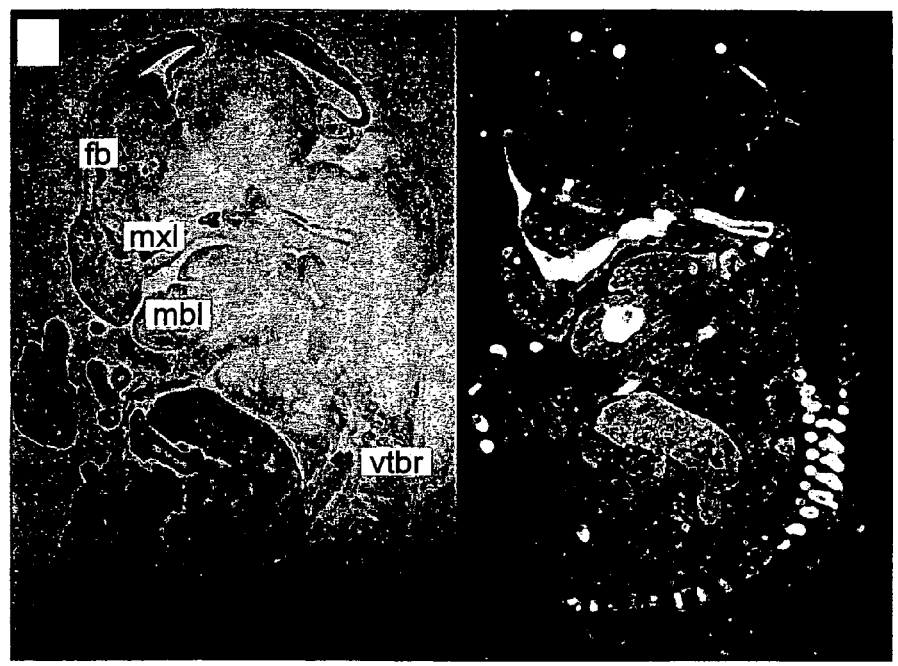
Figure 1C:
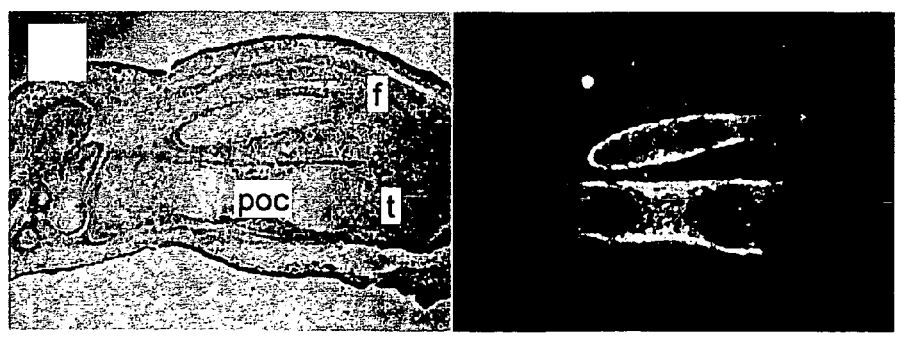
Figure 1D:
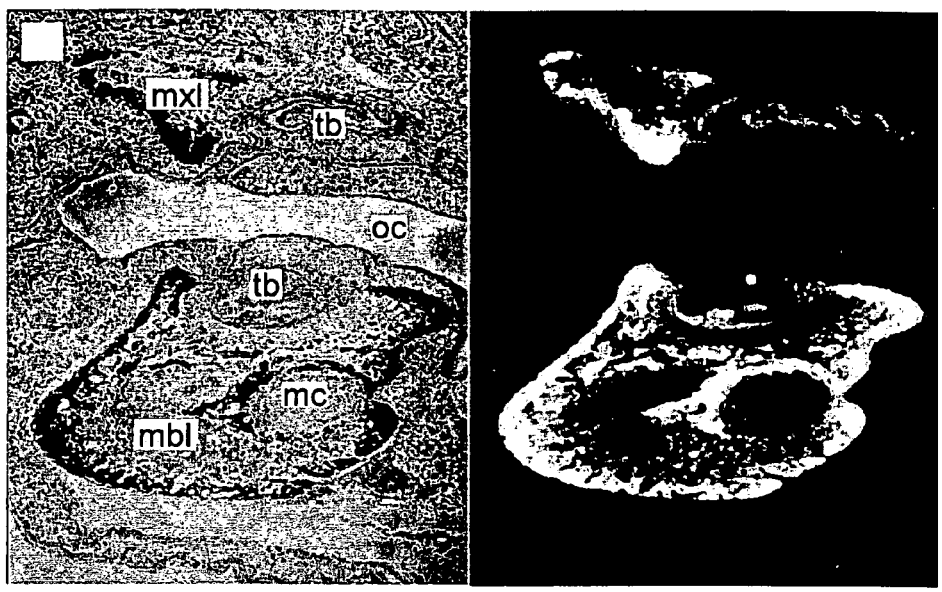
Figure 1E:
Figure 1F:
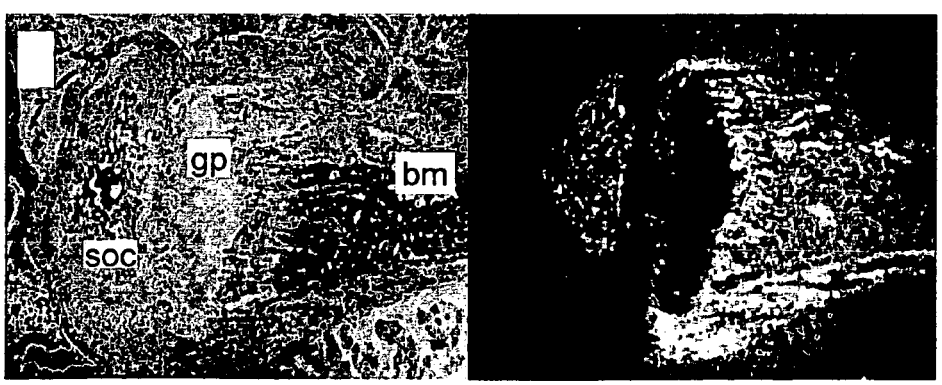

To identify the cell types that expressed this RNA in vivo, the inventors performed in situ hybridization with mouse embryos at various stages and also with tissues from newborn mice. Representative examples are shown in FIG. 1A, FIG. 1B, FIG. 1C, FIG. 1D, FIG. 1E, and FIG. 1F. At 13.5 days of embryonic development transcripts were detected in mesenchymal cells undergoing chondrocyte differentiation (FIG. 1A). A weaker signal was also detected in mesenchymal condensations of digits. At E 14.5 expression was detected in mesenchymal cells in the maxilla, mandible and frontal bone prominence. Transcripts were also detected in other skeletal elements including vertebrae (FIG. 1B). At this stage transcripts were confined to the peripheral layer of cartilages and were absent from more centrally located chondrocytic cells. Small intestine, liver, thymus and lung showed little or no signal. At E15.5 strong expression was found in cells of all primary ossification centers. Weak expression was also detected in the prehypertrophic zone of growth plate cartilages (FIG. 1C). At E16.5 cells that form the maxilla and mandible and mesenchymal cells of tooth germ (FIG. 1D) showed a positive signal whereas little or no expression was detected in Meckel's cartilage or epithelial tissue of tooth germs. At E17.5 days of development, expression was strong in the periosteum and in cells associated with bone trabecules (FIG. 1E). In mice 13 days after birth, expression was detected in bone trabecules as well as in cells forming secondary ossification centers (FIG. 1F). Overall, these results provide that in vivo, the Osterix gene is expressed in osteoblasts of all bones formed by either membraneous or endochondral ossification. In skeletal elements formed by endochondral ossification it is first expressed in differentiating chondrocytes, then in the perichondrium and nascent osteoblasts. In skeletal elements formed by membranous ossification it is first expressed in mesenchymal cell condensation then in osteoblasts. Osterix is also expressed at lower levels in the prehypertrophic chondrocytes of endochondral bones.

Figure 9B:
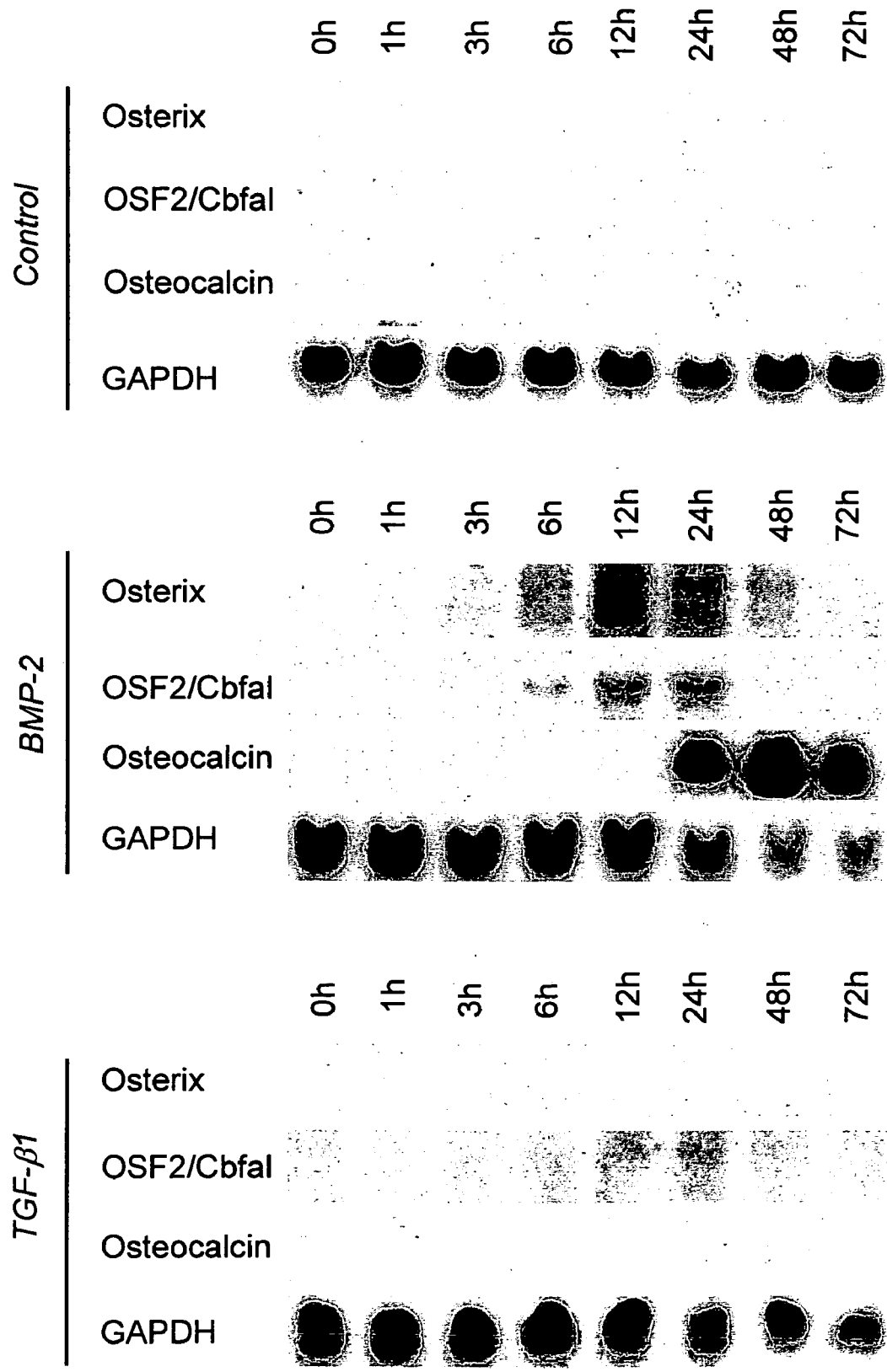

To determine at what time after BMP-2 addition to C2C12 cells Osterix RNA was expressed a time course study was performed. Northern blot analysis revealed that expression of the Osterix gene was detected as early as 3 h after the addition of BMP-2, peaked at 12–24 h, and decreased after 48 h (FIG. 9B). Expression was parallel to that of OSF2/Cbfa1, a critical transcription factor of osteoblast differentiation, and preceded that of osteocalcin mRNA, a molecular marker of osteoblast differentiation. To investigate whether TGF-β1, another member of the TGF-β superfamily, would induce the Osterix gene, the inventors treated C2C12 cells with TGF-β1. Although, like BMP-2, TGF-β1 inhibited myotube formation (FIG. 9A), it did not induce expression of osteocalcin mRNA in C2C12 cells (FIG. 9B). TGF-β1 had no effect on expression of the Osterix mRNA (FIG. 9B). Osterix RNA was expressed in ROS17/2.8 and MC3T3-E1 cells, which are osteoblast cell lines, as well as in rat chondrosarcoma cells (RCS), a well differentiated chondrocytic cell line, but it was not expressed in BALB/3T3 fibroblast cells, S194 B cells or PC12 cells (FIG. 9C). When various tissues of newborn mice were analysed Osterix RNA was only detected in calvaria and not in the other tissues listed in FIG. 9C.

Example 3

Biochemical Characterization of the Recombinant Osterix Protein

The three zinc-finger motifs located at the C-terminal part, and their high degree of sequence homology with a similar motif in SP1, SP3 and SP4, indicated that the polypeptide may bind to DNA. A recombinant polypeptide (amino acids 17–428) was generated by transfection of a Osterix expression vector into COS-7 cells. Using extracts of transfected cells, gel shift assays were performed with double stranded oligonucleotide that contained a consensus Sp1 binding site, shown previously to bind to related zinc-finger proteins. Increasing levels of a specific DNA-protein complex were formed with increasing amounts of extracts (FIG. 4A). Formation of the specific complex was inhibited by incubation with the anti C-terminal Osterix antibodies (FIG. 4B). Moreover, this inhibition was restored by further incubation with excess of C-terminal peptide that was used to generate the antiserum, indicating that the complex consists of the recombinant Osterix and labeled probe.

Figures 6A, 6B:
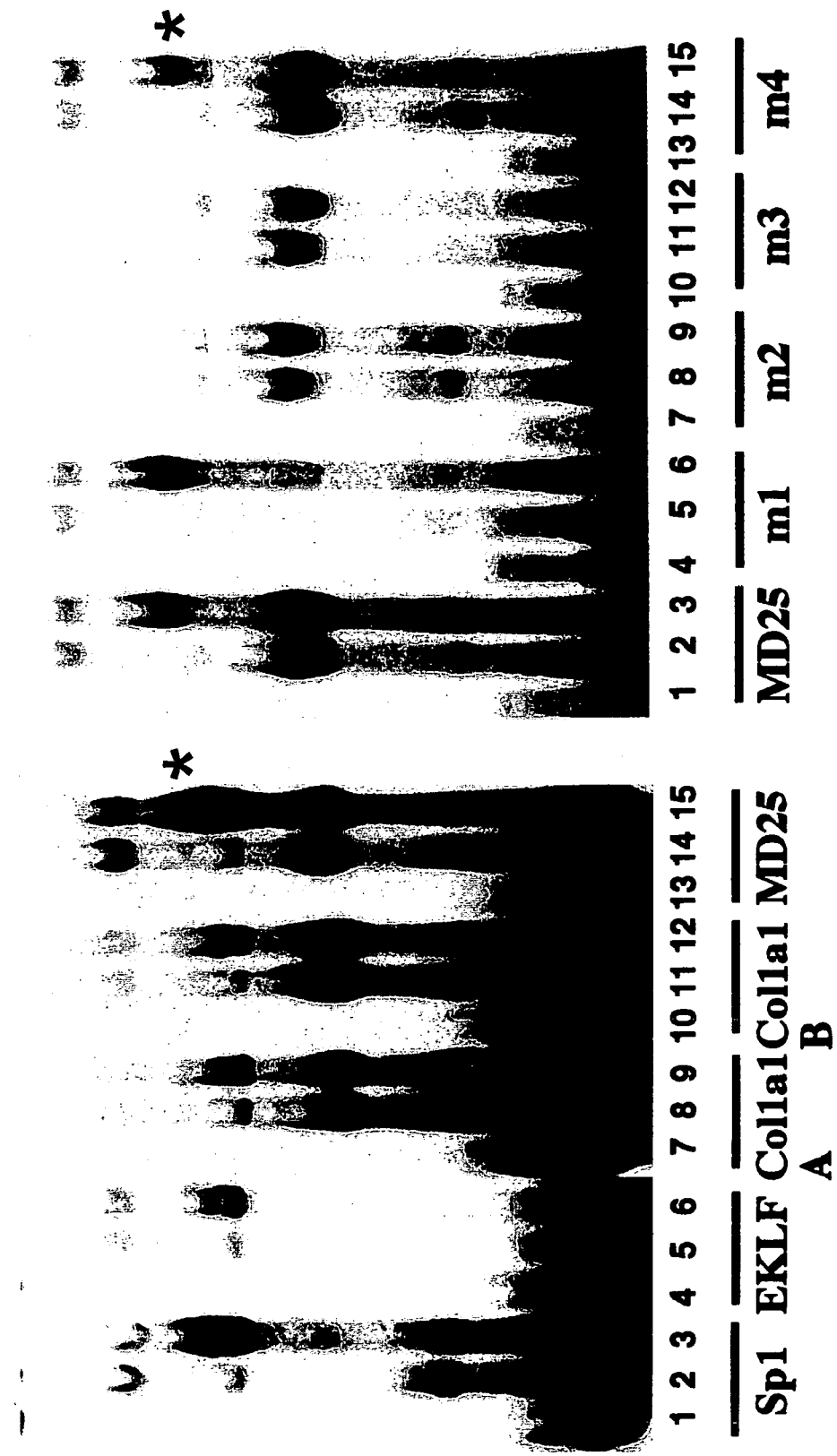
FIG. 6A and FIG. 6B. Binding of Osterix to various oligonucleotide.

Binding abilities of different double stranded oligonucleotides containing G/C boxes (see Table 4) were also tested (FIG. 6A and FIG. 6B). The results showed that Osterix bound efficiently to several G/C-rich sequences including the EKLF consensus site and G/C-rich sequences in the Col1a1 and Col2a1 promoters. Mutations were introduced in the Col2a1 site to further delineate the binding sequence. This site is very similar to a consensus site for SP1 binding. Mutations in central G residues abolish binding of Osterix to probes.

Figure 7A:
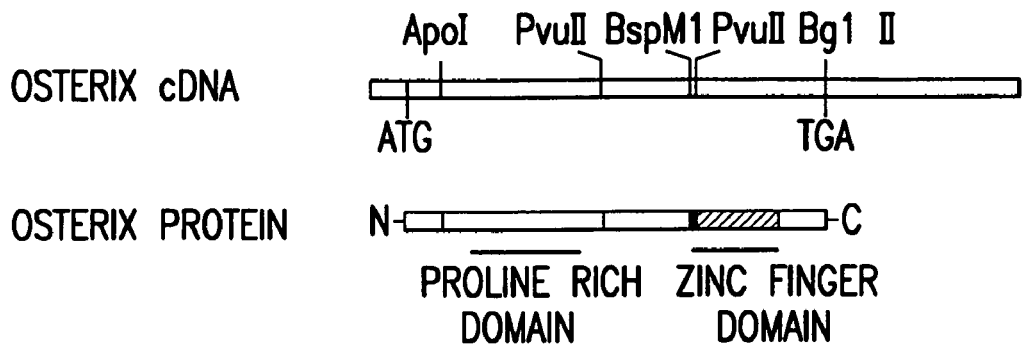
FIG. 7A, FIG. 7B, and FIG. 7C. Transcriptional activation studies.
Figure 7B:
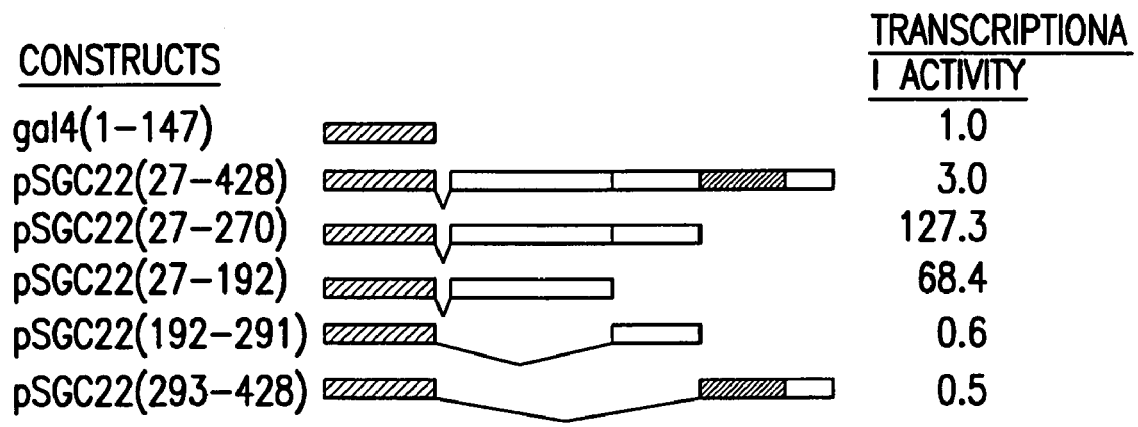
Figure 7C:
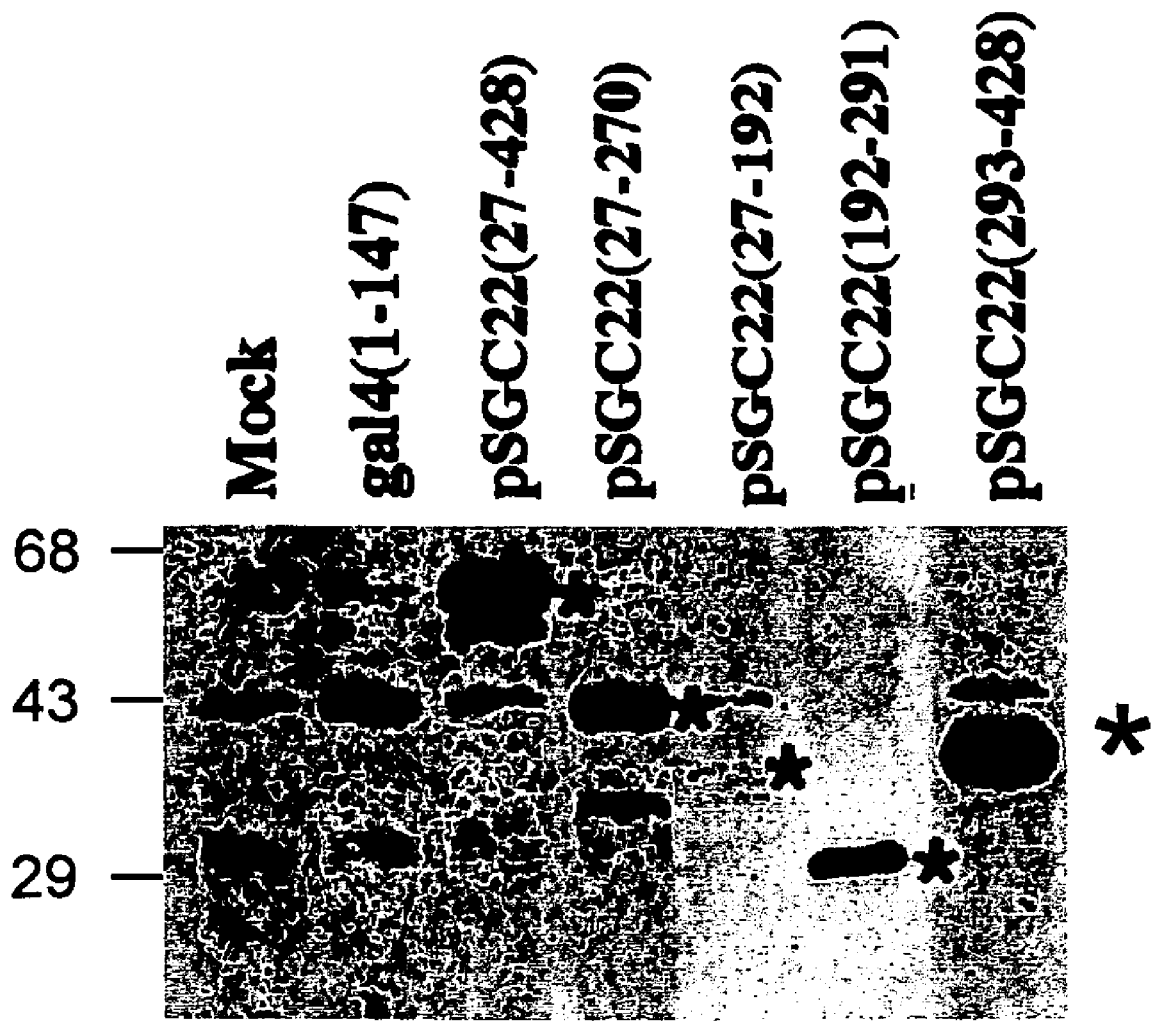

The inventors also tested whether Osterix contained transcription activation domains. Various segments of Osterix were fused in-frame with the DNA-binding domain of the yeast transcription factor Gal4 and the fusion polypeptide was expressed in COS-7 cells along with a reporter gene containing five Gal4-binding sites and E1b minimal promoter. A plasmid expressing the Gal4 DNA-binding domain was transfected as a control. FIG. 7A, FIG. 7B, and FIG. 7C show that the segment containing residues 27 to 270 and the smaller proline/serine-rich segment from residues 27 to 192 provided a strong transcriptional activation function. Neither the full-length protein (1–474) nor the zinc-finger region of Osterix (363–474) had the ability to activate transcription when fused to Gal4 DNA-binding domain. The inventors contemplate that the full-length protein lacked activity because it had a higher affinity for endogenous target sites in COS-7 chromatin than it did for the Gal4-binding sites in the reporter gene. Alternatively, they contemplate that the zinc-finger region may have masked the activation domain or contained additional domains that repressed the activity of the proline-rich region.

Example 4

Mapping of the Osterix Gene

To determine the chromosomal location of the Osterix gene in the mouse genome, a interspecific mapping panel of DNA samples obtained from the Jackson Laboratory was analyzed. This panel consisted of 94 backcross progeny genomic DNA from an interspecific cross between (C57BL/63 X SPRET/Ei) F1 hybrid female and SPRET/Ei male mice. A 0.3 kb Hind III cDNA probe was first used to identify a HindIII restriction fragment length polymorphism between C57BL/6J and SPRET/Ei genomic DNA. This probe was then used with genomic DNA of the 94 genomic DNA samples of the backcross progeny panel. Haplotypes of this panel were compared with other previously mapped markers. The mapping results indicate that the Osterix gene is located on mouse chromosome 15 between Sca 8a and Itga5. Based on the chromosomal location of these genes, the predicted syntenic region for the human OSTERIX gene is chromosome 12q13. No inherited skeletal human disease has been mapped to this region.

TABLE 4

| | | | |
|---|---|---|---|
| Sp1: | 5'-ATTCGATCGGGGCGGGGCGAGC-3' | 17mer | SEQ ID NO:24 |
| EKLFU: | 5'-CGTAGAGCCACACCCTGAAGG-3' | 21mer | SEQ ID NO:25 |
| EKLFL: | 5'-CCTTCAGGGTGTGGCTCTAGG-3' | 21mer | SEQ ID NO:26 |
| Col1a1AU: | 5'-TTGCGGGAGGGGGGGCGCGCTGGGTGGA-3' | 28mer | SEQ ID NO:27 |
| Col1a1AL: | 5'-TCCACCCAGCGCGCCCCCCCTCCCGCAA-3' | 28mer | SEQ ID NO:28 |
| Col1a1BU: | 5'-CCTTCCTTTCCCTCCTCCCCCCTCTTCG-3' | 28mer | SEQ ID NO:29 |
| Col1a1BL: | 5'-CGAAGAGGGGGAGGAGGGAAAGGAAGG-3' | 28mer | SEQ ID NO:30 |
| Col2a1U: | 5'-GCTCGGGGGCGGGGTCTCAGGTTA-3' | 24mer | SEQ ID NO:31 |

TABLE 4-continued

| Name | Sequence | Length | SEQ ID |
|---|---|---|---|
| Col2a1L: | 5'-TAACCTGAGACCCCGCCCCCGAGC-3' | 24mer | SEQ ID NO:32 |
| MD25/27U: | 5'-GGGCTCCGGGGGCGGGGTCTCAGGTTA-3' | 27mer | SEQ ID NO:33 |
| MD25/27L: | 5'-TAACCTGAGACCCCGCCCCCGGAGCCC-3' | 27mer | SEQ ID NO:34 |
| MD25/27m1U: | 5'-GGGCTCCGGGGGCGGGGTCTCATTTTA-3' | 27mer | SEQ ID NO:35 |
| MD25/27m1L: | 5'-TAAAATGAGACCCCGCCCCCGGAGCCC-3' | 27mer | SEQ ID NO:36 |
| MD25/27m2U: | 5'-GGGCTCCGGGGGCTTGTCTCAGGTAA-3' | 27mer | SEQ ID NO:37 |
| MD25/27m2L: | 5'-TAACCTGAGACAACGCCCCCGGAGCCC-3' | 27mer | SEQ ID NO:38 |
| MD25/27m3U: | 5'-GGGCTCCGGCTTCGGGGTCTCAGGTTA-3' | 27mer | SEQ ID NO:39 |
| MD25/27m3L: | 5'-TAACCTGAGACCCCGAACCCGGAGCCC-3' | 27mer | SEQ ID NO:40 |
| MD25/27m4U: | 5'-GGGCTCATGGGGCGGGGTCTCAGGTTA-3' | 27mer | SEQ ID NO:41 |
| MD25/27m4L: | 5'-TAACCTGAGACCCCGCCCCATGAGCCC-3' | 27mer | SEQ ID NO:42 |
| RD25/27U: | 5'-AGGCTCCGGGGGCGGGGTCTCAGGTTA-3' | 27mer | SEQ ID NO:43 |
| MD25/27U: | 5'-GGGCTCCGGGGGCGGGGTCTCAGGTTA-3' | 27mer | SEQ ID NO:44 |
| MD25/27m1U: | 5'-GGGCTCCGGGGGCGGGGTCTCATTTTA-3' | 27mer | SEQ ID NO:45 |
| MD25/27m2U: | 5'-GGGCTCCGGGGGCTTGTCTCAGGTTA-3' | 27mer | SEQ ID NO:46 |
| MD25/27m3U: | 5'-GGGCTCCGGGTTCGGGGTCTCAGGTTA-3' | 27mer | SEQ ID NO:47 |
| MD25/27m4U: | 5'-GGGCTCATGGGGCGGGGTCTCAGGTTA-3' | 27mer | SEQ ID NO:48 |
| MD25/27U: | 5'-GGGCTCCGGGGGCGGGGTCTCAGGTTA-3' | 27mer | SEQ ID NO:49 |
| MD25/27U: | 5'-GGGCTCCGGGGGCGGGGTCTCAGGTTA-3' | 27mer | SEQ ID NO:50 |

Example 5

Discussion

The invention provides a novel member of the Sp/XKLF family of zinc-finger proteins, that contains three carboxyl-terminal zinc fingers. The 85 residue three-zinc finger-domain of Osterix is closely related to that of the SP family and somewhat more distantly related to that of mBTEB-1. Outside the zinc finger domain there are no sequence homologies with other proteins in the Genbank database, although the amino-terminal portion is rich in proline and serine residues which is typical of certain transcription activation domains. Recombinant Osterix is capable of binding to several G/C-rich binding sites which is a target for the closely related transcription factor Sp1. The proline/serine-rich region of Osterix fused to a heterologous DNA-binding domain was able to function as a strong transcriptional activator. Together these data indicate that Osterix binds to a subset of G/C-rich sites similar to those recognized by Sp1 and EKLF, and activates transcription through an amino-terminal proline/serine rich domain.

Osterix was isolated in a screen to identify novel genes that are specifically expressed in osteoblasts. To this effect the mouse myoblastic C2C12 cell line was used which upon treatment with BMP-2 differentiates into osteoblasts. A PCR-based subtraction method coupled with a differential hybridization screening was used to identify mRNAs that were induced after BMP-2 treatment but were either absent or present at very low levels in untreated cells. The increase in Osterix mRNA was detectable 3 hours after BMP-2 addition to C2C12 cells and peaked at 12–24 hours. The kinetics of Osterix induction by BMP-2 were essentially identical to those of Cbfa1 induction by BMP-2 in this system and preceded induction of osteocalcin by BMP-2. In contrast, TGF-β which does not induce an osteoblastic phenotype in C2C12 cells, did not induce Osterix expression. The gene for a putative zinc finger protein, called TGF-βinducible early gene (TIEG), is induced by both BMP-2 and by TGF-β(Subramaniam et al., 1995). Expression of TIEG has been reported to be associated with osteoblast differentiation. A detailed analysis of the regulatory mechanism of Osterix expression allows the elucidation of the molecular pathways involved in BMP signalling in osteoblast differentiation. Thus, the inventors contemplate further experiments to disclose the functional role of Osterix in BMP-induced osteoblastic differentiation.

Analysis of the expression pattern of the Osterix transcripts during embryonic development indicated that expression occurs in mesenchymal cells undergoing chondrocyte differentiation; detection of the transcripts subsequently shifted to the perichondrium mainly around the hypertrophic zone and starting around E14.5 in cells associated with bone trabeculae in primary ossification centers. Osterix is expressed in all ossification centers throughout the skeleton both in skeletal elements that are formed by endochondral ossification and those formed by membranous ossification. Furthermore, after birth, Osterix transcripts are found in secondary ossification centers and continue to be found in cells associated with all bone trabeculae. Osterix RNA is expressed in the prechypertrophic zone of growth plates of endochondral bones at much lower levels than in ossification centers. Overall, the pattern of expression of Osterix in skeletogenesis first early during cartilage formation, then during osteoblast differentiation and later in all osteoblastic cells is very similar to that of Cbfa1. One difference is that in contrast to Cbfa1 Osterix is not expressed in the hypertrophic zone of growth plates but in the prehypertrophic zone. Thus, the pattern of expression of Osterix is consistent with its role as a transcription factor in the pathway of osteoblast differentiation.

To better understand the function of Osterix the inventors are currently performing experiments to inactivate the corresponding gene by homologous recombination in mouse embryonic stem cells. These experiments are in progress and the general guidelines are provided in previous sections of this specification.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ausubel, Brent, Kingston, Moore, Seidman, Smith, Struhl, "Short protocols in molecular biology", 3rd Ed., John Wiley & Sons, Inc., New York, 1995.
Barribault et al., *Mol. Biol. Med.,* 6:481–492, 1989.
Bi, Deng, Zhang, Behringer, de Crombrugghe, *Nat Genet,* 22(1), 85–9, 1999.
Bradley et al., *Bio/Technology,* 1992.
Bradley et al., *Nature* 309:255–258, 1984.
Capecchi, *Science,* 244:1288–1292, 1989.
Capecchi, *Trends in Genet.,* 5:70–76, 1989.
Dolle, Dierich, LeMeur, Schimmang, Schuhbaur, Chambon, Duboule, *Cell,* 75(3), 431–41, 1993.
Erlebacher, Filvaroff, Gitelman, Derynck, *Cell,* 80(3), 371–8, 1995.
Evans et al., *Nature* 292:154–156, 1981.
Floyd, C. D. et al., *Prog. Med. Chem.,* Combinatorial chemistry as a tool fro drug discovery, 36, 91–168, 1999.
Frohman et al., *Cell,* 56:145–147, 1989.
Gashler, Swaminathan, Sukhatme, *Mol Cell Biol,* 13(8), 4556–71, 1993.
Gordon, Transgenic Animals, *Intl. Rev. Cytol.,* 115:171–229, 1989.
Gossler et al., *Proc. Natl. Acad. Sci. USA,* 83:9065–9069, 1986.
Hogan, *Genes Dev,* 10(13), 1580–1594, 1996.
Hoppe and Wagner, U.S. Pat. No. 4,873,191, 1989.
Horinouchi et al., *Nature Genetics,* 10:288–293, 1995.
Hui and Joyner, *Nat Genet,* 3(3), 241–246, 1993.
Jaenisch, *Science,* 240:1468–1474, 1988.
Katagiri, Yamaguchi, Komaki, Abe, Takahashi, Ikeda, Rosen, Wozney, Fujisawa-Sehara, Suda, *J Cell Biol,* 127(6 Pt 1), 1755–66, 1994.
Kim et al., *Nucl. Acids Res.* 16:8887–8903, 1988.
Kim et al., *Gene* 103:227–233, 1991.
Komori, Yagi, Nomura, Yamaguchi, Sasaki, Deguchi, Shimizu, Bronson, Gao, Inada, Sato, Okamoto, Kitamura, Yoshiki, Kishimoto, *Cell,* 89(5), 755–764, 1997.
Lavitrano et al., *Cell,* 57:717–723, 1989.
Lefebvre, Huang, Harley, Goodfellow, de Crombrugghe, *Mol Cell Biol,* 17(4), 2336–2346, 1997.
Lo, *Mol Cell. Biol.,* 3:1803–1814, 1983.
Luo and Sawadogo, *Mol Cell Biol,* 16(4), 1367–75, 1996.
Mansour et al., *Nature,* 336:348–352, 1988.
Otterbach and Stoffel, *Cell,* 81:1053–1061, 1995.
Otto, Thornell, Crompton, Denzel, Gilmour, Rosewell, Stamp, Beddington, Mundlos, Olsen, Selby, Owen, *Cell,* 89(5), 765–71, 1997.
Peters, Neubuser, Kratochwil, Balling, *Genes Dev,* 12(17), 2735–47, 1998.
Robertson et al., *Nature,* 322:445–448, 1986.
Rowe, Nadeau, Turner, Frankel, Letts, Eppig, Ko, Thurston, Birkenmeier, *Mamm Genome,* 5(5), 253–274, 1994.
Sadowski and Ptashne, *Nucleic Acids Res,* 17(18), 7539, 1989.
Sambrook, Fritsch, Maniatis, *Molecular Cloning: In. A Laboratory Manual,* 2nd Ed Ed., Cold Spring Harbor Laboratory, Cold Spring Harbor, N.Y., 1989.
Schreiber, Matthias, Muller, Schaffner, *Nucleic Acids Res,* 17(15), 6419, 1989.
Sedivy et al., *Proc. Natl. Acad. Sci. USA,* 86:227–231, 1989.
Small et al., 1985, *Mol. Cell Biol.* 5:642–648.
Subramaniam, Harris, Oursler, Rasmussen, Riggs, Spelsberg, *Nucleic Acids Res,* 23(23), 4907–4912, 1995.
Thomas and Capecchi, *Cell,* 51:503–512, 1987.
Thompson et al., *Cell,* 56:313–321, 1989.
Van der Putten et al., *Proc. Natl. Acad. Sci., U.S.A.,* 82:6148–6152, 1985.
Van Hijftel et al, *J. Chromatogr. B. Biomed. Sci. Appl.,* Combinatorial chemistry automation and molecular diversity: new trends in the pharmaceutical industry, 725, 3–15, 1999.
Wagner, *EMBO J.,* 9:3025–3032, 1990.
Wilm, Dahl, Peters, Balling, Imai, *Proc Natl Acad Sci USA,* 95(15), 8692–8697, 1998
Wood et al., *Proc. Natl. Acad. Sci. U.S.A.* 90:4582–4584, 1993. .

What is claimed is:

1. An isolated DNA segment comprising a protein coding region encoding an Osterix polypeptide, wherein said polypeptide comprises a transactivation domain, a zinc finger domain and a proline rich domain, wherein the Osterix polypeptide has the sequence of SEQ ID NO:2.

2. The DNA segment of claim 1, wherein the Osterix coding region is positioned under the control of a promoter.

3. The DNA segment of claim 2, wherein said promoter is a recombinant promoter.

4. The DNA segment of claim 2, further defined as a recombinant vector.

5. An isolated recombinant host cell comprising the DNA segment of claim 1.

6. The recombinant host cell of claim 5, further defined as a prokaryotic host cell.

7. The recombinant host cell of claim 6, wherein the prokaryotic host cell is a bacterial host cell.

8. The recombinant host cell of claim 7, wherein the bacterial host cell is *E. coli*.

9. The recombinant host cell of claim 5, further defined as a eukaryotic host cell.

10. The recombinant host cell of claim 9, further defined as an osteoblast.

11. The recombinant host cell of claim 10, wherein said osteoblast is a BMP2-treated C2C12 cell.

12. The recombinant host cell of claim 9, further defined as a mesenchymal precursor cell.

13. An isolated recombinant host cell comprising the DNA segment of claim 4.

14. An isolated expression cassette comprising a polynucleotide encoding a polypeptide having the sequence of SEQ ID NO:2, wherein said polynucleotide is under the control of a promoter operably in eukaryotic cells.

15. The expression cassette of claim 14, wherein said promoter is heterologous to the polynucleotide encoding a polypeptide having the sequence of SEQ ID NO:2.

16. The expression cassette of claim 14, wherein said promoter is a tissue specific promoter.

17. The expression cassette of claim 14, wherein said promoter is an inducible promoter.

18. The expression cassette of claim 14, wherein said expression cassette is contained in a viral vector.

19. The expression cassette of claim 18, wherein said viral vector is selected from the group consisting of a retroviral vector, an adenoviral vector, and adeno-associated viral vector, a vaccinia viral vector, and a herpesviral vector.

20. The expression cassette of claim 14, wherein said expression cassette further comprises a polyadenylation signal.

21. An isolated cell comprising an expression cassette comprising a polynucleotide encoding a polypeptide having the sequence of SEQ ID NO:2, wherein said polynucleotide is under the control of a promoter operable in eukaryotic cells, said promoter being heterologous to said polynucleotide.

* * * * *

UNITED STATES PATENT AND TRADEMARK OFFICE
CERTIFICATE OF CORRECTION

PATENT NO. : 7,160,722 B2
APPLICATION NO. : 09/734329
DATED : January 9, 2007
INVENTOR(S) : de Crombrugghe et al.

Page 1 of 1

It is certified that error appears in the above-identified patent and that said Letters Patent is hereby corrected as shown below:

In claim 14, column 78, line 15, delete " operably" and insert --operable-- therefor.

Signed and Sealed this

Twenty-ninth Day of May, 2007

JON W. DUDAS
*Director of the United States Patent and Trademark Office*